(12) United States Patent
Masters

(10) Patent No.: US 11,890,371 B2
(45) Date of Patent: Feb. 6, 2024

(54) BIOCOMPATIBLE PROTEIN-BASED PARTICLES AND METHODS THEREOF

(75) Inventor: David B. Masters, Minneapolis, MN (US)

(73) Assignee: PETVIVO HOLDINGS, INC., Edina, MN (US)

(*) Notice: Subject to any disclaimer, the term of this patent is extended or adjusted under 35 U.S.C. 154(b) by 26 days.

(21) Appl. No.: 12/344,361

(22) Filed: Dec. 26, 2008

(65) Prior Publication Data

US 2010/0143487 A1    Jun. 10, 2010

Related U.S. Application Data

(60) Provisional application No. 61/016,744, filed on Dec. 26, 2007.

(51) Int. Cl.
*A61K 9/00* (2006.01)
*A61K 9/14* (2006.01)

(52) U.S. Cl.
CPC .............. *A61K 9/0019* (2013.01); *A61K 9/14* (2013.01)

(58) Field of Classification Search
None
See application file for complete search history.

(56) References Cited

U.S. PATENT DOCUMENTS

| | | | |
|---|---|---|---|
| 3,800,792 A | 4/1974 | McKnight | 602/50 |
| 3,996,934 A | 12/1976 | Zaffaroni | 424/434 |
| 4,060,081 A | 11/1977 | Yannas | 623/15.12 |
| 4,226,848 A | 10/1980 | Nagai | 514/772.1 |
| 4,250,163 A | 2/1981 | Nagai | 514/772.1 |
| 4,252,759 A | 2/1981 | Yannas | 264/86 |
| 4,280,954 A | 7/1981 | Yannas | 530/356 |
| 4,286,592 A | 9/1981 | Chandrasekaran | 424/448 |
| 4,292,299 A | 9/1981 | Suzuki | 424/435 |
| 4,347,234 A | 8/1982 | Wahlig | 424/426 |
| 4,350,629 A | 9/1982 | Yannas | 530/356 |
| 4,352,883 A | 10/1982 | Lim | 435/178 |
| 4,394,370 A | 7/1983 | Jefferies | 606/76 |
| 4,405,311 A | 9/1983 | Greatbatch | 604/20 |
| 4,418,691 A | 12/1983 | Yannas | 424/548 |
| 4,438,253 A | 3/1984 | Casey et al. | 528/86 |
| 4,448,718 A | 5/1984 | Yannas | 530/356 |
| 4,458,678 A | 7/1984 | Yannas | 602/48 |
| 4,474,752 A | 10/1984 | Haslam | 424/78 |
| 4,505,266 A | 3/1985 | Yannas | 128/898 |
| 4,517,173 A | 5/1985 | Kizawa | 424/435 |
| 4,518,721 A | 5/1985 | Dhabhar | 523/120 |
| 4,522,753 A | 6/1985 | Yannas | 530/356 |
| 4,526,938 A | 7/1985 | Churchill et al. | 525/415 |
| 4,553,545 A | 11/1985 | Maass | 606/198 |
| 4,572,832 A | 2/1986 | Kigasawa | 514/772.1 |
| 4,596,574 A | 6/1986 | Urist | 424/422 |
| 4,600,533 A | 7/1986 | Chu | 530/356 |
| 4,652,441 A | 3/1987 | Okada et al. | 424/497 |
| 4,706,680 A | 11/1987 | Keusch | 600/392 |
| 4,713,243 A | 12/1987 | Schiraldi | 424/676 |
| 4,733,665 A | 3/1988 | Palmaz | 606/108 |
| 4,739,762 A | 4/1988 | Palmaz | 623/1.11 |
| 4,741,872 A | 5/1988 | De Luca | 264/4.7 |
| 4,780,450 A | 10/1988 | Sauk | 514/2 |
| 4,787,900 A | 11/1988 | Yannas | 600/36 |
| 4,800,882 A | 1/1989 | Gianturco | 606/194 |
| 4,801,299 A | 1/1989 | Brendel | 623/1 |
| 4,849,141 A | 7/1989 | Fujioka | 264/207 |
| 4,894,232 A | 1/1990 | Reul | 424/439 |
| 4,900,554 A | 2/1990 | Yanagibashi | 424/448 |
| 4,902,289 A | 2/1990 | Yannas | 623/1.47 |
| 4,907,336 A | 3/1990 | Gianturco | 29/515 |
| 4,915,948 A | 4/1990 | Gallopo | 424/435 |
| 4,917,161 A | 4/1990 | Townend | 131/352 |
| 4,947,840 A | 8/1990 | Yannas | 602/50 |
| 4,955,893 A | 9/1990 | Yannas | 606/154 |
| 4,959,217 A | 9/1990 | Sanders | 424/473 |
| 5,019,372 A | 5/1991 | Folkman | 424/422 |
| 5,035,706 A | 7/1991 | Gianturco et al. | 606/198 |
| 5,037,392 A | 8/1991 | Hillstead | 606/194 |
| 5,041,126 A | 8/1991 | Gianturco | 623/1.15 |
| 5,041,292 A | 8/1991 | Feijen | 424/484 |
| 5,100,669 A | 3/1992 | Hyon et al. | 424/426 |
| 5,102,417 A | 4/1992 | Palmaz | 606/195 |
| 5,137,729 A | 8/1992 | Kuroya | 424/435 |
| 5,147,385 A | 9/1992 | Beck et al. | 128/898 |
| 5,166,187 A | 11/1992 | Collombel | 514/21 |
| 5,188,837 A | 2/1993 | Domb | 424/450 |
| 5,192,802 A | 3/1993 | Rencher | 514/535 |
| 5,282,824 A | 2/1994 | Gianturco | 623/1.13 |
| 5,298,258 A | 3/1994 | Akemi | 424/484 |
| 5,314,915 A | 5/1994 | Rencher | 514/535 |
| 5,316,023 A | 5/1994 | Palmaz et al. | 128/898 |
| 5,324,261 A | 6/1994 | Amundson | 604/103.02 |
| 5,324,775 A | 6/1994 | Ree | 525/54.2 |
| 5,330,768 A | 7/1994 | Park et al. | 424/501 |

(Continued)

FOREIGN PATENT DOCUMENTS

| | | | |
|---|---|---|---|
| CA | 1239755 | 8/1988 | A61F 2/00 |
| CA | 1245527 | 11/1988 | A61M 29/00 |

(Continued)

OTHER PUBLICATIONS

US 5,679,669 A, 10/1997, Colvard (withdrawn)

(Continued)

*Primary Examiner* — H. Sarah Park
(74) *Attorney, Agent, or Firm* — Craige Thompson; Thompson Patent Law; Timothy D. Snowden

(57) ABSTRACT

The present invention relates to biocompatible protein-based particles and their methods of preparation and use. More specifically the present invention relates protein-based particles including protein matrix, spread matrix and/or biocoacervate materials derived from one or more biocompatible purified proteins combined with one or more biocompatible solvents that are used to replace or repair tissue and/or bone in treatments for spinal disc(s), joint(s) (e.g. knee, hip, finger, ankle, elbow, shoulder . . . ) and organ(s) (e.g. bladder, lips, vagina, penis, urethra . . . ). In various embodiments of the present invention the protein-based particles may also include one or more pharmacologically active agents and/or one or more additives.

19 Claims, 23 Drawing Sheets

(22 of 23 Drawing Sheet(s) Filed in Color)

(56) References Cited

U.S. PATENT DOCUMENTS

| | | | | |
|---|---|---|---|---|
| 5,385,606 | A | 1/1995 | Kowanko | 106/156.3 |
| 5,418,222 | A | 5/1995 | Song | 514/21 |
| 5,423,739 | A | 6/1995 | Phipps | 604/20 |
| 5,431,921 | A | 7/1995 | Thombre | 424/424 |
| 5,443,483 | A | 8/1995 | Kirsch | 606/74 |
| 5,447,940 | A | 9/1995 | Harvey | 514/310 |
| 5,487,895 | A | 1/1996 | Dapper | 424/278.1 |
| 5,489,304 | A | 2/1996 | Orgill | 128/898 |
| 5,510,077 | A | 4/1996 | Dinh | 264/485 |
| 5,512,291 | A | 4/1996 | Li | 424/443 |
| 5,518,502 | A | 5/1996 | Kaplan | 600/157 |
| 5,573,934 | A | 11/1996 | Hubbell | 435/177 |
| 5,607,445 | A | 3/1997 | Summers | 623/1.22 |
| 5,642,749 | A | 7/1997 | Perryman | 135/66 |
| 5,665,428 | A | 9/1997 | Cha | 427/213.3 |
| 5,700,478 | A | 9/1997 | Cha | 427/213 |
| 5,676,699 | A | 10/1997 | Gogolewski | 623/16.11 |
| 5,709,683 | A | 1/1998 | Bagby | 606/61 |
| 5,716,411 | A | 2/1998 | Orgill | 435/371 |
| RE35,748 | E | 3/1998 | Luck | 514/2 |
| 5,741,670 | A | 4/1998 | Goetinck | 435/69.1 |
| 5,759,582 | A | 6/1998 | Leong | 424/492 |
| 5,773,019 | A | 6/1998 | Ashton | 424/423 |
| 5,783,214 | A | 7/1998 | Royer | 424/499 |
| 5,834,232 | A | 11/1998 | Bishop | 435/68.1 |
| 5,879,713 | A | 3/1999 | Roth | 424/489 |
| 5,948,427 | A | 9/1999 | Yamamoto | 424/426 |
| 5,981,568 | A | 11/1999 | Kunz | 514/411 |
| 6,004,943 | A | 12/1999 | Shi | 514/44 R |
| 6,074,689 | A | 6/2000 | Luck | 427/2.21 |
| 6,124,273 | A | 9/2000 | Drohan | 514/55 |
| 6,179,834 | B1 | 1/2001 | Buysse | 606/41 |
| 6,210,429 | B1 | 4/2001 | Vardi | 623/1.11 |
| 6,248,110 | B1 | 6/2001 | Reiley | 606/93 |
| 6,287,765 | B1 | 9/2001 | Cubicciotti | 435/6 |
| 6,291,582 | B1 | 9/2001 | Dordick | 525/54.1 |
| 6,342,250 | B1 | 1/2002 | Masters | 424/484 |
| 6,371,988 | B1 | 4/2002 | Pafford | 623/17.11 |
| 6,451,335 | B1* | 9/2002 | Goldenheim et al. | 424/426 |
| 6,654,120 | B2* | 11/2003 | Ban | 356/365 |
| 6,960,452 | B2 | 11/2005 | Hubbell | 435/69.7 |
| 7,141,545 | B2* | 11/2006 | Pike et al. | 514/8.5 |
| 7,662,409 | B2* | 2/2010 | Masters | 424/484 |
| 7,731,981 | B2* | 6/2010 | Trieu et al. | 424/400 |
| 2001/0008636 | A1 | 7/2001 | Yamamoto | 424/426 |
| 2001/0020086 | A1 | 9/2001 | Hubbell | 530/322 |
| 2002/0028243 | A1 | 3/2002 | Masters | 424/484 |
| 2002/0052572 | A1 | 5/2002 | Franco | 623/1.11 |
| 2002/0065553 | A1 | 5/2002 | Weber | 606/1 |
| 2003/0007991 | A1 | 1/2003 | Masters | 424/400 |
| 2003/0028204 | A1 | 2/2003 | Li | 606/152 |
| 2003/0225355 | A1 | 12/2003 | Butler | |
| 2004/0002558 | A1 | 1/2004 | McKay | 623/23 |
| 2005/0147690 | A1* | 7/2005 | Masters et al. | 424/499 |
| 2005/0163817 | A1 | 7/2005 | Masters et al. | |
| 2006/0073207 | A1* | 4/2006 | Masters et al. | 424/488 |
| 2006/0167540 | A1 | 7/2006 | Masters et al. | |
| 2006/0210601 | A1 | 9/2006 | Yunoki | 514/12 |

FOREIGN PATENT DOCUMENTS

| | | | | |
|---|---|---|---|---|
| CA | 2085255 | | 12/1991 | A61F 13/02 |
| CA | 2134997 | | 11/1994 | A61F 2/04 |
| CA | 2171047 | | 3/1996 | A61F 2/06 |
| CA | 2175722 | | 5/1996 | A61F 2/04 |
| CA | 2185740 | | 9/1996 | A61F 2/06 |
| CA | 2192520 | | 12/1996 | A61F 2/06 |
| CA | 2239775 | | 6/1997 | A61K 47/34 |
| CA | 2251129 | | 11/1997 | A61K 9/14 |
| CA | 2290806 | | 12/1998 | A61K 31/74 |
| EP | 0 224 934 | B1 | 6/1987 | A61K 41/00 |
| EP | 0 258 780 | A2 | 8/1987 | C08G 63/66 |
| EP | 0 485 210 | A2 | 5/1992 | A61F 2/10 |
| EP | 0 518 697 | A2 | 12/1992 | A61K 9/70 |
| EP | 0 567 234 | A1 | 3/1993 | A61K 47/42 |
| EP | 0 636 378 | B1 | 7/1994 | A61L 31/00 |
| WO | 93/24150 | A1 | 12/1993 | A61K 47/48 |
| WO | 97/32543 | A1 | 9/1997 | A61F 2/06 |
| WO | 97/32544 | A1 | 9/1997 | A61F 2/06 |
| WO | 97/41803 | A1 | 11/1997 | A61F 2/06 |
| WO | 97/41899 | A1 | 11/1997 | A61K 9/14 |
| WO | 99/32613 | A1 | 7/1999 | C12N 9/98 |
| WO | 99/38546 | A1 | 8/1999 | A61L 29/00 |
| WO | 99/49907 | A1 | 10/1999 | A61L 29/00 |
| WO | 01/19305 | A1 | 3/2001 | A61F 13/00 |
| WO | 0183522 | A2 | 11/2001 | C07K 14/00 |
| WO | 0187267 | A1 | 11/2001 | A61K 9/10 |

OTHER PUBLICATIONS

Brand (Brand, et al., The Mouse Model of Collagen-Induced Arthritis, From: Methods in Molecular Medicine, vol. 102: Autoimmunity: Methods and Protocols (2007), Ed. A. Perl © Humana Press Inc., Totowa, NJ).*

"Collagen", available at http://en.wikipedia.org/wiki/Collagen, accessed Apr. 10, 2015.*

Brand, et al., The Mouse Model of Collagen-Induced Arthritis (2004), Methods in molecular medicine, vol. 102.*

Patent, Petvivo, available at https://petvivo.com/pages/patents, accessed on Jun. 17, 2019.*

AAPS: Annual Meeting & Exposition, *Symposia Abstracts & Biographies*, Boston, MA, Nov. 2, 1997, pp. 25-27.

Abbott, et al., *Vascular Grafts: Characteristics and Routine Selection of Prostheses*, Vascular Surgery, a Comprehensive Review, 5th Edition.

Abstracts, *Eighth International Symposium on Recent Advances in Drug Delivery Systems*, Feb. 24, 1997, Salt Lake City, UT, pp. 36-39, 138-140.

*American Red Cross Open to Partners for New Fibrin Sealant*, Genetic Engineering News, Mar. 1995, p. 30.

Anderson, *Characterization of Silk-like Proteins and Processing for Biomedical Applications*, Protein-Based Materials, 1997, pp. 371-423.

Anderson "Morphology and Primary Crystal Structure of a Silk-like Protein Polymer Synthesized by Genetically Engineered *Escherichia coli* Bacteria", *Biopolymers*, New York, NY, vol. 34, No. 8, Aug. 1, 1994, pp. 1049-1058.

Bradley "Some mechanical property considerations of reconstituted collagen for drug release supports", *Biomaterials, Medical Devices, and Artificial Organs*, 1997, vol. 5, No. 2, pp. 159-175.

Bredenberg et al., "In-vitro evaluation of bioadhesion in particulate systems and possible improvement using interactive mixtures." *Pharmacy and Pharmacology* 2003:55:169-177.

Capello The Biological Production of Protein Polymers and Their Use, *Trends in Biotechnology*, Nov. 1, 1990, vol. 8, No. 11, pp. 309-311.

Cappello "In situ self-assembling protein polymer gel systems for administration, delivery and release of drugs", *Journal of controlled Release, Elsevier*, Amsterdam, NL, vol. 53, No. 1-3, Apr. 30, 1998, pp. 105-117.

Cappello, et al., *Microbial Production of Structural Polymers*, (ed. Mobley), 1994 Carl Hanser Verlag, Munich, pp. 35-92.

Cappello, et al., *Genetic Engineering of Structural Protein Polymers*, Biotechnology Progress, 1990, pp. 198-202.

Cappello, *Protein Engineering for Biomaterials Applications*, Current Opinion in Structural Biology, 1992, 2:582-586.

Caruana, *New Drugs Spur Novel Delivery Systems*, Chemical Engineering Progress, Jul. 1997, pp. 15-19.

Choi, et al. Implantation Biology: The Host Response and Biomedical Devices. *The Effect of Biomaterials on the Host*, CRC Press, Boca Raton 405 pages, 1994. Chapter 3, pp. 39-53.

Chvapil, et al., *Some Chemical and Biological Characteristics of a New Collagen-Polymer* Compound Material*, J. Biomed. Mater. Res. vol. 3, pp. 315-331 (1969).

Davis, et al., *Chemically Cross-Linked Albumin Microspheres for the Controlled Release of Incorporated Rose Bengal After Instramuscular Injection Into Rabbits*, Journal of Controlled Release, 4 (1987) 293-302.

(56) References Cited

OTHER PUBLICATIONS

Dickinson, et al., *Biodegradation of a poly(α-amino acid) hydrogel. I.* In vivo, Journal of Biomedical Materials Research, vol. 15, 577-589 (1981).
Drug Delivery Systems (Program), Feb. 1998, San Francisco.
Dunn, et al., *Biomaterials Used in Orthopaedic Surgery*, Implantation Biology, CRC Press, Boca Raton, 1994, pp. 229-252.
Fernandes, et al., *Regulation of Polymeric Implants for Site-specific Drug Delivery*, Polymeric Site-specific Pharmcotherapy, Chapter 16, pp. 424-441.
Ferrari "Biosynthesis of Protein Polymers", *Protein-Based Materials*, 1997, pp. 37-60.
Ghandehari, et al., *Genetic Engineering of Protein-Based Polymers: Potential in Controlled Drug Delivery*, Pharmaceutical Research, vol. 15, No. 6, 1998, pp. 813-815.
Harvey, *Utilizing Prostheses for Drug Delivery*, Implantation Biology, CRC Press, Boca Raton, 1994, pp. 329-345.
Langer, *1994 Whitaker Lecture: Polymers for Drug Delivery and Tissue Engineering*, Annals of Biomedical Engineering, 1995, vol. 23, pp. 101-111.
Li, et al, *A Novel Biodegradable System Based on Gelatin Nanoparticles and Poly(lactic-co-glycolic acid) Microspheres for Protein and Peptide Drug Delivery*, Journal of Pharmaceutical Sciences, vol. 86, No. 8, Aug. 1997, p. 891-895.
Masters, et al., *Liposphere Local Anesthetic Timed-Release for Perineural Site Application*, Pharmaceutical Research, vol. 15, No. 7, 1998, pp. 1038-1045.
Masters, et al., *Sustained Local Anesthetic Relapse from Bioerodible Polymer Matrices: A Potential Method for Prolonged Regional Anesthesia*, Pharmaceutical Research, vol. 10, No. 10, 1993, pp. 1527-1532.
Dutton, *Tissue Engineering: Continued Growth Expected as New Techniques Evolve*, Genetic Engineering News, Apr. 1998, pp. 21, 37.
Kelly, *Researchers Advancing Biopolymer Systems as Vehicles for Delivering Drugs*, Genetic Engineering News, May 15, 1997, pp. 1, 25, 32, 35, 36, 41.
Lewis, *New Directions in Research on Blood Substitutes*, Genetic Engineering News, Jun. 15, 1997, pp. 1, 10, 12, 20, 26, 33, 35, 36, 41.
Masters, Course Syllabus for Mayo Graduate Course, *Polymeric Site-Specific Drug Delivery*, Apr. 1998.
Masters, et al., *Prolonged Regional Nerve Blockade by Controlled Release of Local Anesthetic from a Biodegradable Polymer Matrix*, Anesthesiology, vol. 79, No. 2, 1993, pp. 340-346.
Masters, *Drug Delivery to Peripheral Nerves*, Polymeric Site-Specific Pharmacotherapy, 1994, pp. 443-455.
Mellon et al., "Water Adsorption of Proteins. IV. Effect of Physical Structure." *Journal of the American Chemical Society* 1949:71;2761-2764.
Morrione; "The Formation of Collagen Fibers by the Action of Heparin on Soluble Collagen: An Electron Microscope Study"; 1952; *J. Exg. Med.*; 96(2): 107-14.
Morrow, *Companies to Take Broad Range of Approaches to Develop Rheumatoid Arthritis Therapies*, Genetic Engineering News, Jan. 15, 1997, pp. 1, 7, 9, 24.
Nomura, et al.; "Preparation and Some Properties of Type I Collagen from Fish Scales"; 1996; *Biosci. Biotech. Biochem.*; 60(12): 2092-2094.
Ohtani, *Three-Dimensional Organization of the Collagen Fibrillar Framework of the Human and Rat Livers*, Arch. Hist. Cytol., vol. 51, No. 5, 1988, pp. 473-788.
Peppas, et al. *New Challenges in Biomaterials*, Science, Mar. 1994, vol. 263, pp. 1715-1720.
Polymeric Materials Encyclopedia. Salamone, J.C. (editor), 1996, *CRC Press.* (see p. 7451).
Pramik, *Drug Delivery Firms Focus on Controlled Release Techniques*, Genetic Engineering News, Oct. 1, 1996, pp. 1, 38, 40.

Pramik, *Positive Clinical Results in Pulmonary Drug Delivery: Inhaled Insulin Effective as Infected Drug*, Genetic Engineering News, Jul. 1998, vol. 18, No. 13, pp. 1, 12, 35, 46.
Protein Polymer Technologies: 1994 Annual Report, *BioEngineered Tissue Repair and Regeneration*.
Puri et al., "Adjuvancy enhancement of muramyl dipeptide by modulatin its release from a physico-chemically modified matrix of ovalbumin micorpsheres I. In vitro characterization." *Journal of Controlled Release* 2000:69;63-67.
R&D, A Cahners Publication, *BioDerived Materials*, Jun. 1990, p. 58.
Ranade, *Drug Delivery Systems: 3A. Role of Polymers in Drug Delivery*, J.Clin. Pharmacol 1990; 30: 10-23.
Ranade, *Drug Delivery Systems: 3A. Role of Polymers in Drug Delivery*, J.Clin. Pharmacol 1990; 30: 107-120.
Sammi Gelatin; http://sammi-getalin.com/em2.html; 2003; accessed online Jul. 20, 2009.
Sedlak, *Hyal Pharmaceutical Looks for Home Run with HIT Drug Delivery System*, Genetic Engineering News, Sep. 1, 1995, p. 16.
Sedlak, *Signal Transduction Companies Moving Some Products to the Clinical Testing Environment*, Genetic Engineering News, Mar. 15, 1997, vol. 17, No. 6, pp. 1, 27, 36.
Skarda, et al., *Biodegradable Hydrogel for Controlled Release of Biologically Active Macromolecules*, Journal of Bioactive and Compatible Polymers, vol. 8, Jan. 1993, pp. 24-40.
*Tissue Engineering*, Genetic Engineering News, Jan. 1998, pp. 33.
Urry, et al., *Protein-Based Materials with a Profound Range of Properties and Applications: The Elastin $\Delta T_t$ Hydrophobic Paradigm*, Protein-Based Materials, 1997, pp. 133-177.
Http://www.merriam-webster.com/dictionary/binding (accessed Jan. 24, 2009).
Lijuan Chen et al., "Oral Administration of Shark Type II Collagen Suppresses Complete Freund's Adjuvant-Induced Rheumatoid Arthritis in Rats", *Pharmaceuticals*, Mar. 28, 2012, pp. 339-352.
L. Stefan Lohmander et al., "The Release of Crosslinked Peptides From Type II Collagen Into Human Synovial Fluid Is Increased Soon After Joint Injury and in Osteoarthritis", *Arthritis & Rheumatism*, vol. 48, No. 11, Nov. 2003, pp. 3130-3139.
Katsuyuki Fujii et al., "Rheumatoid arthritis: A synovial disease?", *Annals of the Rheumatic Diseases*, vol. 58 (12): 727, 1999, 4 pages.
Sofia E. Magnusson et al., "Amelioration of collagen-induced arthritis by human recombinant soluble FcγRIIb", *Clinical Immunology*, Feb. 5, 2008, vol. 127, pp. 225-233.
J. Menzel et al., "Demonstration of antibodies to collagen and of collagen-anticollagen immune complexes in rheumatoid arthritis synovial fluids", *Annals of the Rheumatic Diseases*, 1976, pp. 446-450.
Canadian Office Action dated Jul. 14, 2014 for Canadian Application No. 2,711,001 filed Dec. 26, 2008, 3 pages.
Communication dated Jul. 14, 2015 for EP Application No. 08866660.7 filed Dec. 26, 2008, 5 pages.
Office Action dated Nov. 9, 2016 for Australian Application No. 2016201897, 3 pages.
Alini, M. et al.: "The Potential and Limitations of A Cell-Seeded Collagen/Hyaluronan Scaffold to Engineer An Intervertebral Disc-Like Matrix", Spine, vol. 28, No. 5, Mar. 1, 2003, 9 pages.
Lefebvre F. et al.: "New preparation and microstructure of the EndoPatch elastin-collagen containing glycosaminoglycans," Biomaterials Elsevier Science Publishers BV., Barking, GB, vol. 17, No. 18, Sep. 1, 1996, pp. 1813-1818.
Zhong Shaoping et al.: "Formation of collagen-glycosaminoglycan blended nanofibrous scaffolds and their biological properties," Biomacromocolecules, vol. 6, No. 6, Nov. 2005, pp. 2998-3004.
Daamen W. F. et al.: "Preparation and evaluation of molecularly-defined collagen-elastin-glycosaminoglycan scaffolds for tissue engineering," Biomaterials, Elsevier Science Publishers BV., Barking, GB, vol. 24, No. 22,Oct. 1, 2003,pp. 4001-4009.
Lee J. E. et al.: "Effects of the controlled-released TGF-beta1 from chitosan microspheres on chondrocytes cultured in a collagen/chitosan/glycosam inoglycan scaffold," Biomaterials, Elsevier Science Publishers BV., Barking, GB, vol. 25, No. 18, Aug. 1, 2004, pp. 4163-4173.

(56) References Cited

OTHER PUBLICATIONS

Evans, Christopher H. et al., "The Wear Particles of Synovial Fluid: Their Ferrographic Analysis and Pathophysiological Significance", Fall 1981, 14 pages, Bulletin of prosthetics research 10-36:13-26.
Author Unknown, PetVivo's Kush Continues to Demonstrate Effectiveness, CNBC.com [online], Sep. 23, 2016 [retrieved on Sep. 30, 2018]. Retrieved from the Internet: <URL: https://www.cnbc.com/2016/09/23/globe-newswire-petvivoas-kush-continues-to-demonstrate-effectiveness.html>.
PetVivo Inc., Case Studies for Canines, Petvivo.com [online], Jul. 2018 [retrieved on Aug. 1, 2018]. Retrieved from the Internet: <URL: https://petvivo.com/pages/case-studies-canine>.
Larson DVM, Michael J., Case Study—Kona Larson, Petvivo.com [online], Jul. 2018 [retrieved on Aug. 1, 2018]. Retrieved from the Internet: <URL: https://petvivo.com/pages/case-study-kona-larson>.
Sterns DVM, Michael J., Case Study—Bruce Sterns, Petvivo.com [online], Jul. 2018 [retrieved on Aug. 1, 2018]. Retrieved from the Internet: <URL: https://petvivo.com/pages/case study-bruce-sterns>.
Author Unknown, Case Study—Bella Geiselhart, Petvivo.com [online], Jul. 2018 [retrieved on Aug. 1, 2018]. Retrieved from the Internet: <URL: https://petvivo.com/pages/case-study-bella-geiselhart>.
Author Unknown, Case Study—Bailey Chaput, Petvivo.com [online], Jul. 2018 [retrieved on Aug. 1, 2018]. Retrieved from the Internet: <URL: https://petvivo.com/pages/case-study-bailey-chaput>.
Barnett, Brian T., Case Studies—Brian Barnett, DVM, Petvivo.com [online], Jul. 2018 [retrieved on Aug. 1, 2018]. Retrieved from the Internet: <URL: https://petvivo.com/pages/case-study-brian-barnett>.
Kato, F., Nomura M., and Nakamura K., Arthritis in mice induced by a single immunisation with collagen. Annals of the Rheumatic Diseases, Aug. 1996, pp. 535-539 [online], [retrieved on Jul. 29, 2018]. Retrieved from the Internet: <URL: https://ard.bmj.com/content/annrheumdis/55/8/535.full.pdf>.
Williams R.O. (2004) Collagen-Induced Arthritis as a Model for Rheumatoid Arthritis. In: Corti A., Ghezzi P. (eds) Tumor Necrosis Factor. Methods in Molecular Medicine™, vol. 98. Humana Press.
Brand, David D., Latham, Kary A., and Rosloniec, Edward F., Collagen-induced arthritis. Nature Protocols [online], May 2007 [retrieved on Jul. 29, 2018]. Retrieved from the Internet: <URL: https://www.nature.com/articles/hprot.2007.173.pdf>.
Holmdahl, R., Bockerman, R., Backlund, J., and Yamada, H., The molecular pathogenesis of collagen-induced arthritis in mice—a model for rheumatoid arthritis. Ageing Research Reviews, vol. 1, Issue 1, Feb. 2002, pp. 135-147 [online], [retrieved on Jul. 29, 2018]. Retrieved from the Internet: <URL: https://www.ncbi.nlm.nih.gov/pubmed/12039453>.
Chondrex, Inc., Protocol for the Successful Induction of Collagen-Induced Arthritis (CIA) in Mice. Collagen Induced Arthritis, [online], 2017, [retrieved on Jul. 29, 2018]. Retrieved from the Internet: <URL: http://www.chondrex.com/documents/Mouse%20CIA.pdf>.
Veterinary Package Insert, n.d., 2 pages, United States.
David B. Masters, Particles for Osteoarthritis Treatment: Injected Wet Particulate of Collagen-Elastin-Glycosaminoglycan Matrix into Synovial Fluid, Mechanically Cushion Joint with Long Duration, n.d. [online], [retrieved on May 31, 2019]. Retrieved from the Internet <http://abstracts.biomaterials.org/data/papers/2017/abstracts/0140.pdf>.
Section 4: MHB Particles in Synovial Fluid Act as Artificial Cartilage, MasterGel Hydrophilic Biomaterial (MHB), n.d., pp. 16-20, 5 pages, United States.
Petvivo's Dr. Masters Receives Award From Society for Biomaterials, Accesswire, Jul. 6, 2017 [online], [retrieved on May 31, 2019]. Retrieved from the Internet <https://www.accesswire.com/467504/Petvivos-Dr-Masters-Receives-Awa>.

\* cited by examiner

BIOCOMPATIBLE PROTEIN-BASED PARTICLES AND METHODS THEREOF

CROSS-REFERENCE TO RELATED APPLICATION

This application claims priority to and incorporates by reference the entire contents of U.S. Provisional Application Ser. No. 61/016,744, filed on Dec. 26, 2007.

FIELD OF THE INVENTION

The present invention relates to biocompatible protein-based particles and their methods of preparation and use. More specifically the present invention relates protein-based particles including protein matrix, spread matrix and/or biocoacervate materials derived from one or more biocompatible purified proteins combined with one or more biocompatible solvents that are used to replace or repair tissue and/or bone in treatments for spinal disc(s), joint(s) (e.g. knee, hip, finger, ankle, elbow, shoulder . . . ) and organ(s) (e.g. bladder, lips, throat, vagina, penis, urethra . . . ). In various embodiments of the present invention the protein-based particles may also include one or more pharmacologically active agents and/or one or more additives.

BACKGROUND OF THE INVENTION

Protein materials are generally present in the tissues of many biological species. Therefore, the development of medical devices that utilize protein materials, which mimic and/or are biocompatible with the host tissue, have been pursued as desirable devices due to their acceptance and incorporation into such tissue. For example the utilization of protein materials to prepare drug delivery devices, tissue grafts, wound healing and other types of medical devices have been perceived as being valuable products due to their potential biocompatibility.

The use of dried protein, gelatins and/or hydrogels have previously been used as components for the preparation of devices for drug delivery, wound healing, tissue repair, medical device coating and the like. However, many of these previously developed devices do not offer sufficient strength, stability and support when administered to tissue environments that contain high solvent content, such as the tissue environment of the human body. Furthermore, the features of such medical devices that additionally incorporated pharmacologically active agents often provided an ineffective and uncontrollable release of such agents, thereby not providing an optimal device for controlled drug delivery.

A concern and disadvantage of such devices is the rapid dissolving or degradation of the device upon entry into an aqueous or high solvent environment. For example, gelatins and compressed dry proteins tend to rapidly disintegrate and/or lose their form when placed in an aqueous environment. Therefore, many dried or gelatin type devices do not provide optimal drug delivery and/or structural and durability characteristics. Also, gelatins often contain large amounts of water or other liquid that makes the structure fragile, non-rigid and unstable. Alternatively, dried protein devices are often very rigid, tend to be brittle and are extremely susceptible to disintegration upon contact with solvents. It is also noted that the proteins of gelatins usually denature during preparation caused by heating, the gelation process and/or crosslinking procedures, thereby reducing or eliminating the beneficial characteristics of the protein. The deficiencies gelatins and dried matrices have with regards to rapid degradation and structure make such devices less than optimal for the controlled release of pharmacologically active agents, or for operating as the structural scaffolding for devices such as vessels, stents or wound healing implants.

Hydrogel-forming polymeric materials, in particular, have been found to be useful in the formulation of medical devices, such as drug delivery devices. See, e.g., Lee, *J. Controlled Release,* 2, 277 (1985). Hydrogel-forming polymers are polymers that are capable of absorbing a substantial amount of water to form elastic or inelastic gels. Many non-toxic hydrogel-forming polymers are known and are easy to formulate. Furthermore, medical devices incorporating hydrogel-forming polymers offer the flexibility of being capable of being implantable in liquid or gelled form. Once implanted, the hydrogel forming polymer absorbs water and swells. The release of a pharmacologically active agent incorporated into the device takes place through this gelled matrix via a diffusion mechanism.

However, many hydrogels, although biocompatible, are not biodegradable or are not capable of being remodeled and incorporated into the host tissue. Furthermore, most medical devices comprising of hydrogels require the use of undesirable organic solvents for their manufacture. Residual amounts of such solvents could potentially remain in the medical device, where they could cause solvent-induced toxicity in surrounding tissues or cause structural or pharmacological degradation to the pharmacologically active agents incorporated within the medical device. Finally, implanted medical devices that incorporate pharmacologically active agents in general, and such implanted medical devices comprising hydrogel-forming polymers in particular, oftentimes provide suboptimal release characteristics of the drug(s) incorporated therein. That is, typically, the release of pharmacologically active agents from an implanted medical device that includes pharmacologically active agent(s) is irregular, e.g., there is an initial burst period when the drug is released primarily from the surface of the device, followed by a second period during which little or no drug is released, and a third period during which most of the remainder of the drug is released or alternatively, the drug is released in one large burst.

Also, particles made from decellularized tissue, such as human, bovine or porcine tissue, have also been utilized in various medical applications. These decellularized tissue particles have been utilized in various applications as subcutaneous tissue fill materials. Furthermore, these substances have been shown to have some biocompatible properties, but generally are difficult to work with due to the already established matrix present in such materials. Furthermore, such tissue related materials are not conducive to the homogenous distribution of pharmacologically active agents within their matrix structure.

Additionally, other polymeric materials, such as polyvinyl pyrrolidone, polyvinyl alcohols, polyurethanes, polytetrafluoroethylene (PTFE), polypolyvinyl ethers, polyvinylidene halides, polyacrylonitrile, polyvinyl ketones; polyvinyl aromatics, ethylene-methyl methacrylate copolymers, polyamides, polycarbonates, polyoxymethylenes, polyimides, polyethers and other polymeric materials may be utilized as coatings for medical devices, drug delivery devices, tissue fillers or grafts, sutures and for other medical applications. These materials possess some biocompatible attributes, but are limited by their capacity to be non-thrombogenic, to be non-inflammatory, to allow direct cell integration, to deliver therapeutic agents, to allow regeneration of host tissue into the graft and/or to allow other graft materials to adhere to their surface.

SUMMARY OF THE INVENTION

In various embodiments of the present invention, the protein particles may be produced from a protein matrix material or a spread matrix material. Generally the protein matrix materials and spread matrix materials include one or more biocompatible proteins and one or more biocompatible solvents that are prepared at the proper composition to form a cohesive body. The cohesive body is next solidified into a compressed or spread matrix and processed into the particles of the present invention. Furthermore, embodiments of the protein particles of the present invention may also include one or more therapeutic pharmacologically active agents that are homogenously dispersed throughout each protein particle. Various embodiments of the protein particles of the present invention may also include a homogenous distribution of the protein, solvent and other additives, as well as the homogenous distribution of the pharmacologically active agents, to provide desired characteristics, such as drug elution control, durability, elasticity, strength, tissue interaction with cells and extracellular matrix, and the like.

In additional embodiments of the present invention, the protein particles comprise one or more protein biocoacervates and/or related biomaterials derived from the biocoacervates. The biocoacervates or related biomaterials are generally amorphous materials that are precipitated from solution and comprise one or more biocompatible primary proteins (e.g. collagen), one or more glycosaminoglycans (e.g. heparin, hyaluronic acid, chondroitin sulfate . . . ) and one or more biocompatible solvents (e.g. water). It is noted that the term glycosaminoglycan may also be considered to include mucopolysaccharides and proteoglycans. Additionally, the biocoacervates and/or biomaterials may also include one or more secondary proteins (e.g. elastin), one or more pharmacologically active agents and/or one or more additive materials to provide a therapeutic entity or enhance the chemical and/or mechanical properties or encourage the tissue interaction with cells and extracellular matrix of the protein-based materials such as the biocoacervate or biomaterials using the biocoacervates.

The biocompatible protein particles of the present invention are designed to retain the protein's natural activity combined with the ability to form it into various sized particles with structural integrity. The protein particles are further designed to compatibly mimic the host tissue composition and/or promote the remodeling of the particles into an architectural framework to support natural tissue growth. Generally, the protein particles of the present invention are biocompatible, biodegradable, and/or biointegratable thereby allowing the integration and remodeling of the particulate material by the host tissue. In addition to the ability to act as a structural scaffold, the ability to customize the material properties to the application, to mold the particles into any defined shape, and to incorporate other substances such as pharmacologically active agents (drugs), or other structural materials, into the protein particles also make the particles unique.

The present invention further includes methods of treating, enhancing and repairing the structure and/or function of organs, spinal discs and joints by administering the particles disclosed or suggested herein.

The foregoing and additional advantages and characterizing features of the present invention will become increasingly apparent to those of ordinary skill in the art by references to the following detailed description and to the drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
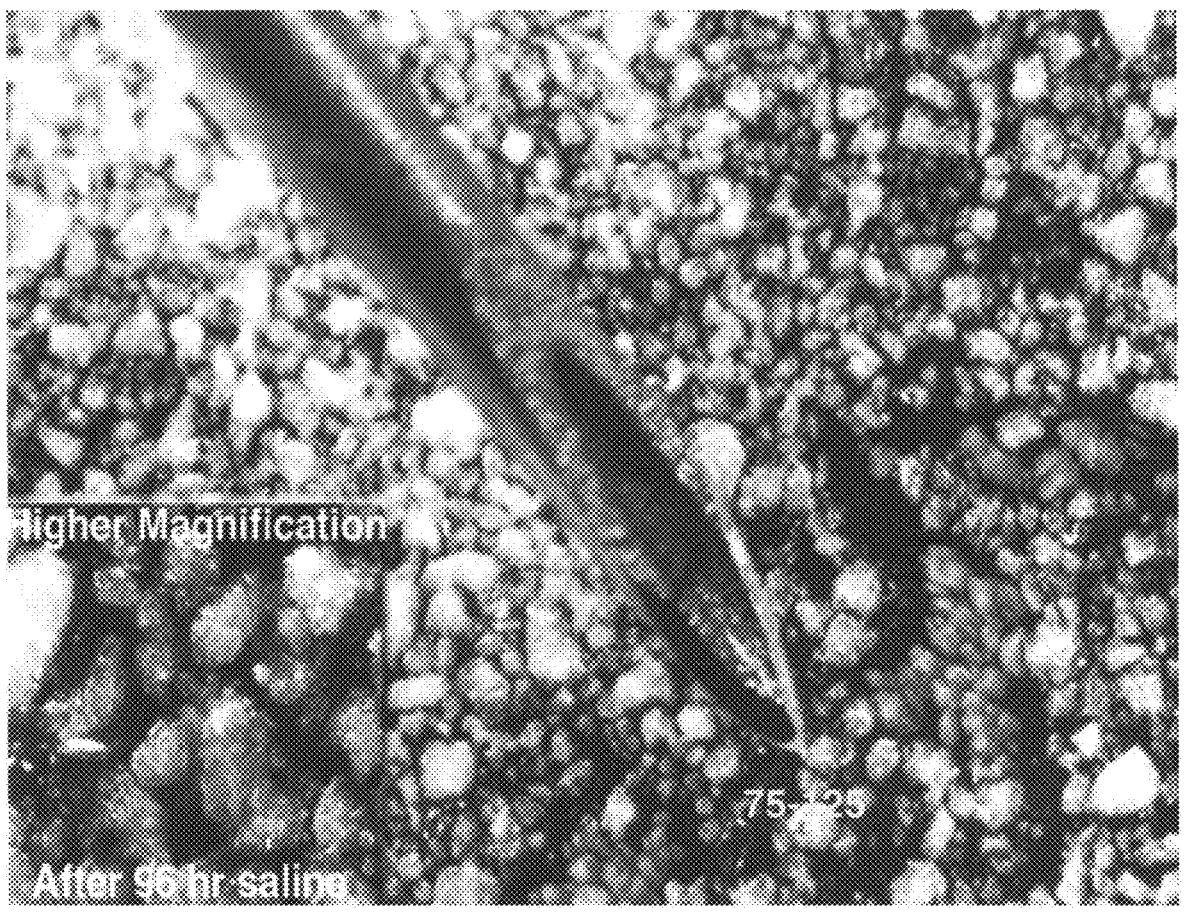
FIG. 1 depicts another embodiment of the particles of the present invention wherein the particles are porous.

The embodiments of the invention described below are not intended to be exhaustive or to limit the invention to the precise forms disclosed in the following detailed description. Rather, the embodiments are chosen and described so that others skilled in the art may appreciate and understand the components, principles and practices of the present invention.

The biocompatible protein particles of the present invention are generally produced from one or more protein-based materials. The protein-based materials utilized to make the particles of the present invention include protein matrix materials, spread matrix materials and/or biocoacervates and biomaterials including the biocoacervates. Each of the protein-based material used to make the particles of the present invention comprise one or more biocompatible purified proteins and one or more biocompatible solvents. In various embodiments of the present invention, the protein particles may also include one or more pharmacologically active agents. It is noted that additional additive materials, such as biocompatible polymers like polyanhydride, polylactic acid, polyurethane and the like, and/or therapeutic entities may be included in the material to provide various beneficial features such as strength, elasticity, structure, enhanced biocompatibility and/or any other desirable characteristics. In various embodiments of the present invention, the particles possess a relatively homogeneous distribution of the components, including a homogenous distribution of any pharmacologically active agents and additive materials.

As previously mentioned, the protein-based materials and the biocompatible protein particles generally comprise one or more biocompatible purified synthetic proteins, genetically-engineered proteins, natural proteins or any combination thereof. In a number of the embodiments of the present invention, the particles comprise a water-absorbing, biocompatible purified protein. The utilization of a water-absorbing biocompatible purified protein provides the advantage that, not only will the biocompatible protein particles be bioresorbable, but may remodel to mimic and support the tissue it contacts. That is, the metabolites of any degradation and/or resorption of the water-absorbing biocompatible purified protein may be reused by the patient's body rather than excreted.

Additionally, the proteins of the present invention are generally purified and in a free-form state. Normally, purified proteins are comprised of protein molecules that are not substantially crosslinked to other protein molecules, unlike tissues or gelatins. Normally, tissue or gelatin is already in a crosslinked matrix form and is thereby limited in forming new intermolecular or intramolecular bonds. Therefore, the purified protein molecules when added to solvent have the capacity to freely associate or intermingle with each other and other molecules or particles, such as solvents or pharmacologically active agents to form a homogeneous structure. Additionally, the binding sites of the purified free-form proteins for the attraction and retention of solvent, drug, protein or other molecules are generally available for binding whereas proteins derived from tissues and gelatins have generally lost some or most of its binding capability.

As previously suggested, the biocompatible purified protein utilized may either be naturally occurring, synthetic or genetically engineered. Various embodiments of the present invention include insoluble naturally occurring purified protein. Naturally occurring purified protein that may be utilized in the protein particles of the present invention include, but are not limited to elastin, collagen, albumin, ovalbumin, keratin, fibronectin, vitronectin, laminin, thrombospondin, silk, silk fibroin, actin, myosin, fibrinogen, thrombin, aprotinin, antithrombin III, active proteins (e.g. interleukin, interferon, bone morphogenic protein (BMP) and the like), and any other biocompatible purified natural protein. Examples of purified proteins that are commercially available and may be utilized in some embodiments of the present invention include insoluble collagen (e.g. bovine, porcine, human . . . ) and insoluble elastin, manufactured by Kensey Nash Corporation, 55 East Uwchlan Avenue, Exton, PA 19341, Sigma-Aldrich Corporation, St. Louis, MO, USA or Elastin Products Company, Inc., P.O. Box 568, Owensville, MO, USA 65066. Other embodiments of the present invention may include soluble proteins. Examples of such soluble proteins include, but are not limited to soluble collagen (e.g. bovine, procine, human . . . ), soluble elastin, and soluble albumen manufactured by Kensey Nash Corporation, 55 East Uwchlan Avenue, Exton, PA 19341, Sigma-Aldrich Corporation, St. Louis, MO, USA or Elastin Products Company, Inc., P.O. Box 568, Owensville, Missouri, USA 65066. It is noted that combinations of purified natural proteins may be utilized to optimize desirable characteristics of the resulting biomatrix materials, such as strength, swelling, integration, cellular remodeling, degradability, resorption, drug absorption, etc. Inasmuch as heterogeneity in molecular weight, sequence and stereochemistry can influence the function of a protein in a biomatrix material, in some embodiments of the present invention synthetic or genetically engineered proteins are preferred in that a higher degree of control can be exercised over these parameters.

As previously suggested the proteins of the present invention are generally purified proteins. The purity of each natural protein component mixed in the coatable composition phase (the coatable composition will be described further below) during production of particles include 20% or less other proteins or impurities, preferably 10% or less other proteins or impurities, more preferably 3% or less other proteins or impurities and if available ideally 1% or less other proteins or impurities.

Synthetic proteins are generally prepared by chemical synthesis utilizing techniques known in the art. Also, individual proteins may be chemically combined with one or more other proteins of the same or different type to produce a dimer, trimer or other multimer. A simple advantage of having a larger protein molecule is that it will make interconnections with other protein molecules to create a stronger biomatrix material that is less susceptible to dissolving in aqueous solutions and provides additional protein structural and biochemical characteristics.

Additional, protein molecules can also be chemically combined to any other chemical so that the chemical does not release from the biocompatible protein particles. In this way, the chemical entity can provide surface modifications to particles or structural contributions to the particles to produce specific characteristics. The surface modifications can enhance and/or facilitate cell attachment depending on the chemical substance or the cell type. The structural modifications can be used to facilitate or impede dissolution, enzymatic degradation, or dissolution of the particulate material.

Synthetic biocompatible purified proteins may be cross-linked, linked, bonded, chemically and/or physically linked to pharmacological active agents, enzymatically, chemically or thermally cleaved and utilized alone or in combination with other biocompatible proteins or partial proteins e.g. peptides, to form the biocompatible particles. Examples of such synthetic biocompatible proteins include, but are not limited to heparin-protein, heparin-protein-polymer, heparan sulfate-protein, heparan sulfate-polymer, heparan sulfate proteoglycans-protein, heparan sulfate proteoglycans-polymer, heparan sulfate-protein-polymer, chondroitin-protein, chondroitin-polymer, chondroitin-protein-polymer, chondroitin sulfate-protein, chondroitin sulfate-polymer, chondroitin sulfate-protein-polymer, heparan sulfate proteoglycans-cellulose, heparan sulfate proteoglycans-alginate, heparan sulfate proteoglycans-polylactide, GAGs-collagen, heparin-collagen, collagen-elastin-heparin, collagen-albumin, collagen-albumin-heparin, collagen-albumin-elastin-heparin, collagen-hyaluronic acid, collagen-chondroitin-heparin, collagen-chondroitin, derivatives thereof and the like.

A specific example of a particularly preferred genetically engineered protein for use in the biocompatible protein particles of the present invention is human collagen produced by FibroGen, Inc., 225 Gateway Blvd., South San Francisco, CA 94080. Other examples of particularly preferred genetically engineered proteins for use in the biocompatible protein particles of the present invention are commercially available under the nomenclature "ELP", "SLP", "CLP", "SLPL", "SLPF" and "SELP" from Protein Polymer Technologies, Inc. San Diego, CA ELP's, SLP's, CLP's, SLPL's, SLPF's and SELP's are families of genetically engineered protein polymers consisting of silklike blocks, elastinlike blocks, collagenlike blocks, lamininlike blocks, fibronectinlike blocks and the combination of silklike and elastinlike blocks, respectively. The ELP's, SLP's, CLP's, SLPL's, SLPF's and SELP's are produced in various block lengths and compositional ratios. Generally, blocks include groups of repeating amino acids making up a peptide sequence that occurs in a protein. Genetically engineered proteins are qualitatively distinguished from sequential polypeptides found in nature in that the length of their block repeats can be greater (up to several hundred amino acids versus less than ten for sequential polypeptides) and the sequence of their block repeats can be almost infinitely complex. A further description of genetically engineered blocks may be found in Franco A. Ferrari and Joseph Cappello, *Biosynthesis of Protein Polymers*, in: Protein-Based Materials, (eds., Kevin McGrath and David Kaplan), Chapter 2, pp. 37-60, Birkhauser, Boston (1997).

The nature of the elastinlike blocks, and their length and position within the monomers influences the water solubility of the SELP polymers. For example, decreasing the length and/or content of the silklike block domains, while maintaining the length of the elastinlike block domains, increases the water solubility of the polymers. For a more detailed discussion of the production of SLP's, ELP's, CLP's, SLPF's and SELP's as well as their properties and characteristics see, for example, in J. Cappello et al., *Biotechnol. Prog.*, 6, 198 (1990), the full disclosure of which is incorporated by reference herein. One preferred SELP, SELP7, has an elastin:silk ratio of 1.33, and has 45% silklike protein material and is believed to have weight average molecular weight of 80,338.

The biocoacervates and biomaterials that include the biocoacervates normally comprise one or more biocompatible primary proteins and, in various embodiments, one or more secondary proteins. The primary and secondary proteins are generally soluble or are solubilized (i.e. processed to substantially dissolve in solution) prior to formation of the biocoacervate. Primary proteins normally have an affinity to bind with glycosaminoglycans and, in some instances, other proteins thereby indicating that functional groups are present on the primary proteins that attract and retain the glycosaminoglycans and possibly other proteins. Additionally, primary proteins when mixed with glycosaminoglycans in solution under proper conditions will generally form a precipitate that falls out of solution, whereas the secondary proteins will not form such a precipitate when placed in solution with glycosaminoglycans.

Additionally, secondary proteins generally have a more limited binding affinity with glycosaminoglycans than their primary protein counterparts, but are attracted and retained by the primary proteins in the presence of glycosaminoglycans. However, secondary proteins have been found to add very beneficial characteristics to the biocoacervates of the present invention, such as elasticity, strength, biodurability, biocompatibility and the like.

Generally, the amount of primary protein found in embodiments of the biocoacervate or biomaterials of the present invention may vary between from about 5% to about 90%, in various embodiments from about 20% to 80% by weight, and in other embodiments from about 25% to 70% by weight based upon the weight of the final biocoacervate or biomaterial. Alternatively, the amount of secondary protein may vary between from about 0% to about 40%, in various embodiments from about 2% to 30% by weight, and in additional embodiments from about 5% to 25% by weight based upon the weight of the final biocoacervate or biomaterial.

Similar to other embodiments of the present invention, the primary and secondary proteins utilized in the present invention may be synthetic proteins, genetically-engineered proteins, natural proteins or any combination thereof. In many embodiments of the present invention, the biocoacervates, biomaterials and the related devices include water absorbing, biocompatible primary and secondary proteins. The utilization of a water absorbing biocompatible protein included in the protein based materials such as the biocoacervate or biomaterial, provides the advantage that, not only will the protein based materials be bioresorbable, but may remodel to mimic and support the tissue it contacts and may enhance the tissue response by recruiting cells that heal and rejuvenate. That is, the metabolites of any degradation and/or resorption of the water absorbing biocompatible protein may be reused by the patient's body rather than excreted.

Additionally, the primary and secondary proteins of the present invention are generally purified and in a free-form state. Normally, free-form proteins are comprised of protein molecules that are not substantially crosslinked to other protein molecules, unlike tissues (e.g. decellularized tissue) or gelatins. Normally, tissue or gelatin is already in a crosslinked matrix form and is thereby limited in forming new intermolecular or intramolecular bonds. Therefore, the free-form protein molecules when added to solvent have the capacity to freely associate or intermingle with each other and other molecules or particles, such as solvents, pharmacologically active agents, additives and other proteins to form a homogeneous structure. Additionally, the binding sites of the free-form primary proteins for the attraction and retention of glycosaminoglycans or secondary proteins are generally available for binding whereas proteins derived from tissues and gelatins have generally lost some or most of its binding or interaction capability.

As previously suggested, the primary and secondary proteins utilized may either be naturally occurring, synthetic or genetically engineered. Examples of naturally occurring primary proteins that may be utilized in biocoacervates and biomaterials of the present invention include, but are not limited to the following and their derivatives: collagen, bone morphogenic protein and its isoforms that contain glucosaminoglycan binding sites, albumin, interleukins, epidermal growth factors, fibronectin, laminin, thrombin, aprotinin, antithrombin III and any other biocompatible natural protein that includes glycosaminoglycan binding sites. Naturally occurring secondary proteins that may be utilized in biocoacervates and biomaterials of the present invention include, but are not limited to the following and their derivatives: fibrin, fibrinogen, elastin, albumin, ovalbumin, keratin, silk, silk fibroin, actin, myosin, thrombin, aprotinin, antithrombin III and any other biocompatible natural protein that have an affinity to primary proteins in the presence of glycosaminoglycans. Examples of primary and secondary proteins that are commercially available and may be utilized in some embodiments of the present invention include Type I soluble or insoluble collagen, insoluble or soluble elastin, and soluble albumen manufactured by Kensey Nash Corporation, 55 East Uwchlan Avenue, Exton, PA 19341, Sigma-Aldrich Corporation, St. Louis, MO, USA or Elastin Products Company, Inc., P.O. Box 568, Owensville, MO, USA 65066. It is noted that in various embodiments of the present invention, the insoluble proteins listed above would be processed to a soluble form prior to or during synthesis of a biocoacervate or biomaterial. It is further noted that combinations of natural proteins may be utilized to optimize desirable characteristics of the resulting biocoacervates and biomaterials, such as strength, degradability, resorption, etc. Inasmuch as heterogeneity in molecular weight, sequence and stereochemistry can influence the function of a protein in a biocoacervate or biomaterial, in some embodiments of the present invention synthetic or genetically engineered proteins are preferred in that a higher degree of control can be exercised over these parameters.

Generally, the amount of purified protein found in embodiments of the particles of the present invention may vary between from about 1% to about 99%, in various embodiments from about 2% to 50% by weight, and in additional embodiments from about 2.5% to 20% by weight based upon the weight of the final particles. As used herein, unless stated otherwise, all percentages are percentages based upon the total mass of the composition or particles being described, e.g., 100% is total.

The biocompatible protein particles utilized in various embodiments of the present invention also include one or more biocompatible solvents. Any biocompatible solvent may be utilized in the method and corresponding biomatrix material of the present invention. By using a biocompatible solvent, the risk of adverse tissue reactions to residual solvent remaining in the device after manufacture is minimized. Additionally, the use of a biocompatible solvent reduces the potential structural and/or pharmacological degradation of the pharmacologically active agent that some such pharmacologically active agents undergo when exposed to organic solvents. Suitable biocompatible solvents for use in the method of the present invention include, but are not limited to, water; dimethyl sulfoxide (DMSO); simple biocompatible alcohols, such as methanol and ethanol; various acids, such as formic acid; oils, such as olive oil, peanut oil and the like; ethylene glycol, glycols; and combinations of these and the like. Preferably, the biocompatible solvent comprises water. In production of the compressed protein matrix material and the spread matrix material, the amount of biocompatible solvent utilized in the coatable composition will preferably be that amount sufficient to result in the composition being fluid and flowable enough to be coatable. Generally, the amount of biocompatible solvent suitable for use in the method of manufacturing the compressed matrix or spread matrix materials the present invention will range from about 50% to about 1000%, alternatively from about 100% to about 300% by weight, based upon the weight and/or amount of the protein utilized. Alternatively, the amount of biocompatible solvent utilized in the formation of the biocoacervates or biomaterials utilizing the biocoacervates of present invention will preferably be that amount sufficient to result in the primary and secondary proteins being fluid and flowable enough to allow the protein to enter into solution or dissolve in solution. Generally, the amount of biocompatible solvent suitable for use in the method of the present invention will range from about 100% to about 50,000% by weight, in some embodiments from about 200% to about 10,000% by weight, and in other embodiments from about 300% to about 2000% by weight, based upon the weight and/or amount of the protein utilized.

The biocoacervates and biomaterials utilized in various embodiments of the present invention also include one or more glycosaminoglycans, proteoglycans or mucopolysaccharides. Glycosaminoglycans can be derived or synthesized from any source, including artificial, animal or plant sources. Examples of glycosaminoglycans that are utilized in the coacervates and biomaterials of the present invention include but are not limited to the heparin, heparin sulfate, keratan sulfate, dermatin, dermatin sulfate, heparin-hyaluronic acid, chondroitin, chondroitin sulfate (e.g. chondroitin 6-sulfate and chondroitin 4-sulfate), chitin, chitosan, acetyl-glucosamine, hyaluronic acid, aggrecan, decorin, biglycan, fibromodulin, lumican, combinations, glycosaminoglycan complexes or compounds and the like.

In addition to the biocompatible protein(s), the biocompatible solvent(s) and, when producing the biocoacervates or biomaterials, glycosaminoglycans, the biocompatible protein particles that may be utilized in various embodiments of the present invention may include one or more pharmacologically active agents. As used herein, "pharmacologically active agent" generally refers to a pharmacologically active agent having a direct or indirect beneficial therapeutic effect upon introduction into a host. Pharmacologically active agents further include neutraceuticals. The phrase "pharmacologically active agent" is also meant to indicate prodrug forms thereof. A "prodrug form" of a pharmacologically active agent means a structurally related compound or derivative of the pharmacologically active agent which, when administered to a host is converted into the desired pharmacologically active agent. A prodrug form may have little or none of the desired pharmacological activity exhibited by the pharmacologically active agent to which it is converted. Representative examples of pharmacologically active agents that may be suitable for use in the particles and particle devices of the present invention include, but are not limited to, (grouped by therapeutic class):

Antidiarrheals such as diphenoxylate, loperamide and hyoscyamine;

Antihypertensives such as hydralazine, minoxidil, captopril, enalapril, clonidine, prazosin, debrisoquine, diazoxide, guanethidine, methyldopa, reserpine, trimethaphan;

Calcium channel blockers such as diltiazem, felodipine, amlodipine, nitrendipine, nifedipine and verapamil;

Antiarrhythmics such as amiodarone, flecainide, disopyramide, mexiletene procainamide, and quinidine, Antiangina agents such as glyceryl trinitrate, erythrityl tetranitrate, pentaerythritol tetranitrate, mannitol hexanitrate, perhexilene, isosorbide dinitrate and nicorandil;

Beta-adrenergic blocking agents such as alprenolol, atenolol, bupranolol, carteolol, labetalol, metoprolol, nadolol, nadoxolol, oxprenolol, pindolol, propranolol, sotalol, timolol and timolol maleate;

Cardiotonic glycosides such as digoxin and other cardiac glycosides and theophylline derivatives;

Adrenergic stimulants such as adrenaline, ephedrine, fenoterol, isoprenaline, orciprenaline, rimeterol, salbutamol, salmeterol, terbutaline, dobutamine, phenylephrine, phenylpropanolamine, pseudoephedrine and dopamine;

Vasodilators such as cyclandelate, isoxsuprine, papaverine, dipyrimadole, isosorbide dinitrate, phentolamine, nicotinyl alcohol, co-dergocrine, nicotinic acid, glycerl trinitrate, pentaerythritol tetranitrate and xanthinol;

Antiproliferative agents such as paclitaxel, estradiol, actinomycin D, sirolimus, tacrolimus, everolimus and dexamethasone;

Antimigraine preparations such as ergotanmine, dihydroergotamine, methysergide, pizotifen and sumatriptan;

Anticoagulants and thrombolytic agents such as warfarin, dicoumarol, low molecular weight heparins such as enoxaparin, streptokinase and its active derivatives;

Antiplatelet agent such as clopidogral bisulfate;

Hemostatic agents such as aprotinin, tranexamic acid and protamine;

Analgesics and antipyretics including the opioid analgesics such as buprenorphine, dextromoramide, dextropropoxyphene, fentanyl, alfentanil, sufentanil, hydromorphone, methadone, morphine, oxycodone, papaveretum, pentazocine, pethidine, phenopefidine, codeine dihydrocodeine; acetylsalicylic acid (aspirin), paracetamol, and phenazone;

Immunosuppressants, antiproliferatives and cytostatic agents such as rapomycin (sirolimus) and its analogs (everolimus and tacrolimus);

Neurotoxins such as capsaicin, botulinum toxin (botox);

Hypnotics and sedatives such as the barbiturates amylobarbitone, butobarbitone and pentobarbitone and other hypnotics and sedatives such as chloral hydrate, chlormethiazole, hydroxyzine and meprobamate;

Antianxiety agents such as the benzodiazepines alprazolam, bromazepam, chlordiazepoxide, clobazam, chlorazepate, diazepam, flunitrazepam, flurazepam, lorazepam, nitrazepam, oxazepam, temazepam and triazolam;

Neuroleptic and antipsychotic drugs such as the phenothiazines, chlorpromazine, fluphenazine, pericyazine, perphenazine, promazine, thiopropazate, thioridazine, trifluoperazine; and butyrophenone, droperidol and haloperidol; and other antipsychotic drugs such as pimozide, thiothixene and lithium;

Antidepressants such as the tricyclic antidepressants amitryptyline, clomipramine, desipramine, dothiepin, doxepin, imipramine, nortriptyline, opipramol, protriptyline and trimipramine and the tetracyclic antidepressants such as mianserin and the monoamine oxidase inhibitors such as isocarboxazid, phenelizine, tranylcypromine and moclobemide and selective serotonin re-uptake inhibitors such as fluoxetine, paroxetine, citalopram, fluvoxamine and sertraline;

CNS stimulants such as caffeine and 3-(2-aminobutyl) indole;

Anti-alzheimer's agents such as tacrine;

Anti-Parkinson's agents such as amantadine, benserazide, carbidopa, levodopa, benztropine, biperiden, benzhexol, procyclidine and dopamine-2 agonists such as S(−)-2-(N-propyl-N-2-thienylethylamino)-5-hydroxytetralin (N-0923), Anticonvulsants such as phenytoin, valproic acid, primidone, phenobarbitone, methylphenobarbitone and carbamazepine, ethosuximide, methsuximide, phensuximide, sulthiame and clonazepam, Antiemetics and antinauseants such as the phenothiazines prochloperazine, thiethylperazine and 5HT-3 receptor antagonists such as ondansetron and granisetron, as well as dimenhydrinate, diphenhydramine, metoclopramide, domperidone, hyoscine, hyoscine hydrobromide, hyoscine hydrochloride, clebopride and brompride;

Non-steroidal anti-inflammatory agents including their racemic mixtures or individual enantiomers where applicable, preferably which can be formulated in combination with dermal and/or mucosal penetration enhancers, such as ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol, ketorolac, flufenisal, salsalate, triethanolamine salicylate, aminopyrine, antipyrine, oxyphenbutazone, apazone, cintazone, flufenamic acid, clonixerl, clonixin, meclofenamic acid, flunixin, coichicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, and triflumidate;

Antirheumatoid agents such as penicillamine, aurothioglucose, sodium aurothiomalate, methotrexate and auranofin;

Muscle relaxants such as baclofen, diazepam, cyclobenzaprine hydrochloride, dantrolene, methocarbamol, orphenadrine and quinine;

Agents used in gout and hyperuricaemia such as allopurinol, colchicine, probenecid and sulphinpyrazone;

Oestrogens such as oestradiol, oestriol, oestrone, ethinyloestradiol, mestranol, stilboestrol, dienoestrol, epioestriol, estropipate and zeranol;

Progesterone and other progestagens such as allyloestrenol, dydrgesterone, lynoestrenol, norgestrel, norethyndrel, norethisterone, norethisterone acetate, gestodene, levonorgestrel, medroxyprogesterone and megestrol;

Antiandrogens such as cyproterone acetate and danazol;

Antioestrogens such as tamoxifen and epitiostanol and the aromatase inhibitors, exemestane and 4-hydroxy-androstenedione and its derivatives;

Androgens and anabolic agents such as testosterone, methyltestosterone, clostebol acetate, drostanolone, furazabol, nandrolone oxandrolone, stanozolol, trenbolone acetate, dihydro-testosterone, 17-(α-methyl-19-noriestosterone and fluoxymesterone;

5-alpha reductase inhibitors such as finasteride, turosteride, LY-191704 and MK-306;

Corticosteroids such as betamethasone, betamethasone valerate, cortisone, dexamethasone, dexamethasone 21-phosphate, fludrocortisone, flumethasone, fluocinonide, fluocinonide desonide, fluocinolone, fluocinolone acetonide, fluocortolone, halcinonide, halopredone, hydrocortisone, hydrocortisone 17-valerate, hydrocortisone 17-butyrate, hydrocortisone 21-acetate, methylprednisolone, prednisolone, prednisolone 21-phosphate, prednisone, triamcinolone, triamcinolone acetonide;

Glycosylated proteins, proteoglycans, glycosaminoglycans such as heparin, heparan-sulfate, chondroitin sulfate; chitin, acetyl-glucosamine, hyaluronic acid keratin sulfate and dermatin sulfate;

Complex carbohydrates such as glucans;

Further examples of steroidal anti-inflammatory agents such as cortodoxone, fludroracetonide, fludrocortisone, difluorsone diacetate, flurandrenolone acetonide, medrysone, amcinafel, amcinafide, betamethasone and its other esters, chloroprednisone, clorcortelone, descinolone, desonide, dichlorisone, difluprednate, flucloronide, flumethasone, flunisolide, flucortolone, fluoromethalone, fluperolone, fluprednisolone, meprednisone, methylmeprednisolone, paramethasone, cortisone acetate, hydrocortisone cyclopentylpropionate, cortodoxone, flucetonide, fludrocortisone acetate, flurandrenolone, aincinafal, amcinafide, betamethasone, betamethasone benzoate, chloroprednisone acetate, clocortolone acetate, descinolone acetonide, desoximetasone, dichlorisone acetate, difluprednate, flucloronide, flumethasone pivalate, flunisolide acetate, fluperolone acetate, fluprednisolone valerate, paramethasone acetate, prednisolamate, prednival, triamcinolone hexacetonide, cortivazol, formocortal and nivazol;

Pituitary hormones and their active derivatives or analogs such as corticotrophin, thyrotropin, follicle stimulating hormone (FSH), luteinising hormone (LH) and gonadotrophin releasing hormone (GnRH), growth hormone;

Hypoglycemic agents such as insulin, chlorpropamide, glibenclamide, gliclazide, glipizide, tolazamide, tolbutamide and metformin;

Thyroid hormones such as calcitonin, thyroxine and liothyronine and antithyroid agents such as carbimazole and propylthiouracil;

Other miscellaneous hormone agents such as octreotide;

Pituitary inhibitors such as bromocriptine;

Ovulation inducers such as clomiphene;

Diuretics such as the thiazides, related diuretics and loop diuretics, bendrofluazide, chlorothiazide, chlorthalidone, dopamine, cyclopenthiazide, hydrochlorothiazide, indapamide, mefruside, methycholthiazide, metolazone, quinethazone, bumetanide, ethacrynic acid and frusemide and potasium sparing diuretics, spironolactone, amiloride and triamterene;

Antidiuretics such as desmopressin, lypressin and vasopressin including their active derivatives or analogs;

Obstetric drugs including agents acting on the uterus such as ergometrine, oxytocin and gemeprost;

Prostaglandins such as alprostadil (PGE1), prostacyclin (PGI2), dinoprost (prostaglandin F2-alpha) and misoprostol;

Antimicrobials including the cephalosporins such as cefazolin, cefuroxime, cephalexin, cefoxytin and cephalothin;

Penicillins such as amoxycillin, amoxycillin with clavulanic acid, ampicillin, bacampicillin, benzathine penicillin, benzylpenicillin, carbenicillin, cloxacillin, methicillin, phenethicillin, phenoxymethylpenicillin, flucloxacillin, meziocillin, piperacillin, ticarcillin and azlocillin;

Tetracyclines such as minocycline, chlortetracycline, tetracycline, demeclocycline, doxycycline, methacycline and oxytetracycline and other tetracycline-type antibiotics;

Aminoglycosides such as amikacin, gentamicin, kanamycin, neomycin, netilmicin and tobramycin;

Antifungals such as amorolfine, isoconazole, clotrimazole, econazole, miconazole, nystatin, terbinafine, bifonazole, amphotericin, griseofulvin, ketoconazole, fluconazole and flucytosine, salicylic acid, fezatione, ticlatone, tolnaftate, triacetin, zinc, pyrithione and sodium pyrithione;

Quinolones such as nalidixic acid, cinoxacin, ciprofloxacin, enoxacin and norfloxacin;

Sulphonamides such as phthalysulphthiazole, sulfadoxine, sulphadiazine, sulphamethizole and sulphamethoxazole;

Sulphones such as dapsone;

Other miscellaneous antibiotics such as cyclosporin, chloramphenicol, clindamycin, erythromycin, erythromycin ethyl carbonate, erythromycin estolate, erythromycin glucepate, erythromycin ethylsuccinate, erythromycin lactobionate, roxithromycin, lincomycin, natamycin, nitrofurantoin, spectinomycin, vancomycin, aztreonarn, colistin IV, metronidazole, tinidazole, fusidic acid, trimethoprim, and 2-thiopyridine N-oxide; halogen compounds, particularly iodine and iodine compounds such as iodine-PVP complex and diiodohydroxyquin, hexachlorophene; chlorhexidine; chloroamine compounds; benzoylperoxide and tobramycin;

Antituberculosis drugs such as ethambutol, isoniazid, pyrazinamide, rifampicin and clofaziminine;

Antimalarials such as primaquine, pyrimethamine, chloroquine, hydroxychloroquine, quinine, mefloquine and halofantrine;

Antiviral agents such as acyclovir and acyclovir prodrugs, famcyclovir, zidovudine, didanosine, stavudine, lamivudine, zalcitabine, saquinavir, indinavir, ritonavir, n-docosanol, tromantadine and idoxuridine;

Anthelmintics such as mebendazole, thiabendazole, niclosamide, praziquantel, pyrantel embonate and diethylcarbamazine;

Cytotoxic agents such as plicamycin, cyclophosphamide, dacarbazine, fluorouracil and its prodrugs (described, for example, in *International Journal of Pharmaceutics*, 111, 223-233 (1994)), methotrexate, procarbazine, 6-mercaptopurine and mucophenolic acid;

Anorectic and weight reducing agents including dexfenflurarnine, fenfluramine, diethylpropion, mazindol and phentermine;

Agents used in hypercalcaemia such as calcitriol, dihydrotachysterol and their active derivatives or analogs;

Antitussives such as ethylmorphine, dextromethorphan and pholcodine;

Expectorants such as carbolcysteine, bromhexine, emetine, quanifesin, ipecacuanha and saponins;

Decongestants such as phenylephrine, phenylpropanolamine and pseudoephedrine;

Bronchospasm relaxants such as ephedrine, fenoterol, orciprenaline, rimiterol, salbutamol, sodium cromoglycate, cromoglycic acid and its prodrugs (described, for example, in *International Journal of Pharmaceutics* 7, 63-75 (1980)), terbutaline, ipratropium bromide, salmeterol and theophylline and theophylline derivatives;

Antihistamines such as meclozine, cyclizine, chlorcyclizine, hydroxyzine, brompheniramine, chlorpheniramine, clemastine, cyproheptadine, dexchlorpheniramine, diphenhydramine, diphenylamine, doxylamine, mebhydrolin, pheniramine, tripolidine, azatadine, diphenylpyraline, methdilazine, terfenadine, astemizole, loratidine and cetirizine;

Local anaesthetics such as benzocaine, bupivacaine, amethocaine, lignocaine, lidocaine, cocaine, cinchocaine, dibucaine, mepivacaine, prilocaine, etidocaine, veratridine (specific c-fiber blocker) and procaine;

Stratum corneum lipids, such as ceramides, cholesterol and free fatty acids, for improved skin barrier repair [Man, et al. *J. Invest. Dermatol.*, 106(5), 1096, (1996)];

Neuromuscular blocking agents such as botulinum toxin ("Botox®), suxamethonium, alcuronium, pancuronium, atracurium, gallamine, tubocurarine and vecuronium;

Smoking cessation agents such as nicotine, bupropion and ibogaine;

Insecticides and other pesticides which are suitable for local application;

Dermatological agents, such as vitamins A, C, B1, B2, B6, B12, B12α., and E, vitamin E acetate and vitamin E sorbate;

Allergens for desensitisation such as house, dust or mite allergens;

Nutritional agents and neutraceuticals, such as vitamins, essential amino acids and fats;

Macromolecular pharmacologically active agents such as proteins, enzymes, peptides, polysaccharides (such as cellulose, amylose, dextran, chitin), nucleic acids, cells, tissues, and the like;

Bone mending biochemicals such as calcium carbonate, calcium phosphate, hydroxyapetite or bone morphogenic protein (BMP);

Angiogenic growth factors such as Vascular Endothelial Growth Factor (VEGF) and epidermal growth factor (EGF), cytokines, interleukins, fibroblasts and cytotaxic chemicals, platelet derived growth factor (PDGF), fibroblast growth factor (FGF), tissue/wound healing growth factors; and Keratolytics such as the alpha-hydroxy acids, glycolic acid and salicylic acid; and DNA, RNA or other oligonucleotides.

Permeation enhancers (e.g. membrane permeation enhancers) such as ascorbic acid, citric acid, glutamine and Lauroylcarnitine Additionally, the biocompatible protein particles of the present invention are particularly advantageous for the encapsulation, incorporation and/or scaffolding of macromolecular pharmacologically active agents such as proteins, enzymes, peptides, polysaccharides, nucleic acids, cells, tissues, and the like. Immobilization of macromolecular pharmacologically active agents into or onto a particle can be difficult due to the ease with which some of these macromolecular agents denature when exposed to organic solvents, some constituents present in bodily fluids or to temperatures appreciably higher than room temperature. However, since the method of the present invention utilizes biocompatible solvents such as water, DMSO or ethanol the risk of the denaturation of these types of materials is reduced. Furthermore, due to the size of these macromolecular pharmacologically active agents, these agents may be encapsulated within the particles of the present invention and thereby are protected from constituents of bodily fluids that would otherwise denature them. Thus, the particles of the present invention allow these macromolecular agents to exert their therapeutic effects, while yet protecting them from denaturation or other structural degradation.

Examples of cells which can be utilized as the pharmacologically active agent in the biocompatible protein particles of the present invention include primary cultures as well as established cell lines, including transformed cells. Examples of these include, but are not limited to pancreatic islet cells, human foreskin fibroblasts, Chinese hamster ovary cells, beta cell insulomas, lymphoblastic leukemia cells, mouse 3T3 fibroblasts, dopamine secreting ventral mesencephalon cells, neuroblastold cells, adrenal medulla cells, endothelial cells, T-cells, combinations of these, and the like. As can be seen from this partial list, cells of all types, including dermal, neural, blood, organ, stem, muscle, glandular, reproductive and immune system cells, as well as cells of all species of origin, can be encapsulated successfully by this method.

Examples of proteins which can be incorporated into the biocompatible protein particles of the present invention include, but are not limited to, hemoglobin, glutamic acid decarboxylase, vasporessin, oxytocin, adrenocorticocotrophic hormone, epidermal growth factor, prolactin, luliberin or luteinising hormone releasing factor, human growth hormone, and the like; enzymes such as adenosine deaminase, tyrosine hydroxylase, alcohol dehydrogenase, superoxide dismutase, xanthine oxidase, and the like; enzyme systems; blood clotting factors; clot inhibitors or clot dissolving agents such as streptokinase and tissue plasminogen activator; antigens for immunization; hormones; polysaccharides such as heparin, chondroitin sulfate and hyaluronic acid; oligonucleotides; bacteria and other microbial microorganisms including viruses; monoclonal antibodies, such as herceptin and rituximab; vitamins; cofactors; growth factors; retroviruses for gene therapy, combinations of these and the like.

An efficacious amount of the aforementioned pharmacologically active agent(s) can easily be determined by those of ordinary skill in the art taking into consideration such parameters as the particular pharmacologically active agent chosen, the size and weight of the patient, the desired therapeutic effect, the pharmacokinetics of the chosen pharmacologically active agent, and the like, as well as by reference to well known resources such as Physicians' Desk Reference®: PDR—52 ed (1998)—Medical Economics 1974. In consideration of these parameters, it has been found that a wide range exists in the amount of the pharmacologically active agent(s) capable of being incorporated into and subsequently released from or alternatively allowed to exert the agent's therapeutic effects from within the protein particles. More specifically, the amount of pharmacologically active agent that may be incorporated into and then either released from or active from within the biocompatible protein particles may range from about 0.001% to about 200%, more preferably, from about 0.05% to about 100%, most preferably from about 0.1% to 70%, based on the weight of the particulate material. It is important to note that the pharmacologically active agents are generally homogenously distributed throughout the particulate material thereby allowing for a controlled release of these agents.

The particles of the present invention may optionally be coated or scored and may be formulated so as to provide slow- or controlled-release of the active ingredient.

Finally, one or more additive materials may be added to the coatable composition to manipulate the material properties and thereby add additional structure or modify the release of pharmacologically active agents. That is, while a particulate material that includes a relatively fast-degrading protein material without a particular additive material will readily degrade thereby releasing drug relatively quickly upon insertion or implantation, a particulate material that includes a particular polymeric material, such as polyanhydride, will degrade slowly, as well as release the pharmacologically active agent(s) over a longer period of time. Additionally, the addition of other additive materials, such as humectants like glycerin, pectin, polyethylene glycol, sorbitol, maltitol, mannitol, hydrogenated glucose syrups, xylitol, polydextrose, glyceryl triacetate and propylene glycol, may provide enhanced adhesion properties to parts of the body, such as mucosal tissue. Examples of biodegradable and/or biocompatible additive materials suitable for use in the biocompatible protein particles of the present invention include, but are not limited to polyurethanes, vinyl homopolymers and copolymers, acrylate homopolymers and copolymers, polyethers, cellulosics, epoxies, polyesters, acrylics, nylons, silicones, polyanhydride, poly(ethylene terephthalate), polyacetal, poly(lactic acid), poly(ethylene oxide)/poly(butylene terephthalate)copolymer, polycarbonate, polyethylene covinyl acetate, polybutylmethacrylate, polymethymethacrylate, poly(tetrafluoroethylene) (PTFE), polycaprolactone, polyethylene oxide, polyethylene glycol, poly(vinyl chloride), polylactic acid, polyglycolic acid, polypropylene oxide, poly(akylene)glycol, polyoxyethylene, sebacic acid, polyvinyl alcohol (PVA), 2-hydroxyethyl methacrylate (HEMA), polymethyl methacrylate, 1,3-bis(carboxyphenoxy)propane, lipids, phosphatidylcholine, triglycerides, polyhydroxybutyrate (PHB), polyhydroxyvalerate (PHV), poly(ethylene oxide) (PEO), poly ortho esters, poly(amino acids), polycynoacrylates, polyphophazenes, polysulfone, polyamine, poly(amido amines), fibrin, glycerin, pectin, sorbitol, maltitol, mannitol, hydrogenated glucose syrups, xylitol, polydextrose, glyceryl triacetate, propylene glycol, graphite, flexible fluoropolymer, isobutyl-based, isopropyl styrene, vinyl pyrrolidone, cellulose acetate dibutyrate, silicone rubber, copolymers of these, and the like. Other materials that may be incorporated into the coatable composition to provide enhanced features include, but are not limited to, ceramics, bioceramics, glasses bioglasses, glass-ceramics, resin cement, resin fill; more specifically, glass ionomer, hydroxyapatite, calcium sulfate, $Al_2O_3$, tricalcium phosphate, calcium phosphate salts, sugars, starches, carbohydrates, salts, polysaccharides, alginate and carbon. Additional other materials that may be incorporated into the coatable composition include alloys such as, cobalt-based, galvanic-based, stainless steel-based, titanium-based, zirconium oxide, zirconia, aluminum-based, vanadium-based, molybdenum-based, nickel-based, iron-based, or zinc-based (zinc phosphate, zinc polycarboxylate).

Other additives may be utilized, for example, to facilitate the processing of the biocompatible protein particles, to stabilize the pharmacologically active agents, to facilitate the activity of the pharmacologically active agents, or to alter the release characteristics of the biocompatible protein particles. For example, when the pharmacologically active agent is to be an enzyme, such as xanthine oxidase or superoxide dismutase, the protein matrix device may further comprise an amount of an enzyme substrate, such as xanthine, to facilitate the action of the enzyme.

Additionally, hydrophobic substances such as lipids can be incorporated into the biocompatible protein particles to extend the duration of drug release, while hydrophilic, polar additives, such as salts and amino acids, can be added to facilitate, i.e., shorten the duration of, drug release. Exemplary hydrophobic substances include lipids, e.g., tristeafin, ethyl stearate, phosphotidycholine, polyethylene glycol (PEG); fatty acids, e.g., sebacic acid erucic acid; combinations of these and the like. A particularly preferred hydrophobic additive useful to extend the release of the pharmacologically active agents comprises a combination of a dimer of erucic acid and sebacic acid, wherein the ratio of the dimer of erucic acid to sebacic acid is 1:4. Exemplary hydrophilic additives useful to shorten the release duration of the pharmacologically active agent include but are not limited to, salts, such as sodium chloride; and amino acids, such as glutamine and glycine. If additives are to be incorporated into the coatable composition, they will preferably be included in an amount so that the desired result of the additive is exhibited.

Additionally other particle embodiments include a protein-based material that has incorporated into it a marker system that allows the particles to be located and imaged using ultrasound, MRI, X-Ray, PET or other imaging techniques. The image marker can be made with air bubbles or density materials that allow easy visualization of the particles by ultrasound, MRI .... The incorporated materials can be metallic, gaseous or liquid in nature. Specific materials that may be utilized as image markers, contrast agents, paramagnetic imaging agents and the like are incorporated into the protein based materials, (e.g. biocoacervates or protein matrix materials) include, but are not limited to, gadolinium based paramagnetic imaging agents (e.g. Gd-DPTA), ferumoxides injectable solutions (e.g. Feridex®). It may be possible to cause the protein-based materials to react to an imaging technique, i.e., ultrasound to make bubbles or through the addition of another chemical or substance to the system (e.g., peroxide addition to a biocoacervate or biomaterial that contains peroxidase as an intrauterine marker that can be monitored by ultrasound). Also, the addition of a harmless unique salt solution, or enzyme, may promote gas production by the protein-based materials as an ultrasound maker. The particles of the present invention can contain agents that can be seen by ultrasound, MRI, PET, x-ray or any imaging device that is either known, in development or developed in the future.

One method of producing the biocompatible protein particles of the present invention is by first producing a protein matrix material or a spread matrix material. A discussion of protein matrix and spread matrix materials (e.g. cohesive body materials) may be found in U.S. patent application Ser. No. 09/796,170 filed on Feb. 28, 2001, the contents of which are incorporated herein. In various embodiments of the present invention, a protein matrix material or spread matrix material may be produced by providing one or more selected biocompatible purified proteins, adding other materials (pharmacologically active agents, additives, etc.) and combining the proteins and other materials with solvents (water) to form a coatable composition. Once prepared, the coatable composition may be coated onto any suitable surface from which it may be released after drying by any suitable method. Examples of suitable coating techniques include spin coating, gravure coating, flow coating, spray coating, coating with a brush or roller, screen printing, knife coating, curtain coating, slide curtain coating, extrusion, squeegee coating, and the like. The coated film (preferably having a substantially planar body having opposed major surfaces) is desirably thin enough so as to be capable of drying within a reasonable amount of time and also thin enough so that the film can be formed into a cohesive body comprising a substantially homogeneous dispersion of the components of the coatable composition. For example, a thinner film will tend to form a more homogeneous cohesive body when the film is formed into the shape of a cylinder. A typical coated film of the coatable composition have a thickness in the range of from about 0.01 millimeters to about 5 millimeters, more preferably from about 0.05 millimeters to about 2 millimeters.

Initially, when the film is first coated, it is likely to be non-cohesive, fluidly-flowable, and/or non self-supporting. Thus, the coated film is preferably dried sufficiently so that it becomes cohesive, i.e., the film preferably sticks to itself rather than other materials. The film may simply be allowed to dry at room temperature, or alternatively, may be dried under vacuum, conditions of mild heating, i.e., heating to a temperature of from about 25° C. to about 150° C., or conditions of mild cooling, i.e. cooling to a temperature of from about 0° C. to about 20° C. When utilizing heat to dry the film, care should be taken to avoid denaturation or structural degradation of the pharmacologically active agents incorporated therein. Also, care should be taken to not irreversibly denature the proteins of the cohesive body during preparation through various actions on the composition that will disrupt the secondary and/or tertiary structure of the protein(s) such as application of excessive heat or strong alkaline solution, which may cause coagulation/gelation. It is noted that the cohesive body may be prepared without the film step if the proper amounts of protein, solvent and other components are combined in the composition to achieve the necessary characteristics of the cohesive body. Therefore, the drying step may be omitted if a cohesive body can be created by simply mixing the various components (e.g. protein, solvent . . . ).

The specific solvent content at which the film and/or the composition becomes cohesive unto itself will depend on the individual components incorporated into the coatable composition. A cohesive body is achieved when the components of the composition are in the proper amounts so that the resulting composition is tacky or cohesive to itself more than to other materials or surface that it contacts. Generally, films that have too high of a solvent content will not be cohesive. Films that have too low of a solvent content will tend to crack, shatter, or otherwise break apart upon efforts to form them into a cohesive body. With these considerations in mind, the solvent content of a partially dried film and/or cohesive body will preferably be from about 10% to about 80%, more preferably from about 15% to about 65% and most preferably from about 20% to about 50%.

Once the film is capable of forming a cohesive body, such a cohesive body may be formed by any of a number of methods. For example, the film may be rolled, folded, accordion-pleated, crumpled, or otherwise shaped such that the resulting cohesive body has a surface area that is less than that of the coated film. For example the film can be shaped into a cylinder, a cube, a sphere or the like. Preferably, the cohesive body is formed by rolling the coated film to form a cylinder.

Once so formed, the cohesive body may be solidified prior to particle processing. The cohesive may be solidified into a compressed matrix or spread matrix form. A spread matrix form is generally solidifying the cohesive body utilizing one or more of solidifying techniques without applying compression to the cohesive body. It is noted that a combination of these techniques may also be utilized. Alternatives to solidify the cohesive body other than compression may be to apply heat, freeze drying, freezing to freeze fracture (e.g. liquid nitrogen, dry ice or conventional freezing) or other drying techniques to solidify the cohesive body before processing the cohesive body into particles. An illustration of one embodiment of particles of the present invention comprising collagen, elastin and heparin at a parts ratio of 7/2/lis depicted in FIG. 1.

As previously suggested, particles may be derived from a biocompatible protein material produced by solidifying the cohesive body by applying heat, crosslinking, freeze fracturing techniques such as liquid nitrogen freeze fracturing or dry ice freeze drying, vacuum or other similar drying techniques to eliminate excess solvent from the cohesive body rather than compressing it. These alternative techniques remove enough solvent from the cohesive body to provide for the production of distinct particles, but do not eliminate too much solvent wherein the interaction of solvent and protein is lost. Generally, the proteins, solvent and optionally the pharmacologically active agents will interact by binding through intermolecular and intramolecular forces (i.e., ionic, dipole-dipole such as hydrogen bonding, London dispersion, hydrophobic, etc.) that are created during the steps of forming a cohesive body and then also when further solidifying the cohesive body.

One example of an alternative method to solidify the cohesive body to make particles is by heating the cohesive body and then processing the resulting solidified cohesive body into particles. In such a method the cohesive body may be heated at temperatures ranging from 0°-150° C., preferably 20°-120° C. and most preferably 40°-100° C. Generally, the heating process may be conducted for approximately 15 seconds to 48 hours, preferably 20 seconds to 10 and most preferably 30 seconds to 1 hour. Embodiments of the resulting cohesive body following heating, or any of the alternative techniques identified above, usually have as little solvent as possible while still being cohesive and possessing the desired features relevant to the device's function, e.g., preferably a solvent content of from about 5% to about 60%, more preferably a solvent content of from about 10% to about 50% and most preferably 20% to 40%.

It is found that when a solidified cohesive body utilized in the production of the particles of the present invention includes one or more pharmacologically active agent(s), the partial drying of the film to form a cohesive body and subsequent solidification of the cohesive body, forces more solvent out of the body, thereby producing a resulting material that has a significantly higher concentration of pharmacologically active agents. As a result of the substantially uniform dispersion of a greater concentration of pharmacologically active agents, a sustained, controlled release of the pharmacologically active agent is achieved, while reducing the initial high concentration effects that can be associated with other devices that include pharmacologically active agents.

The cohesive body may also be solidified by compressing the cohesive body. For example, the cohesive body may be formed into a cylinder or any other shape by placing the cohesive body in the chamber of a device, such as a compression molding device, and compressing the cohesive body into a compressed matrix material. Subsequently, the resulting compressed matrix may be subsequently pulverized into particles (an explanation of methods to make particles is described below).

Any manually or automatically operable mechanical, pneumatic, hydraulic, or electrical molding device capable of subjecting the cohesive body to pressure is suitable for use in the method of the present invention. In the production of various embodiments of the present invention, a molding device may be utilized that is capable of applying a pressure of from about 100 pounds per square inch (psi) to about 100,000 psi for a time period of from about 0.2 seconds to about 48 hours. In other embodiments, the molding device used in the method of the present invention will be capable of applying a pressure of from about 1000 psi to about 30,000 psi for a time period of from about 0.5 second to about 60 minutes. In additional embodiments, the molding device used in the method of the present invention will be capable of applying a pressure of from about 3,000 psi to about 25,000 psi for a time period of from about 1 second to about ten minutes.

Compression molding devices suitable for use in the practice of the method of the present invention are generally known. Suitable devices may be manufactured by a number of vendors according to provided specifications, such as desirable pressure, desired materials for formulation, desired pressure source, desired size of the moldable and resulting molded device, and the like. For example, Gami Engineering, located in Mississauga, Ontario manufactures compression molding devices to specifications provided by the customer. Additionally, many compression molding devices are commercially available. See U.S. Pat. No. 6,342,250 and U.S. application Ser. No. 09/796,170, which are incorporated by reference herein, for a description of compression molding devices that may be utilized in the process of the present invention and methods utilized to produce a compressed protein matrix.

Figure 5:
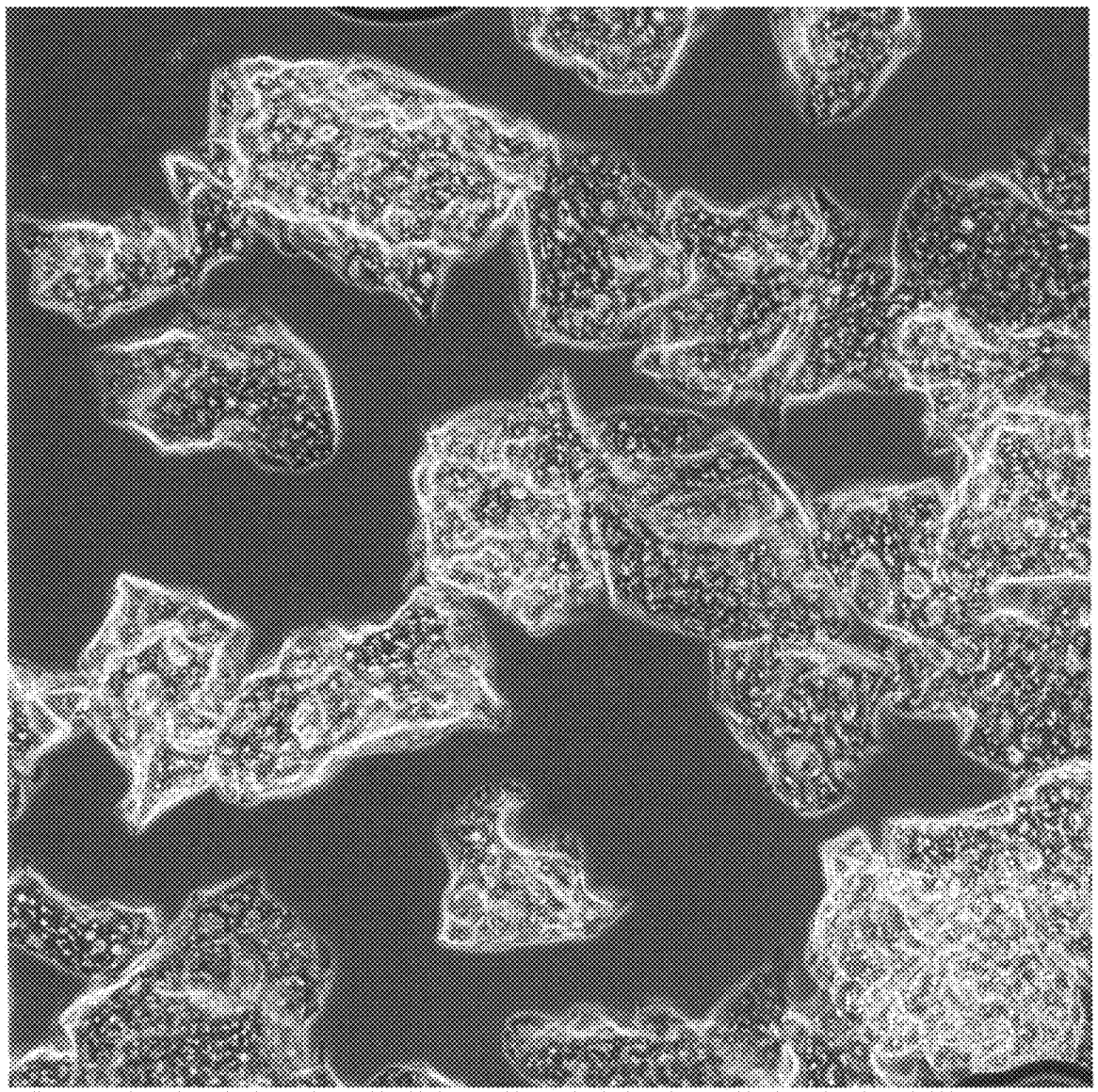
FIG. 5 depicts an embodiment of particles made from one embodiment of the biocoacervate of the present invention.

Alternatively, a biocoacervate or biomaterial including a biocoacervate may be utilized to make the particles of the present invention. A discussion of biocoacervate/biomaterials may be found in U.S. patent application Ser. No. 10,129, 117 filed on Aug. 26, 2004, the contents of which are incorporated herein. FIG. 5 depicts one embodiment of the final form of particles that include a biocoacervate. One method of producing a biocoacervate of the present invention is by providing one or more selected soluble or solubilized primary proteins, such as collagen, laminin or fibronectin and, in various embodiments, optionally, one or more soluble or solubilized secondary proteins such as elastin or albumen. The primary proteins, and in some embodiments the secondary proteins, are added to a sufficient amount of biocompatible solvent, preferably water, under heat until at least a substantial amount of the primary proteins are substantially dissolved in the solvent. It is noted that in various embodiments the primary proteins and secondary proteins are all substantially dissolved in the solvents. The proteins are added to the solvent(s) that are generally heated to approximately 30-150° C., preferably 40-90° C., and most preferably 40-70° C. thereby producing a protein solution. Once the protein solution is formed, one or more glycosaminoglycans, such as heparin or chondroitin sulfate are added to the protein solution thereby forming an amorphous biocoacervate, which drops out of the solution as a precipitate. It is noted that before adding the one or more glycosaminoglycans to the protein solution one or more other materials (e.g. pharmacologically active agents, additives, etc.) may be added to the one or more heated solvent(s) (e.g. water) while stirring. It is also noted that the secondary protein(s) may dissolved in a solution separate from the primary protein(s) (e.g. in some embodiments the same solution as the glycosaminoglycan) and added to the primary protein solution prior to or with the solution including the glycosaminoglycan. Once the biocoacervate has dropped out of solution, the solution and biocoacervate are normally allowed to cool to between 0-35° C., preferably 10-25° C., most preferably 17-22° C. and the solution is poured off the biocoacerate or the biocoacervate is extracted from the solution.

Figure 2:
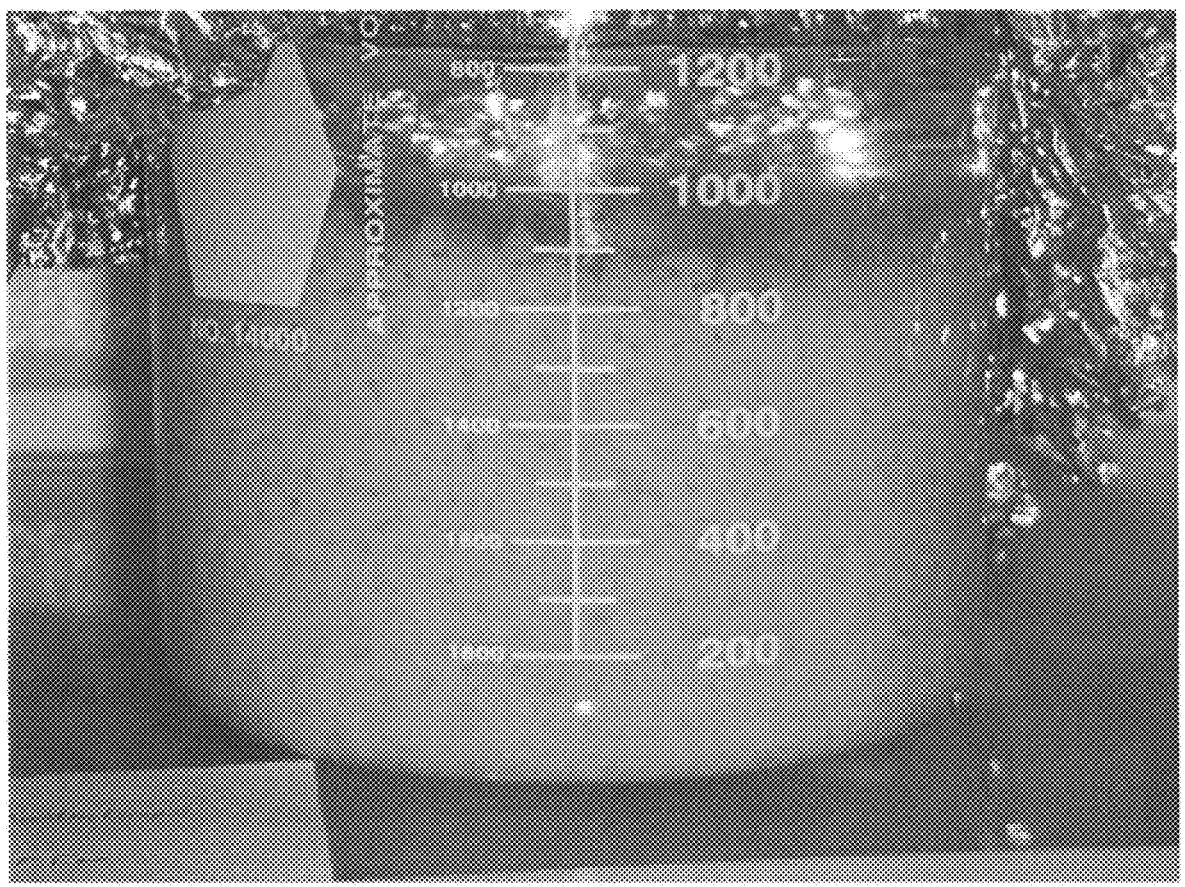
FIG. 2 depicts one embodiment of the particles of the present invention sieved to between 75 and 125 microns.

Many embodiments of the biocoacervate and biomaterials of the present invention are thermoplastics, thereby possessing thermoplastic chemical and mechanical characteristics. Therefore, the biocoacervates and some embodiments of the biomaterials have the property of softening when heated (e.g. to liquid form) and of hardening again when cooled; these thermoplastic materials can be remelted and cooled time after time without undergoing any substantial chemical change. In view of these thermoplastic characteristics, various embodiments of the formed biocoacervate may be reformed into any shape and size by simply heating the biocoacervate until it melts and forms a liquid. Generally, the biocoacervate can be melted at a temperature between 20-120° C., preferably 25-80° C., most preferably 30-65° C. Next, the melted biocoacervate may be poured into a cast, molded or processed into any desirable shape and allowed to cool, thereby resolidifying and reforming into the desired shape and/or size. FIG. 2 depicts an example of individual raw material pellets or wafers of the biocoacervate of the present invention. It is noted that at high levels of cross-linking the thermoplastic characteristics of some of the embodiments of the present invention may diminish and/or be eliminated.

It is noted that in forming the protein solution, the primary and secondary proteins, the biocompatible solvent(s), and optionally the pharmacologically active agent(s) and additive(s) may be combined in any manner. For example, these components may simply be combined in one step, or alternatively, the primary and secondary protein materials may be dissolved in one or multiple biocompatible solvents and an additional protein material, pharmacologically active agent and/or additive may be dissolved and/or suspended in the same or another biocompatible solvent. Once the components are placed into one or more solutions, the resulting solutions may be mixed to precipitate the amorphous biocoacervate.

The resulting biocoacervate preferably has the maximum solvent amount absorbable with as little excess solvent as possible while still being structured into a shape-holding amorphous solid and possessing the desired features relevant to the material's and/or device's function, e.g., in various embodiments a solvent content of from about 20% to about 90%, in some embodiments a solvent content of from about 30% to about 80% and most in additional embodiments a solvent content from about 40% to 75%. Additionally, the amount of proteins found in the resulting coacervate or biomaterial may vary between from about 10% to about 80%, in some embodiments from about 20% to 70% by weight, and in other embodiments from about 25% to 60% by weight based upon the weight of the resulting biocoacervate or biomaterial. The amount of glycosaminoglycan present in various embodiments of the present invention generally is about 1% to about 25%, in some embodiments about 3% to 20% by weight, and in other embodiments about 5% to 15% by weight based upon the weight of the protein included in the biocoacervate.

Once the biocoacervate is formed, it may be optionally pressed or vacuumed to further form, modify, set the configuration and/or remove any excess solvent or air trapped within the biocoacervate. It is noted that the resulting biocoacervate may be melted and placed in vacuum to remove any excess air trapped within the coacervate. The vacuum or compression may also be performed when a melted coacervate is resetting to a solid state by pouring the melted biocoacervate in a mold and applying pressure or applying vacuum while cooling. The biocoacervate may optionally be dried to reduce water content to transform the biocoacervate structure into more of a cohesive body material to allow it to accept compression. Any manually or automatically operable mechanical, pneumatic, hydraulic, or electrical molding device capable of subjecting the biocoacervate to pressure, such as those described above, is suitable for use in the method of the present invention.

The biocoacervate of the present invention is generally not soluble in water at room temperature. However, the coacervate does dissolve in saline solution or other physiological solutions. A biocoacervate or biomaterial that does not dissolve in saline solution or other physiological solutions may be produced by setting the biocoacervate in the desired configuration and size by utilizing a crosslinking technique. It is also noted that various crosslinking reagents, techniques and degrees of crosslinking manipulate the melting point of the crosslinked material and its physical and biological characteristics. It has been found that the application of crosslinking to the biocoacervate will generally tend to raise the melting point of the biocoacervate. Crosslinking of the biocoacervates will be discussed further in the paragraphs to follow along with the crosslinking techniques to crosslink the protein matrix and spread matrix materials.

Many crosslinking techniques known in the art may be utilized to set the protein based materials (e.g. compressed matrix, spread matrix, cohesive body, biocoacervate . . . ) into the desired configuration, thereby forming a biomaterial and resulting particles that do not dissolve in solution (e.g. saline solution) or physiological environments. For example, embodiments of the protein-based materials may be crosslinked by reacting the components of these materials with one or more suitable and biocompatible crosslinking agent. Crosslinking agents include, but are not limited to glutaraldehyde, p-Azidobenzolyl Hydazide, N-5-Azido-2-nitrobenzoyloxysuccinimide, tannic acid, 4-[p-Azidosalicylamido]butylamine, glycidyl ethers such as 1,4-butandiol diglycidylether, any other suitable crosslinking agent and any combination thereof. A description and list of various crosslinking agents and a disclosure of methods of performing crosslinking steps with such agents may be found in the Pierce Endogen 2001-2002 or 2003-2004 Catalog which is hereby incorporated by reference. It is noted that one or more crosslinking techniques may be applied at any stage of the manufacture of the protein-based materials and/or particles of the present invention. Furthermore, it is also noted that multiple applications of crosslinking agents at different stages may produce desired products. For example, crosslinking the protein-based materials, such as the compressed matrix material or biocoacervate, after initial formation and then again following particle formation has proven effective.

Furthermore, it is noted that embodiments of the coacervates of the present invention may include crosslinking reagents that may be initiated and thereby perform the crosslinking process by E-beam, UV light activation or other radiation source, such as ultrasound or gamma ray or any other activation means.

The protein-based materials can be passivated following crosslinking with agents containing primary amine groups, such as amino acids (e.g. glycine, glutamine, lysine . . . ). Additionally, reducing agents (e.g. schiff-base reagents, such as borohydrides) may be applied to the protein based materials and/or particles to stabilize the crosslinked bonds.

The protein-based materials may also be crosslinked by utilizing other methods generally known in the art. For example, the compressed matrix, spread matrix, cohesive body and/or biocoacervates of the present invention may be partially or entirely crosslinked by exposing, contacting and/or incubating these materials with a gaseous crosslinking reagent, liquid crosslinking reagent, light, heat or combination thereof. In various embodiments of the present invention these protein-based materials may be crosslinked by contacting the coacervate with a liquid or gaseous crosslinking reagent, such as glutaraldehyde or 1,4-butandiol diglycidylether. In one embodiment of the present invention the protein based materials are crosslinked in a solution of between 0.01%-50% gluteraldehyde. Additionally, it is noted that in processes including a crosslinking agent the protein-based materials used to produce the particles of the present invention are generally exposed to the crosslinking agent for a period of 1 min to 48 hours, in various embodiments between 5 min. and 18 hours and in additional embodiments between 15 min. and 12 hours. Also, temperature can be used to regulate and/or stabilize the protein during the crosslinking process (e.g. low temperatures can stabilize the proteins hence crosslinking the proteins and limiting bond breaking). Various embodiments of the crosslinking techniques can also serve the duel purpose of crosslinking the protein-based materials/particles and also sterilize the protein-based materials/particles. For example, glutaraldehyde can be utilized to crosslink the materials and/or particles and also sterilize the materials and/or particles.

Additionally, embodiments of the present invention may include the addition of reagents to properly pH the resulting biocompatible protein particles and thereby enhance the biocompatible characteristics of the particles with the host tissue of which it is to be administered. When preparing the biocompatible protein materials, the pH steps of the mixture of biocompatible materials (e.g. purified proteins, pharmacologically active agents, additives, and the biocompatible solvent(s)) may occur prior to the preparation of the cohesive body, after the cohesive body is made or after the compressed matrix or spread matrix is produced. The pH steps can be started with the addition of pH reagents to the protein or to the mixture of protein material(s) and optional biocompatible materials, or the pH steps can be started after mixing the material(s) and solvent(s) together before the cohesive body is formed.

Alternatively, in various embodiments, when preparing the biocoacervate, the pH reagents are added to the protein solution prior to addition of the glycosaminoglycans. However, the pH reagent may alternatively be added after the amorphous biocoacervate is formed. For example the pH reagent may be added to the melted form of the biocoacervate in the attempt to obtain the proper pH levels.

For example, when adjusting the pH of the protein based materials, the pH steps can include the addition of drops of pH solutions, such as 0.05N to 4.0N acid or base, to the solvent wetted material, biocoacervate solutions, cohesive body or resulting protein-based materials until the desired pH is reached as indicated by a pH meter, pH paper or any pH indicator. In other embodiments, the addition of drops of 0.1N-0.5 N acid or base are used. Although any acid or base may be used, examples of acids and bases are HCl, KOH, NaOH and combinations thereof respectively. If known amounts of biocompatible material are used it may be possible to add acid or base to adjust the pH when the biocompatible material is first wetted, thereby allowing wetting and pH adjustments to occur in one step. It has been found that adjusting the pH at or between 4 and 9, and in many embodiments at or between 6 and 8, have provided beneficial materials. Furthermore, pores in the particles may be created and/or enhanced from alkaline hydration steps performed during the pHing of the materials.

Figure 3:
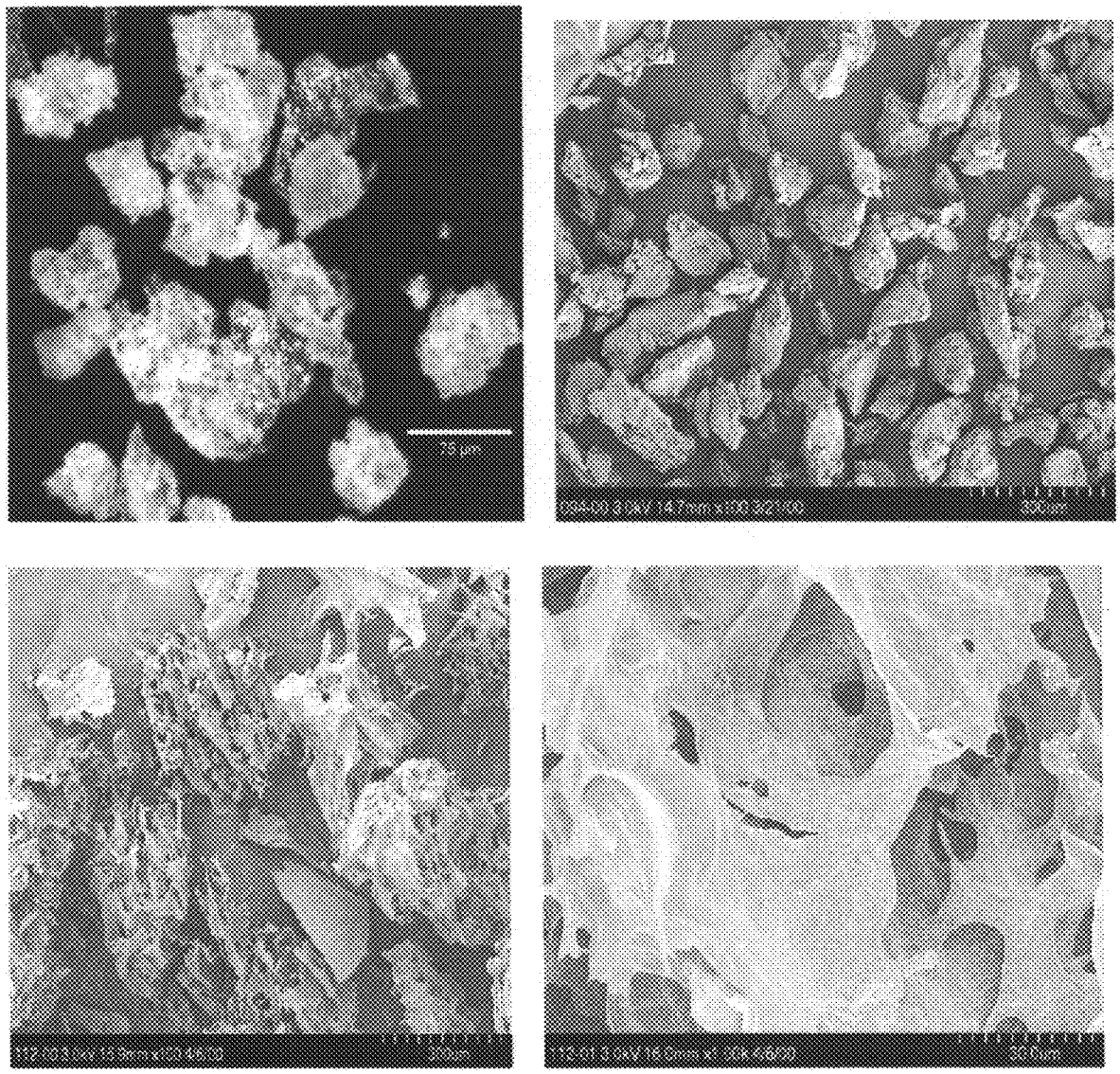
FIG. 3 depicts one embodiment of a slurry of the present invention including particles in saline solution being passed through a syringe.

Furthermore, the protein based materials, such as the compressed matrix, spread matrix, cohesive body, biocoacervate, biomaterials including the biocoacervate and/or resulting particles from these materials may be set up with pores that allow fluid flow through that particles and also enhances movement of the pharmacologically active agents through the particles. Pores may be created in the cohesive body or particles by incorporating a substance in the cohesive body during its preparation that may be removed or dissolved out of the matrix before administration of the device or shortly after administration. Porosity may be produced in particles by the utilization of materials such as, but not limited to, salts such as NaCl, amino acids such as glutamine, microorganisms, enzymes, copolymers or other materials, which will be leeched out of the protein matrix to create pores. FIG. 3 depicts one embodiment of the present invention, wherein glutamine was included in the cohesive body and then dissolved out during crosslinking to form pores in the particles. Other functions of porosity are that the pores create leakage so that cells on outside can receive fluids that include the contents of the particles and also that cells may enter the particles to interact and remodel the matrix material to better incorporate and function within the host tissue.

The particles of the present invention are generally prepared by further processing the protein-based materials. It is noted that in various embodiments, the particles may be produced from the biomaterials of the present invention wherein the biomaterials are at least partially produced from one or more of the protein based materials (e.g. compressed matrix, spread matrix and/or biocoacervate material). Generally, in various embodiments the biomaterials included in the particles of the present invention can include approximately 25-100% protein based materials; in other embodiments greater than 50% protein based materials; and in yet other embodiments greater than 75% protein based materials.

Various methods may be utilized to produce the particles of the present invention. Examples of methods of producing the particles of the present invention includes extruding, dropping/dripping, atomizing biocoacervate in solution, biocoacervate deaggregation into particles, crushing, cutting, pulverizing, homogenizing or grinding of the solidified cohesive body in either wet or dry conditions until the particles are formed. These methods of producing the particles utilized in products of the present invention may be performed following the freezing of the cohesive body in liquid nitrogen, by utilizing other freeze/solid fracture or particle forming techniques or by partially heating the cohesive body until substantially rigid, but still retaining some solvent content.

In two embodiments of the present invention the particles are prepared utilizing a mill grinder or a homogenizer. Types of mill grinders and homogenizers that may be utilized include, but are not limited to ball mills, grinder stations, polytron homogenizers and the like. One example of a polytron homogenizer that may be utilized in processing particles of the present invention may be a Polytron PT1200E purchased from the Kinematica corporation of Switzerland. An example of a ball mill that may be utilized in processing particles of the present invention may be a ballmill/rollermill purchased from U.S. Stoneware, Inc. and distributed by ER Advanced Ceramincs of Palestine, Ohio.

After the particles are formed using the various methods described above, they are usually characterized for their basic structure. First the particles may be segregated for size ranges using a series of pharmaceutical drug sieves. Additional characterization of the particles will consist of verification of the shape and size of the particles using light and electron microscopy.

Generally, the particles may vary in size but are normally equal to or less than 2 mm. In many embodiments of the present invention the particles are approximately 10 nm-1.75 mm, in some embodiments 500 nm-1.5 mm and in many embodiments 1-1000 μm. In one embodiment of the present invention the particles are sized to easily pass through a 27-30 gauge needle. However, the particles or a particle slurry including the particles may be delivered in any way known in the art including delivery through a needle, air-gun, iontophoresis, etc. A characteristic of the particles produced from the biocompatible protein material is that they no longer aggregate when in the fully hydrated particulate state. Furthermore, prior studies have demonstrated that the particles do not aggregate in saline and are easily delivered through small gauge needles. The particles can be made to disassociate at very slow or fast rates in aqueous solutions. It is also noted that generally, many particle embodiments of the present invention are substantially insoluble thereby allowing them to be integrated and remodeled by the host tissue rather than excreted.

In other embodiments the particles of the present invention may be dried and administered in a dry or semi-dried state. The drying of the particles will allow them to occupy a smaller space upon delivery and further allow them to expand upon rehydration. The drying of the particles can be performed by any of the drying processes disclosed herein or those known in the art. For example, freeze drying and/or drying agents such as alcohols, may be utilized to dry the particles. In one example, the dried particles may be utilized as an adhesive to join tissues, wherein the rehydration produces particles that are tacky and adhere to the host tissue, thereby linking separated tissues. In various embodiments of the present invention, the particles can be processed to a hardened state, thereby making them easily administered into the skin or tissue by techniques, such as airgun administration.

Particles of the present invention are advantageous for a variety of reasons. For example, the size and shape of the particles of the present invention provide a way to adjust the biological response of the host tissue (e.g. particles of the present invention have been found to fit and intermingle in the interstices of the host tissue, thereby enhance the bulking characteristics, biodurability or bioduration of the particles; particles also allows the material to be interdispersed or interspaced in the host tissue). Various particle embodiments of the present invention also provide a slower drug release matrix in comparison to gels, viscous solution etc. Furthermore, particles also provide a barrier to which most of the drug is not in direct contact with tissue and can be controllably released through a number of matrix related mechanisms (e.g. ion pairing, diffusion, enzymatic degradation, surface erosion, bulk erosion, etc.).

The particles may also be aggregated or crosslinked following formation and/or after administration (e.g. injection) to a patient by including a photoinitiator or a chemical initiator on one or more components of the particles or by administering a biocoacervate adhesive to the particles. For example, one or more proteins (e.g. collagen) or additives (e.g. hyaluronic acid), may include a photoinitiator or chemical initiator that when activated bind the particles to each other or to a surface they come in contact with, such as tissue or a medical device. Preferably a nontoxic photoinitiator such as eosin Y photoinitiator is used. Other initiators include 2,2-methoxy-2-phenylacetophenone and ethyl eosin. The polymerization process can be catalyzed by light or chemical in a variety of ways, including UV polymerization with a low intensity lamp emitting at about 365 nm, visible laser polymerization with an argon ion laser emitting at about 514 nm, visible illumination from a conventional endoilluminator used in vitreous surgery, and most preferably by illuminating with a lamp that emits light at a wavelength between 400-600 nm, such as, for example, a 1-kW Xe arc lamp. Illumination occurs over about 1-120 seconds, preferably less than 30 seconds. Since the heat generated is low, photopolymerization can be carried out in direct contact with cells and tissues.

Alternatively, the particles of the present invention can be aggregated or crosslinked together, the particles can be adhered to the host tissue or the host tissue can be adhered together or bulked without particles by the utilization of a biocoacervate adhesive of the present invention. In various embodiments of the present invention, a melted form of the biocoacervate can be administered to the particles and/or host tissue simultaneously or within a relatively short period of time (e.g. within 10 minutes) of administration of a crosslinker to the host tissue. Such administration of the liquid biocoacervate with the crosslinker causes a solidification of these components, thereby aggregating the particles and/or adhering the host tissue. The biocoacervate adhesive may be used to adhere host tissue to host tissue or host tissue to graft material. For example, the biocoacervate adhesive may be used to adhere a blood graft to the native vessel by applying the adhesive to the native vessel and graft at the anastamosis site. This can assist in reducing blood seepage/leaking at the connection points of the graft and vessel including leaking at suture and other fastener points or related tears. Additionally, a cross-linker passivator (e.g. free-form protein, free-form peptide, polylysine, lysine, glutamine or glycine) can be included in the particles as an additive or can be administered slightly before, simultaneously or shortly after administration of the cross-linker to the host tissue. The inclusion in the particles or administration of such a passivator would deactivate any unused ends of the cross-linker that is present following interaction with the biocoacervate. It is noted, that the biocoacervate adhesive may also be used to produce a coating on surfaces with or without particles, such as coating medical devices (e.g. stents, sutures . . . ) or may be utilized to adhere medical devices or other materials to host tissues.

The biocompatibility and tissue response to such particles has been shown to be favorable in related cardiovascular, tissue filler and drug delivery research. Also, the activity of an attached cell, such as fibroblasts, can be altered by changes in the fabrication technique (compression & cross-linking) and composition of the particles of the present invention. Additionally, cells can take on different shapes depending upon the type of particle they contact. The ability of cells to take on different shapes is indicative of their ability to respond to their environment for specialized cell functions (e.g., differentiation, proliferation).

The combined preliminary work aimed at the processing, the biocompatibility, the drug release, and the cell attachment capabilities demonstrate that the particles of the present invention can be applied as materials for numerous clinical applications including many areas of tissue filler and tissue, tissue regeneration, hair stimulation, bulking agents, bandages and dressings, wound healing, skin treatment and rejuvenation, biocompatible barriers and drug delivery. For example, the addition of chemotactic agents, cell attractants or stimulants (e.g. vitamins, fibroblast growth factor (FGF), platelet derived growth factor (PDGF), transforming growth factor (TGF)) may be included in the particles of the present invention to attract to or next to the site or stimulate cells within or next to the site where the particles are administered.

The particles of the present invention may be administered to a patient by a number of administration techniques know in the art. Examples of such techniques include, but are not limited to, injection or implantation, as well as, intradermal, intramuscular, interosseous, intraosseous, intraosteo, intraperiosteo, intraligament, subcutaneous, or any other mode of delivery. Depending on the desired therapeutic effect, the particles of the present invention may be used to regenerate tissue, repair tissue, replace tissue, and deliver local and systemic therapeutic effects such as analgesia or anesthesia.

In various embodiments of the present invention, the particles may be utilized as a tissue filler or bulking agent by administering them subcutaneously or intradermally to the patient by a variety of administration techniques known in the art. One such administration procedure of the present invention includes the injection of the particles in a slurry or in a wetted state into the desired site by syringe. This procedure may be administered when the particles are placed in solution for delivery or are simply in a wetted state or dry state. Wetted particles generally do not have excess solvent and are flexible and/or compressible to easily fit through a needle smaller in gauge size than the actual size of the particles. Dry state particles are particles that have been dried to remove additional water, thereby allowing them to be rehydrated upon administration and may be injected by airgun or syringe into the skin/tissue.

Figure 4:
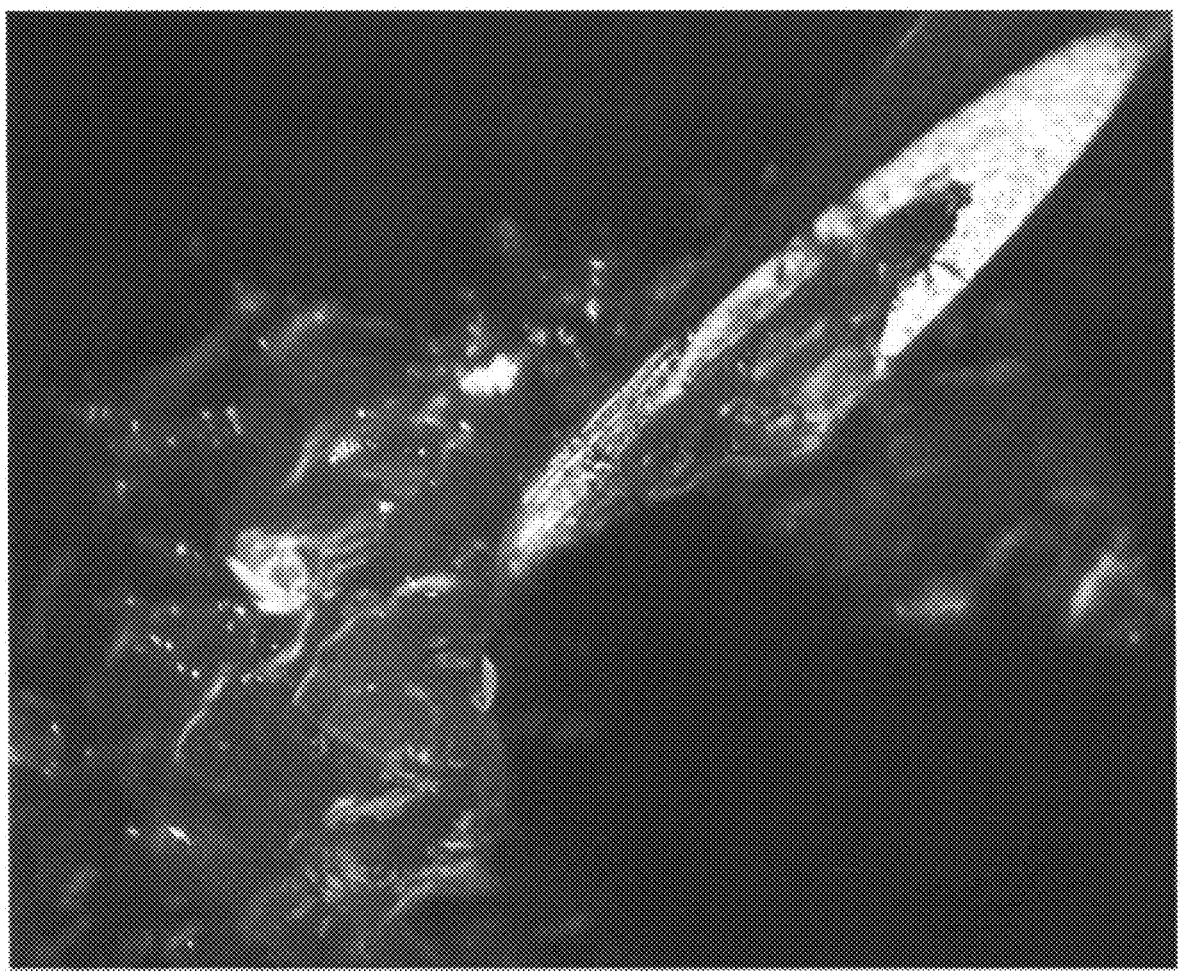
FIG. 4 depicts an embodiment of the biocoacervate of the present invention in droplet form prior to processing into particles.

Saline or purified water may be employed to prepare the slurry or wet the particles, but any biocompatible solution may be utilized. Saline has been selected for the initial material for several reasons including its common use in medical procedures and its availability in a sterile form. Additionally, purified water is generally utilized with the biocoacervate and corresponding biomaterials of the present invention. However, any suitable solvent may be utilized to produce the slurry or wet the particles of the present invention. Also, lubricants, such as polyvinylalcohol, polyethylene glycol, dextran, proteins (human, bovine, porcine, or equine) such as collagen, elastin, albumin, proteoglycans or glycans, hyaluronic acid, lipids, oils or any other lubricious agent, may be added to the particles or slurry to facilitate injection of the particles through a needle syringe assembly. These lubricants assist in facilitating the administration of the particles through the applicator, such as a syringe and also may be made to act as an immunogenic mask, thereby reducing potential inflammatory and/or immune responses. In various embodiments of the present invention the lubricants may comprise approximately less than 5% and preferably less than 1% of the particle or slurry contents. The slurry or wetted particles may be delivered in any way known in the art including delivery through a needle. FIG. 4 depicts one embodiment of a slurry of the present invention including particles in saline solution being passed through a syringe.

In various procedures the particles may be injected or surgically implanted and packed into and/or around a desired and/or injured site. For example, particles may be injected or surgically packed into and around an injured or vacant area or fluid/semifluid area, such as a fractured bone, wrinkle, joint (e.g. knee joint), spinal disc, and organ wall (e.g. bladder wall) and subsequently sealed into position by the host tissue surrounding the injured or vacant area. The injection or implantation of biocompatible protein particles of the present invention allows for the particles to stimulate desired tissue response, remodel and/or integrate with and/or resorb into the surrounding tissue or remain positioned in the injured or vacant area after it has mended or healed.

In various embodiments of the present invention, the particles and/or biocoacervate material (e.g. MasterGel material) and surrounding body part can be treated through the skin and/or tissue and/or organ with the penetration of chemical enhancers (e.g. vitamins such as vitamin C and/or E, citric acid, glycerol, retinol, ketogluterate, ferrous ion, sodium and magnesium salts of ascorbyl-2-phosphate, sodium or magnesium ascorbate, glucocorticoide such as hydrocortizone and cortizone, antioxidants, flavonoids such as quercetine, DMSO, methylsulfonyl methane (MSM), coenzyme Q10, amino acids, selenium, calcium, para-aminobenzoic acid (PABA) and its salts, potassium para-aminobenzoic acid, carnitines such as acetyl-L-carnitine, tamoxifen, copper, verapamil, cholchicine and combinations thereof) and/or radiation (e.g. Electromagnetic radiation: (Energy in the form of electromagnetic waves or photons.), Non-ionizing, Thermal radiation (heat radiation), Radio waves, Microwave radiation, Visible light, such as light that is visible to the naked eye, Ionizing, Ultraviolet radiation (UV) is electromagnetic radiation with a wavelength shorter than that of visible light, but longer than soft X-rays, X-rays (e.g. X-Rays used in radiography for medical diagnosis, Gamma radiation (e.g. Gamma radiation emitted by radio-active atoms), Particle radiation: (Energy in the form of moving subatomic particles, Alpha radiation, composed of the nuclei of helium-4 atoms, Beta radiation, consisting of energetic electrons or positrons, and Neutron radiation, consisting of neutrons). Other chemical enhancers include, but are not limited to, skin penetration enhancers to increase the permeability of the skin to the active material and permit the active material to penetrate through the skin and into the bloodstream (e.g. oleic acid, amino acids, oleyl alcohol, long chain fatty acids, propylene glycol, polyethylene glycol, isopropanol, ethoxydiglycol, sodium xylene sulfonate, ethanol, N-methylpyrrolidone, laurocapram, alkanecarboxylic acids, dimethylsulfoxide, polar lipids, N-methyl-2-pyrrolidone . . . ), pharmaceutically acceptable agents (e.g. alcohols, moisturizers, humectants, oils, emulsifiers, thickeners, thinners, surface active agents, fragrances, preservatives, antioxidants, vitamins, and/or minerals) and pharmaceuticals combined with polymeric substances (e.g. ethylcellulose, hydroxypropyl cellulose, ethylene/vinylacetate, polyvinyl pyrrolidone, and the like). In various embodiments, the chemical enhancers may be formulated to provide a composition in gel form, which may be dissolved in solvent such as methylene chloride, evaporated to the desired viscosity, and then applied to a backing material to provide a patch that may be administered to the tissue above the protein-based particles. The outcome of this treatment is to facilitate the biochemical and biological response to the particulate material. An example of this response is to excite fibroblasts in the area to proliferate to a greater amount and/or interact with the particulate material of the present invention to produce extracellular matrix (e.g., collagen) to a greater amount. This can be done with chemicals that penetrate into the body part to cause this effect or with radiation that in some embodiments may be dosed to activate extracellular matrix formation without ablation or with ablation. Many examples of these chemicals and radiation exist today.

The chemical and/or radiation treatment may interact with cells, biochemicals, extracellular matrix material, drugs, coating, device, medicaments, particles, MasterGel material or particles alone or any combination to augment the body part-particle/material effect. The effect can be to facilitate activity or to inhibit activity or both, depending on the timing of the treatment. For example, the chemical and/or radiation treatment may be used to treat tissue and/or skin when a tissue filler comprising the particles of the present invention are administered. In various embodiments, the chemical and/or radiation treatment can be administered to a patient following the treatment of wrinkles or other age related lines or creases with the particles of the present invention. A case study addressing such an application is as follows:

Intradermal Injection with Topical Treatment Case Study:
PURPOSE: The purpose of this blinded, side by side, rabbit study is to test protein based particles (e.g. biocoacervate particles as a dermal filler injected into the intradermal space in response to a topical lotion.
JUSTIFICATION FOR SELECTION OF THE TEST SYSTEM: The rabbit was suggested as an appropriate animal model for evaluating biomaterials by the current United States Pharmacopoeia (USP) testing guidelines for plastics/polymers/elastomers classification.
Procedure for Identification of the Test System:
  a) Species/Strain: Albino rabbits (Oryctolagus cuniculus)/ New Zealand White strain;
  b) Sex: Either males or females were used for this study;
  c) Source: Rabbits were purchased from a certified commercial vendor of laboratory animals;
  d) Weight Range: Each rabbit will weigh at least 2.5 kg;
  e) Age: Adult;
  f) Number: Two (2) rabbits were used in this assay;
  g) Diet: Animals were supplied with certified commercial feed, ad libitum. There are no known contaminants present in the feed that were expected to interfere with the test results.
  h) Water: Animals were supplied, ad libitum, with potable water from the St. Paul municipal water supply. There are no known contaminants present in the water that were expected to interfere with the test results.
EXPERIMENTAL DESIGN: The test material, in syringes pre-loaded by the Sponsor, were injected into the dermis of the rabbits. Testing personnel were blinded to the test article and lotion being used. Each rabbit had four (4) test articles and 16 injection sites, according to FIG. 1. Each site received 0.1 cc of test material. The sites were circled with black indelible marker. Starting on Day 7, the injection sites received a topical application of the Sponsor supplied lotions. One lotion was applied to the dermal injections on the left side. The other was applied to the injections on the right side. The lotion application took place every 2-3 days until study termination. Animals were palpated at the injection sites weekly. After the appropriate in life time (70 days), the animals were euthanized. The injection sites were harvested and allowed to fix for several days in formalin. The fixed skin samples were then sliced at 2-4 mm intervals extending through the injection site. The tissue sections were microscopically viewed for any gross evidence of a depot of test material in the dermis.
Test Method:
  a) Selection of Animals
Animals were selected at random from a larger pool of animals. Selection criteria was based on the required weight range of this study. Each animal was observed for any signs of clinical disease prior to introduction into the study.

b) Test Article Preparation: The test articles were implanted as provided by the Sponsor.

c) Animal Preparation:
   i) Each rabbit was weighed and the weight recorded.
   ii) The fur of the animals was clipped on both sides of the spinal column to expose an area of approximately 10 cm on each side. The loose fur was removed.

d) Test Article Administration: The test material in Sponsor loaded syringes was injected into the dermis of the rabbits according to FIG. 1. Each rabbit had four (4) test articles and 16 injection sites. The sites were approximately 3 cm apart. Each site received 0.1 cc of test material injected through a 25 gauge needle. The sites were then marked with a circle that is tight around the injection site and includes a small dot in the center of the injection site.

| FIG. 1 DIAGRAM OF IMPLANT PLACEMENT ||||||
| --- | --- | --- | --- | --- | --- |
| Left ||| Right |||
| 1 | 1 | Spine | 1 | 1 |
| 2 | 2 |  | 2 | 2 |
| 3 | 3 |  | 3 | 3 |
| 4 | 4 |  | 4 | 4 |

Legend: 1. Test article A, 2. Test article B, 3. Test article C, 4. Test article D
The identification of the test articles will be recorded in the raw data.

e) Clinical Observations: Clinical observations will be recorded daily for each animal.

f) Site Palpations: Each individual test site was palpated and the results recorded weekly. The relative size (percentage of remaining test material) was recorded. The sites were also remarked with black indelible marker weekly.

g) Lotion Application:
   i) Starting on Day 7, the lotions were applied to the injection sites. Lotion A (acorbic acid solution) was applied to the left side of the animal. Lotion B (saline solution) was applied to the right side. Lotion A (ascorbic acid) was marked with a dot and lotion B (saline solution) was marked with three lines in order to avoid confusion during application. The lotions are light sensitive and were stored in the dark at room temperature. The lotions were only be exposed to light during testing.
   ii) The lotion was applied with an applicator supplied by the Sponsor. The vial of lotion was opened. The applicator tip was inserted until saturated. The wet applicator tip was placed onto the implant site with the wide/flat side down. A slight amount of pressure will be used to apply the lotion. The pressure was not too great to have the lotion run out of the applicator. The applicator was held in place for 15 seconds per dermal site and was rewet after each application site. Care was taken not to lose lotion. A sufficient amount of test article was applied to create visual evidence of new liquid being applied. The lotion was applied to penetrate the fur to wet the skin.
   iii) The application of the lotion was repeated 4 times to give a total of 5 applications of lotion per site per application day. There was at least a 180 second interval between applications at each site. The lotion procedure was completed within one hour of initiation.
   iv) The lotion application took place every 2-3 days (Monday, Wednesday, and Friday, approximately 3 hours from the initial lotion application) throughout the remainder of the study duration. A new lotion and applicator was used for each application day.
   v) After each lotion application, the amount of lotion remaining was assessed. The raw data indicated whether or not lotion was remaining in the bottle.
   vi) Only on Fridays after all lotion applications, the skin near the implant sites was shaved. Care was taken not to abrade the skin at the implant sites.
   vii) In addition, the center dot marking of the site was reapplied on Fridays after the lotion application was complete.

h) Termination Procedures:
   i) Each rabbit was weighed and the termination weight recorded.
   ii) The rabbits were euthanized with a Sodium Pentobarbital based solution on Day 70.
   iii) After euthanasia, sufficient time was allowed to elapse for the tissue to be cut without bleeding.
   iv) The intradermal implant sites were carefully removed. Gross observations was made and recorded.
   v) In addition to the test article sites, two (2) control sites not injected with dermal filler were explanted from each rabbit.
   vi) The injection sites, control sites and any gross lesions were preserved in 10% formalin and were microscopically evaluated.

i) Histopathology:
   i) Representative sections were processed for histopathology and interpretation. Two sets of slides were created. One set was stained with hematoxylin & eosin. The other set was stained with Masson's Trichrome.
   ii) The pathology report included a histological assessment of test article retention in the injected sites and local tissue response. The test results revealed that topical vitamin C solutions applied to the skin promoted biointegration and were compatible with the dermal particles of the present invention implanted beneath the lotion application.

TEST DURATION: The test article was implanted for 70 days.

The above study was conducted and no adverse events were seen. Integration of the particle material of the present invention (i.e. CosmetaLife) and extracellular matrix was witnessed in the above study.

The particles of the present invention may be utilized in a number of medical applications that will now be further described below. It is noted that any additional features presented in other embodiments described herein may be incorporated into the various embodiments being described.

Figure 6:
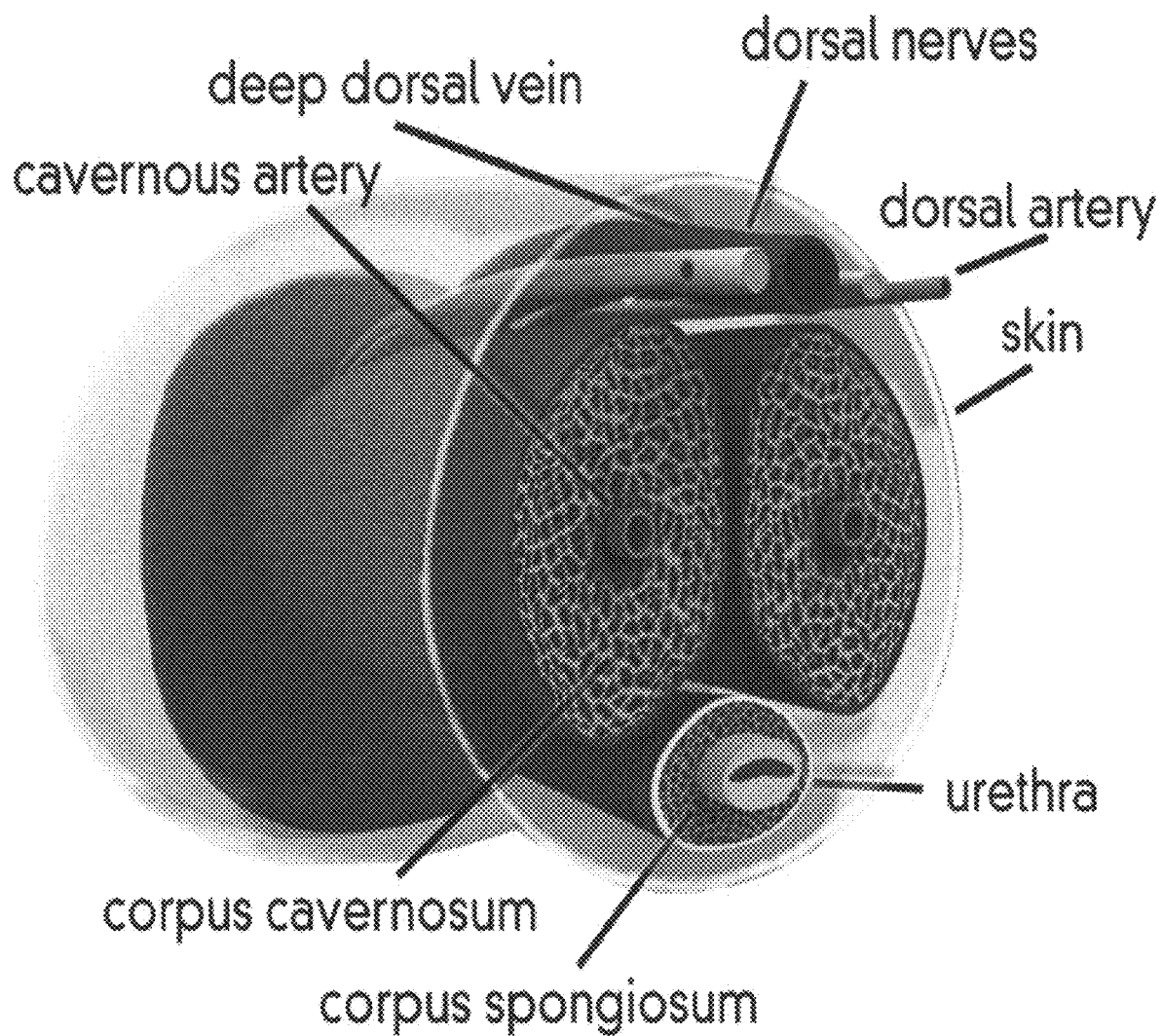
FIG. 6 depicts a cross section view of a penis.
Figure 7:
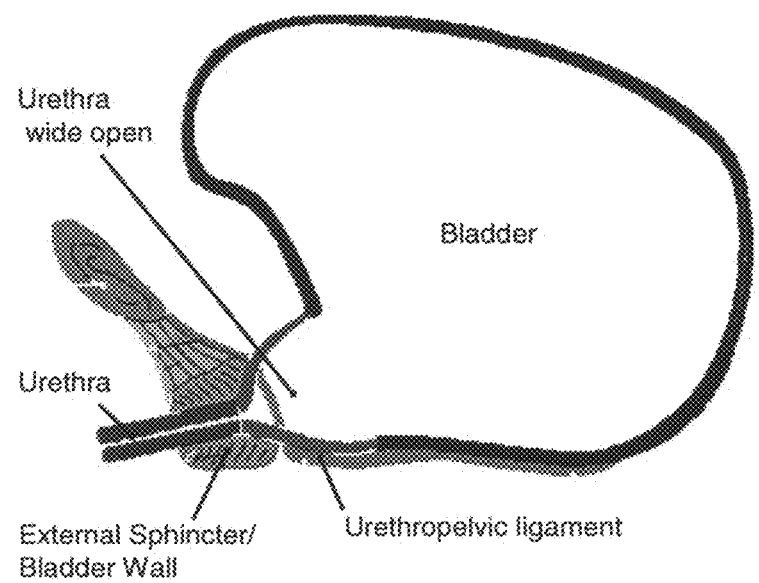
FIG. 7 depicts cross section views a bladder and the surrounding anatomy with and without particles.
Figure 7:
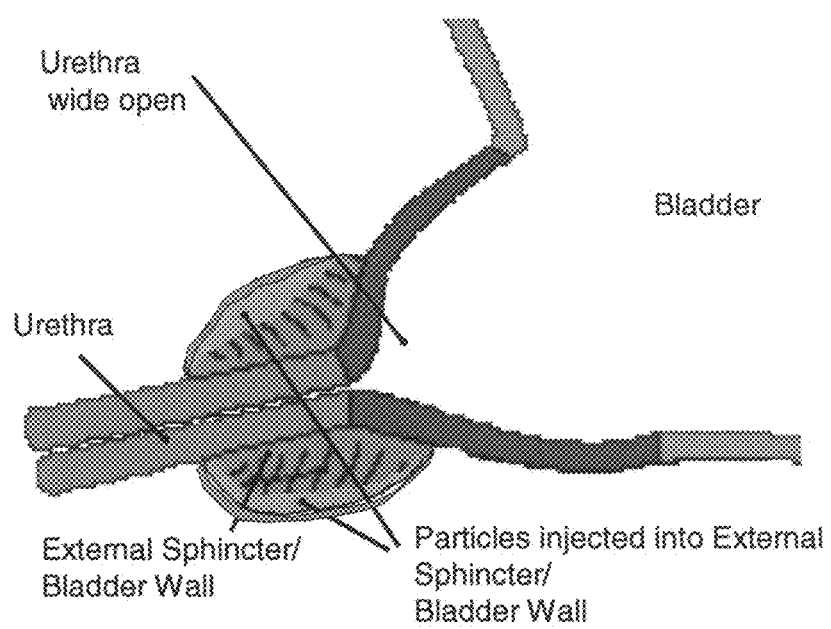
Figure 8:
FIG. 8 depicts a time sequence of injections into the lower bladder illustrating the first injection in the top picture and the final injection in the bottom picture.
Figure 8:
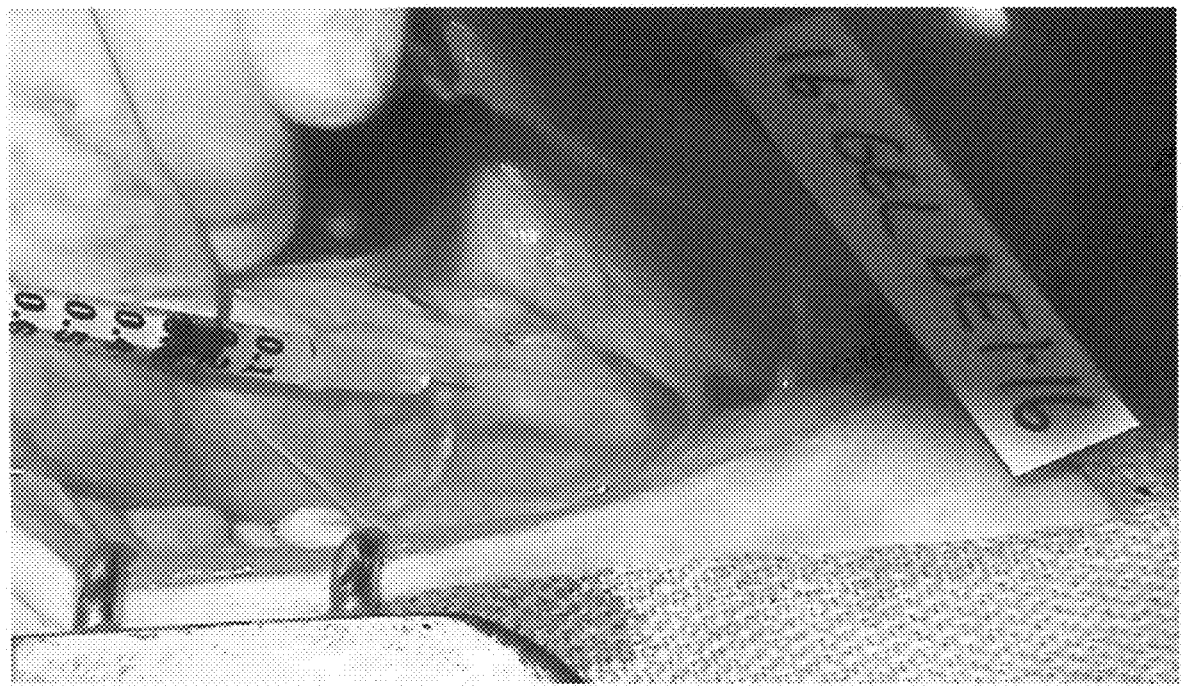
Figure 9:
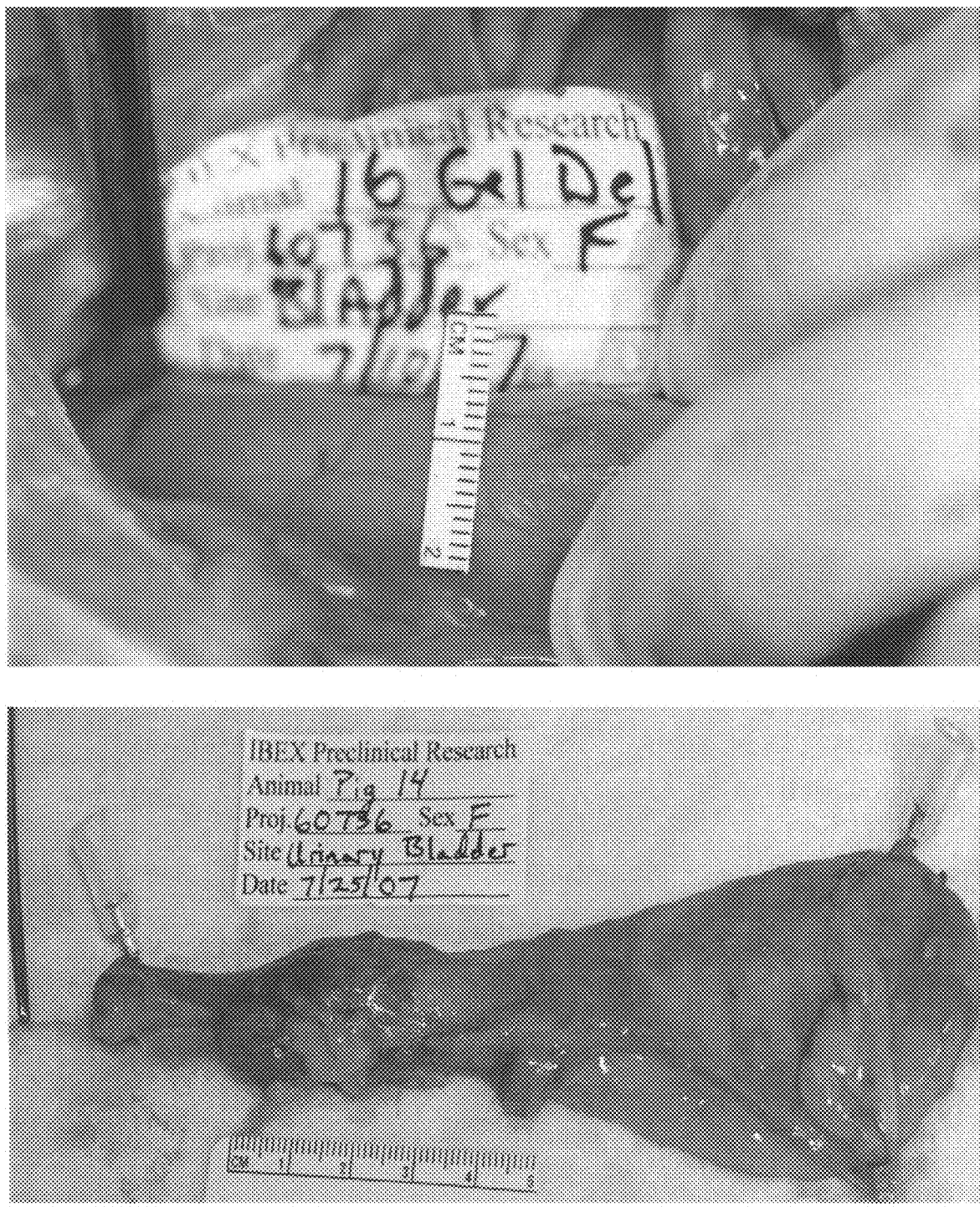
FIG. 9 depicts the lower bladder six weeks after injection still attached in the top picture and dissected in the bottom picture.
Figure 10:
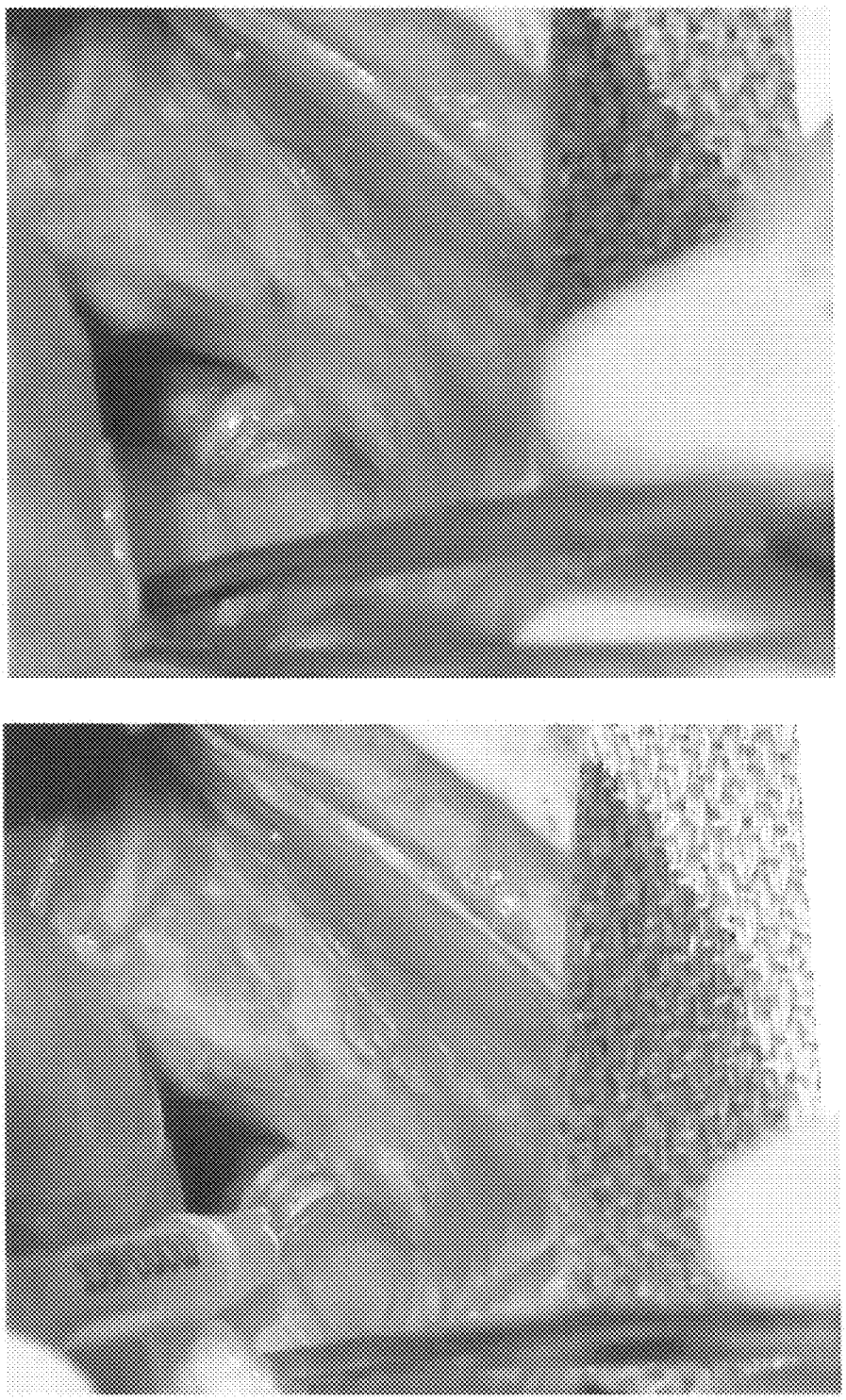
FIG. 10-12 depicts a time sequence of injections into the lower bladder illustrating pre-injection in top picture of FIG. 10, first injection in the bottom picture of 10, second and third injections in top and bottom pictures of FIG. 11 and final injections in top and bottom pictures of FIG. 12.
Figure 11:
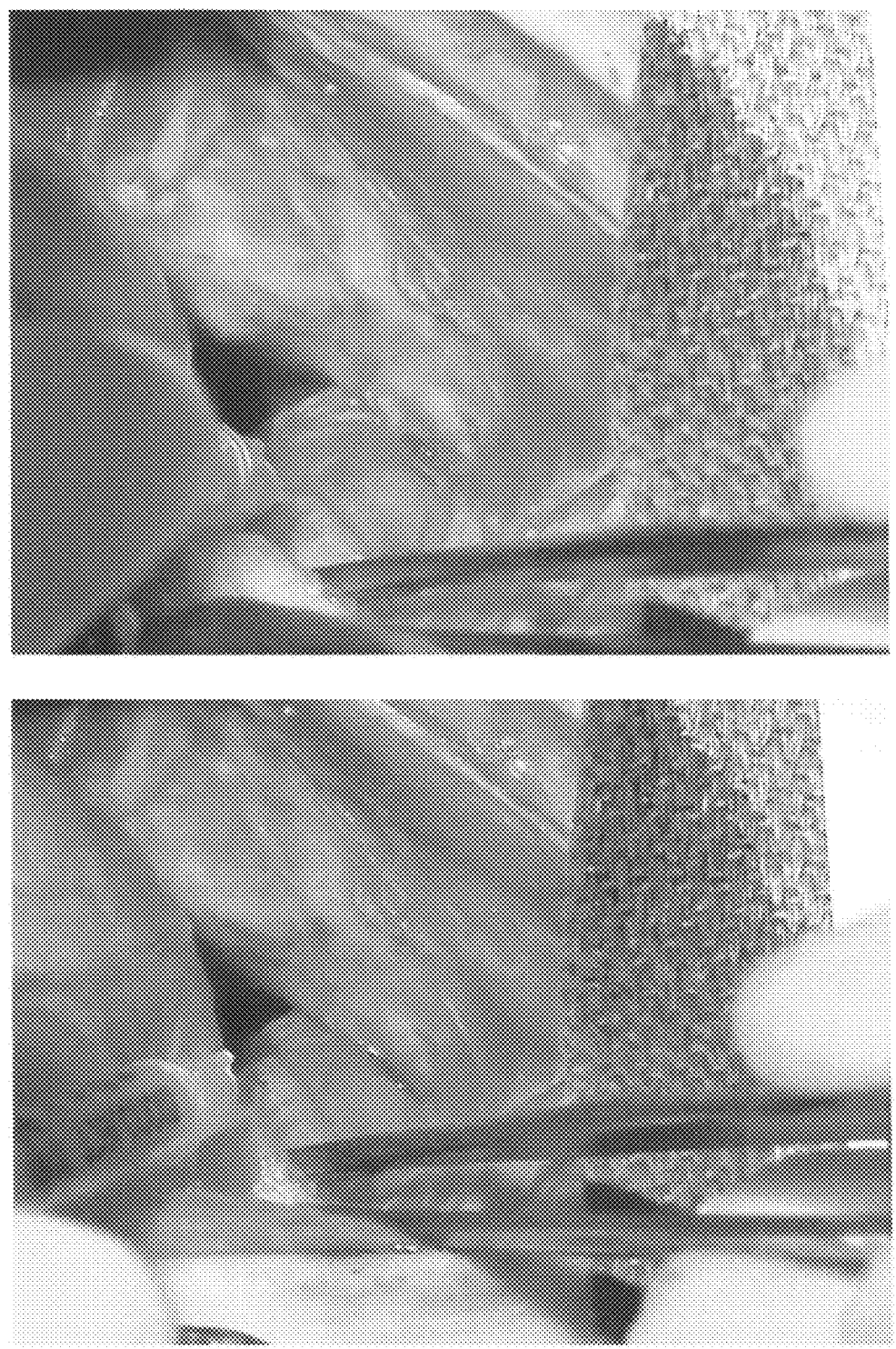
Figure 12:
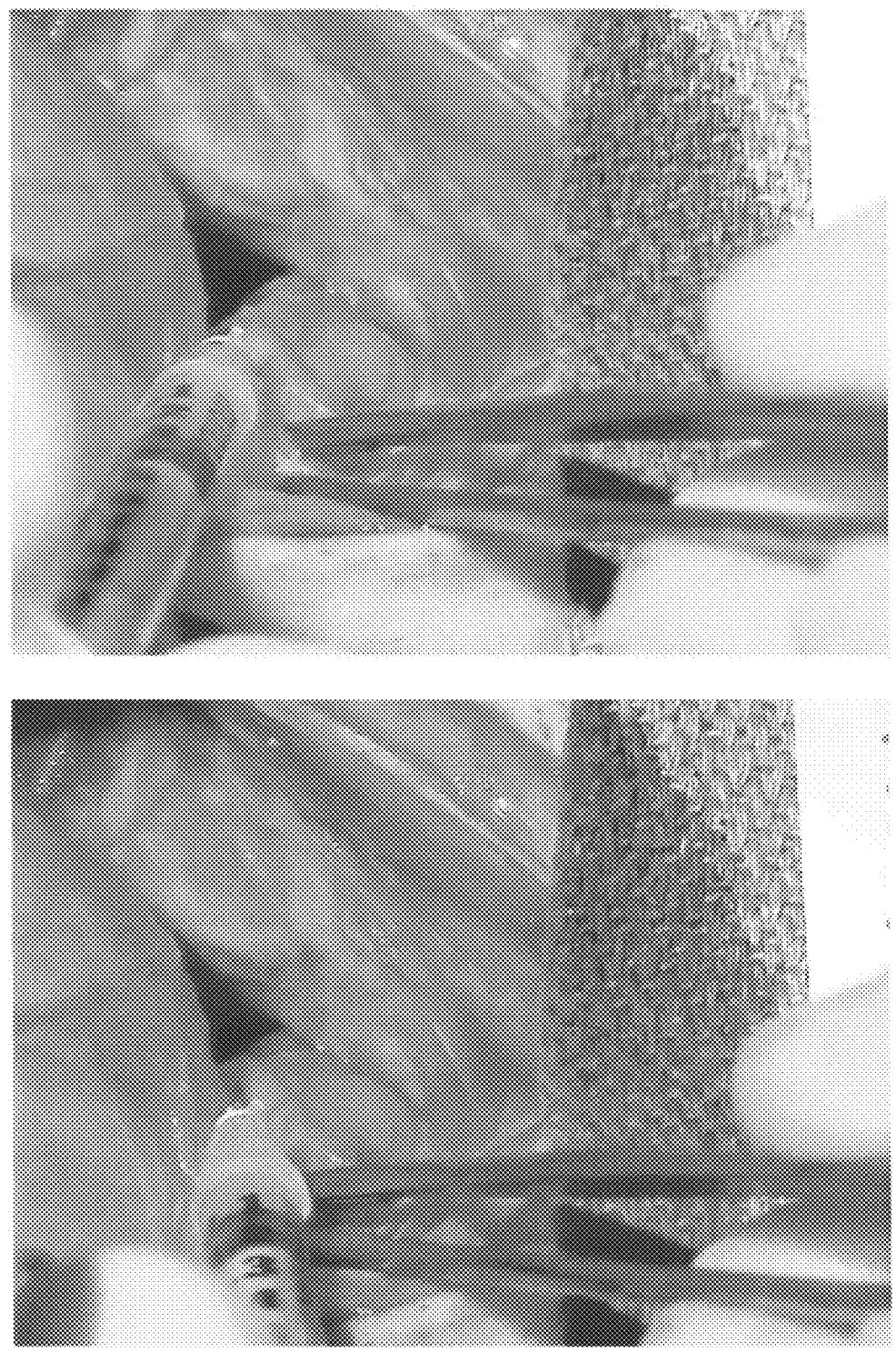

Method of Repairing or Enhancing the Function of an Organ Wall:

The present invention includes the methods of administrating the protein-base particles to, into or around the wall of an organ to either repair the wall and/or enhance the functionality of the organ by enhancing the wall (e.g. bulking the wall and/or promoting cellular activity that heals, reconstitutes or remodels the wall). Such a process may be used as a treatment for correcting degeneration, trauma and disease states of an organ (e.g. peyronies, incontinence, aging, genetic disorders . . . ). Organs that may be treated or enhanced with the particles include, but are not limited to the bladder, lips, throat, vagina, penis, urethra, throat (e.g. esophegous, trachea . . . ), stomach, rectum, gums, brain (e.g. parenchyma, meninges . . . ). In operation, the particles are administered, surgically or through injection, into the wall or into the muscle and/or tissue adjacent to the wall of the organ. For example, the particles of the present invention may be injected intradermally and/or subcutaneously into the penis, such as into the interstitial spaces around the urethra, the corpus spongiosum, corpus cavernosum or their surrounding tissues of a penis. An illustration of a cross section of a penis is depicted in FIG. 6. In an additional example, a therapeutic amount of the protein-based material (e.g. a biomaterial that includes one or more biocoacervates) can be injected into the wall of the bladder, such as the bladder wall surrounding the sphincter muscle or urethra or directly into the sphincter muscle or tissue surrounding the sphincter muscle or urethra of the bladder. Illustrations of the bladder/urethra and the adjacent components and tissues with and without particles of the present invention are depicted in FIG. 7. In still another example, a therapeutic amount of the protein-based material (e.g. a biomaterial that includes one or more biocoacervates) can be injected into the lips to provide a bulking function in this organ.

Generally, a therapeutic amount of the protein based material administered is determined by the amount that would bring the biological function back to a normal state or the amount that provides the desired biological effect. For example, in various embodiments of the present invention, the amounts administered to the organ wall or surrounding muscle or tissue will generally be approximately 0.5 cc to 10 cc; in other embodiments 0.8 cc to 6 cc; an in other embodiments 2 cc to 4.5 cc. In various embodiments of the present invention, the administration of a therapeutic amount of the protein-based material acts as a bulking agent and/or promotes the remodeling of the wall tissue or the tissue surrounding the wall; for example the lumen wall of the urethra or nearby tissues of the urethra. The adjacent tissue can include the muscle tissue, connective tissue and surrounding supportive tissues.

One method of enhancing the function of an organ or the method of administering a bulking material to enhance the function of an organ may be performed by the following steps:
  providing a syringe including a 12-32 gauge needle or other particle applicator filled with approximately 0.5 cc to 10 cc of a protein based material; and
  injecting in the organ wall or adjacent muscle or tissue surrounding the organ wall a therapeutically effective amount of the protein based material.

This method may be utilized on a variety of organs including, but not limited to the bladder, larynx, skin, mammary gland, lips, vagina, penis, testicles, brain and urethra.

A case study evaluating the particles utilized as a bulking agent injected into the sphincter muscle of the bladder wall or surrounding tissue was performed in June 2007. The processes and findings of the study are included below and pictures of two animals are showing the various stages of injection are depicted in FIGS. 8-9 and 10-12, respectively.
Bladder Case Study:
Purpose
  The purpose of this study was to evaluate the ability of an injectable test article to thicken the urinary bladder sphincter muscle wall.
Experimental Design
  The experimental design was as follows: 3 healthy adult White cross bred pigs were anesthetized per protocol. Each animal received a minimum of four (4) injections of the test article, UroLife (i.e. biocoacervate protein based particles), Pilot Study of a Unique Tissue Filler, Lot Number 012430, into the sphincter muscle of the urinary bladder on Day 0 of the study. The animals were observed for 2, 4 or 6 weeks (Table A), and at the end of their scheduled duration the animals were euthanized and the test implant sites were explanted.

All tissues were fixed in 10% neutral buffered formalin. Hematoxylin and eosin (H&E) stained sections of the implant sites were prepared by the Histology Laboratory from all animals. A veterinary pathologist microscopically evaluated H&E stained tissue sections.
Test Article Identification: UroLife, Pilot Study of a Unique Tissue Filler, Lot Number 012430

TABLE A

Study Design

| Animal Number | Duration | Implanted Material |
|---|---|---|
| 14 | 2 Weeks | UroLife, Pilot Study of a Unique Tissue Filler, Lot Number 012430 |
| 15 | 4 Weeks | |
| 16 | 6 Weeks | |

Results
  There were six slides (A-F) from each animal and each slide contained one to two transverse sections of urinary bladder
UroLife Pilot Study of a Unique Tissue Filler Lot Number 012430-2 Week Test Implant Sites (Table 1):
  The implant site was identified and scored in six slides.
  The urinary bladder wall (from the mucosa to the adventitia) of all six sections of the test implant site was focally thickened by a several large tightly and loosely packed masses of test material divided, surrounded, and multifocally infiltrated by variable numbers of inflammatory cells and fibrous connective tissue. The inflammatory cells consisted of multinucleated giant cells, macrophages, heterophils, lymphocytes, and/or plasma cells. Admixed with the test material were small foci of fibrin deposits, protein fluid, hemorrhage, necrotic cellular debris, and scattered rare fragments of clear refractive material surrounded by or engulfed by macrophages and multinucleated giant cells. Scattered macrophages and some areas of the test material contained hemosiderin or hematoidin. There was a thin layer of dark basophilic mineralized material multifocally on the mucosa. Within the adventitial layer were several small to large foci of test material admixed and surrounded by the tissue reaction mentioned above, with the exception that lymphocytes were the predominant inflammatory cell. One to several of the large nests of test material had a large area of central cavitation, and the test material focally extended to the basal layer of the mucosa, and the overlying mucosa was eroded. There were scattered and/or small foci of lymphocytes and plasma cells in the lamina propria adjacent to the implant site that occasionally extended into the mucosa. Where the inflammatory cells extended into the mucosa, the mucosa was degenerating and eroded.

The average thickness of the urinary bladder from the mucosa to the outer muscle layer, including the test material in the measurement (Table 5) was 5586. The average thickness of the urinary bladder from the mucosa to the outer muscle layer, without the test material in the measurement (Table 6) was 1288.

Inflammation: Inflammation consisted of macrophages, heterophils, lymphocytes, and multinucleated giant cells. All six sections of the test implant site contained a mild to moderate amount of multinucleated giant cells, a mild amount of lymphocytes and macrophages, and a minimal amount of heterophils. Eosinophils, mast cells and plasma cells were not found in any of the six sections of the test implant site.

Tissue Response: All six sections of the test implant site contained a mild to moderate amount of tissue in growth into the device, and a minimal amount of fibroplasia, neovascularization, hemorrhage, and foreign debris other than the implant. There was a minimal amount of necrosis in three sections and mineralization in two sections of the test implant site. Granulation tissue, granulomas, myofiber necrosis/degeneration, and myofiber regeneration were not found in any of the six sections of the test implant site. The Average Test Mean Reaction Zone in Microns was 252. UroLife, Pilot Study of a Unique Tissue Filler, Lot Number 012430-4 Week Test Implant Sites (Table 2):

The implant site was identified and scored in five of six slides.

The lamina propria and submucosa were thickened by mature fibrous connective tissue with small numbers congested blood vessels, lymphocytes and fewer plasma cells, heterophils and macrophages in the lamina propria. There was a moderate amount of hemorrhage within the connective tissue surrounding the urinary bladder, and several small foci of lymphocytes and/or hemosiderin-laden macrophages also in the connective tissue surrounding the urinary bladder.

The urinary bladder wall (from the mucosa to the adventitia) in all five sections of the test implant site was focally to multifocally thickened by a several large tightly and loosely packed masses of test material divided, surrounded, and multifocally infiltrated by variable numbers of inflammatory cells and fibrous connective tissue. There were moderate numbers of macrophages and multinucleated giant cells with fewer fibroblasts and heterophils immediately surrounding and minimally to mildly infiltrating the test material. A thick layer of fibrous connective tissue, fibroblasts, lymphocytes, and small numbers of plasma cells then encircled these inflammatory cells (granulomatous reaction). There were one to two small foci of the connective tissue and chronic inflaimmation surrounding several multinucleated giant cells containing small fragments of clear refractive unknown material in the tissue adjacent to the larger test material nests. Small fragments of this same clear material surrounded by a multinucleated giant cell were scattered in the larger test material nests. Several small areas of the test material were mineralizing, and small numbers of macrophages, especially adjacent to the test material foci, contained hemosiderin. The lamina propria and submucosa above or adjacent to the implant sites were thickened with mature connective tissue, small numbers of chronic inflammation and congested blood vessels. One of the nests of test material in three slides (A, B and C) contained a large mass of test material partially admixed with many red blood cells, macrophages, heterophils, and multinucleated giant cells. The implant site on slide E was mainly within the muscle and adventitial layer of the urinary bladder. There was a small thin layer of cellular debris on the surface of the mucosa in slide C, above where the implant site was within the wall of the urinary bladder.

The average thickness of the urinary bladder from the mucosa to the outer muscle layer, including the test material in the measurement (Table 8) was 4992. The average thickness of the urinary bladder from the mucosa to the outer muscle layer, without the test material in the measurement (Table 9) was 2086

Inflammation: Inflammation consisted of macrophages, heterophils, lymphocytes, multinucleated giant cells, and plasma cells. All five sections of the test implant site contained a moderate to marked amount of lymphocytes and macrophages, a mild amount of multinucleated giant cells, a minimal to mild amount of heterophils, and a minimal amount of plasma cells. Eosinophils and mast cells were not found in any of the five sections of the test implant site Tissue Response: All five sections of the test implant site contained a moderate to marked amount of fibroplasia, a minimal to mild amount of neovascularization and tissue in growth into the device, and a minimal amount of mineralization and foreign debris other than the implant. Four sections of the test implant site had a minimal amount of hemorrhage. Necrosis, granulation tissue, granulomas, myofiber necrosis/degeneration, and myofiber regeneration were not found in any of the five sections of the test implant site. The Average Test Mean Reaction Zone in Microns was 453. UroLife, Pilot Study of a Unique Tissue Filler, Lot Number 012430-6 Week Test Implant Sites (Table 3):

The probable implant site was identified and scored in three of the six slides. None of the inflammatory reactions found in the three sections of the probable test implant site contained test material, but the remaining inflammatory reaction is thought to be from degradation and resorption of the test material and/or from the unknown clear refractive material (described in the other animals and below) remaining within the inflammation. There was no implant site found in the tissue sections on slides D, E and F. The lamina propria and submucosal tissue was thickened by mature connective tissue, scattered lymphocytes, an occasional hemosiderin-laden macrophage, and prominent blood vessels. There was a small focus to hemorrhage within the connective tissue surrounding the urinary bladder, and an occasional small focus of chronic inflammation within or adjacent to the outer muscle wall of the urinary bladder.

Focally to multifocally within the lamina propria and submucosal layer of the urinary bladder (in all three tissue sections), there were several small to moderate foci of maturing fibrous connective tissue admixed with chronic inflammation The inflammatory cells consisted predominately of lymphocytes and macrophages with fewer numbers of multinucleated giant cells and an occasional heterophil Most of the multinucleated giant cells were surrounding a small fragment of the clear refractive unknown material, and many of the macrophages contained intracytoplasmic hemosiderin The chronic inflammation in the lamina propria and submucosa extended to the basal layer of the mucosa The lamina propria and submucosa of the tissue sections on slide C were diffusely mildly to moderately thickened by mature connective tissue admixed with small numbers of scattered lymphocytes and prominent blood vessels.

The average thickness of the urinary bladder from the mucosa to the outer muscle layer, including the test material in the measurement (Table 11) was 3337. The average thickness of the urinary bladder from the mucosa to the outer muscle layer, without the test material in the measurement (Table 12) was 3141.

Inflammation: Inflammation consisted of macrophages, heterophils, lymphocytes, and multinucleated giant cells. All three sections of the test implant site contained a mild amount of lymphocytes and macrophages, and a minimal number of multinucleated giant cells There were minimal numbers of heterophils in two sections of the test implant site Eosinophils, mast cells and plasma cells were not found in any of the three sections of the test implant site.

Tissue Response: All three sections of the test implant site contained a mild to moderate amount of fibroplasia, a mild amount of foreign debris other than the implant, and a minimal amount of neovascularization. There was a minimal amount of hemorrhage within one section of the test implant site. Necrosis, granulation tissue, mineralization, granulomas, myofiber necrosis/degeneration, and myofiber regeneration were not found in any of the three sections of the test implant site. The Average Test Mean Reaction Zone in Microns was 282

Discussion

2 Week Implant Site—There were large amounts of test material surrounded and multifocally infiltrated by a chronic inflammatory reaction. Occasionally, the inflammation of the implant site infiltrated into the mucosal layer, causing erosion of the mucosa. Scattered throughout the test material and tissue reaction were small fragments of clear refractive unknown material, that is thought to have been introduced into the implant site when the test material was injected into the urinary bladder wall. There were small deposits of hemosiderin and hematoidin, from earlier hemorrhage within the implant site, within the test material and macrophages, and small areas of chronic inflammation, without test material, adjacent to the implant site. These small areas of inflammation are likely an extension of the tissue reaction of the implant site, but at a different angle than which the sample was taken.

The tissue sections of this animal had a thin layer of mineralized material covering the surface of the mucosa. This mineralized material is occasional found grossly in the urinary bladder of pigs and is considered an incidental finding and not related to implantation of the test article into the wall of the urinary bladder.

Several nests of the test material within the tissue sections had large areas of central cavitation This change is from histology processing of the tissues.

4 Week Implant Site—The tissue sections of this animal still had large deposits of the test material, surrounded by a prominent granulomatous tissue reaction. One tissue section had a small thin layer of cellular debris covering the surface of the mucosa, which is where the inflammation of the implant site likely infiltrated the entire layer of the mucosa. There were also small fragments of clear refractive unknown material scattered throughout the test material and tissue reaction in this animal, as found in the 2 Week animal Some of the macrophages were hemosiderin-laden, from earlier hemorrhage within the implant site.

Though there was no implant site found in one of the tissue sections of this animal, there was a multifocal to diffuse thickening of the lamina propria and submucosa in all six tissue sections. This thickening was accompanied by small amounts of chronic inflammation that could be minimal extensions of the inflammation surrounding the implant site in the adjacent tissue, or unrelated to the implanted test material and just a normal immunologic reaction. The thought is that this section of tissue was taken either too far proximal or distal to the implant site to have the tissue reaction or implanted material in the tissue section.

6 Week Implant Site—Three of the tissue sections had a tissue reaction within the lamina propria and submucosa, but none of the tissue sections from this animal contained test material. Within the tissue reaction found in the three sections were mild amounts of the same clear refractive unknown material mentioned above. It is not known if the tissue reaction found in the three tissue sections is a result of previous but degraded and resolved test material within the tissue, or is just a reaction to the unknown material.

Though there was no implant site found in all of the tissue sections of this animal, there was a multifocal to diffuse thickening of the lamina propria and submucosa in all six tissue sections. This thickening was accompanied by small amounts of chronic inflammation that could be minimal extensions of the inflammation surrounding the implant site, or unrelated to the implanted test material and just a normal immunologic reaction. The thought that there is no implanted material or residual tissue reaction in these three section is from removal of the test material and a decrease in the amount of tissue reaction to the residual material within the implant site. When the tissue sections were taken for these three sections (without tissue reaction or implant site), the cuts were taken either too far proximal or distal to the remaining tissue reaction found in the other three tissue sections.

There were small foci of minimal chronic inflammation within the outer muscle layer of the urinary bladder in a few of the tissue sections of this animal. This inflammation is thought to be an incidental finding and not related to the implanted test material. The hemorrhage found in the connective tissue surrounding the urinary bladder in three of the tissue sections is from histology processing of the tissues.

Urinary Bladder Wall Thickness—2 to 6 Weeks (Table B)

There was a difference in the thickness of the lamina propria and submucosa from the 2 week animal to the 6 week animal. The 2 week animal had an average thickness of the urinary bladder wall of 5586, including the test material (with tissue reaction), and a thickness of 1288 without the test material. The 4 week animal had an average thickness of the urinary bladder wall of 4992, including the test material (with tissue reaction), and a thickness of 2086 without the test material. The 6 week animal had an average thickness of the urinary bladder wall of 3337, including the test material (with tissue reaction), and a thickness of 3141 without the test material.

The difference found in the thickness of the wall, including the implant site and tissue reaction to the implanted material, from 2 to 6 weeks would be due to the amount of test material and tissue response reacting to the test material. In the 2 week tissue sections there were large amounts of inflammation surrounding the implant site, and in the 4 week tissue sections, the inflammation is more organized. (The 6 week measurements of the thickness of the wall with the test material may be false because there was no test material found in the tissue sections, just tissue reaction.) The smaller number for the thickness of the urinary bladder wall in the 6 week animal is because the tissue reaction in the tissue sections is resolving.

The difference in the thickness of the urinary bladder wall, in the areas that did not contain test material or a tissue reaction to the test material, was due to a normal thickness of the wall of the urinary bladder in the 2 week animal, and then an increase in mature fibrous connective tissue within the lamina propria and submucosa in the 4 and 6 week animals.

Conclusion

Under the conditions of this Pilot Study for the Evaluation of a Unique Tissue Filler When Injected into the Sphincter Muscle of the Urinary Bladder, there was a prominent chronic inflammatory tissue reaction when the test article, UroLife, Pilot Study of a Unique Tissue Filler, Lot Number 012430, was injected into the wall of the urinary bladder, at the level of the sphincter muscle, in swine. The test material was found in the implant sites at 2 and 4 weeks, but not found in the 6 week tissue sections. The tissue response was surrounding and infiltrating the test material in the 2 and 4 week animals, but the tissue reaction was more organized in the 4 week animal. Of the tissue reactions found in the 6 week animal, a tissue response was found in three of the six tissue sections and consisted of a resolving tissue reaction without test material.

The lamina propria and submucosa in the 4 and 6 week animals were thickened by fibrous connective tissue with prominent blood vessels and small foci of chronic inflammation The 6 week animal had a thicker lamina propria and submucosa (in the areas without the implant site), than the 4 week animal This is thought to be from larger amounts of fibrous connective tissue admixed with prominent blood vessels deposited in the lamina propria and submucosa in the 6 week animal.

disc gel/fluid and/or promoting cellular activity that heals, reconstitutes or remodels the disc). In operation, the particles are administered, surgically or through injection, into the disc to act as a bulking agent and/or promote the remodeling, reconstitution or repair of the disc tissue and/or internal fluid/gel within.

Figure 13:
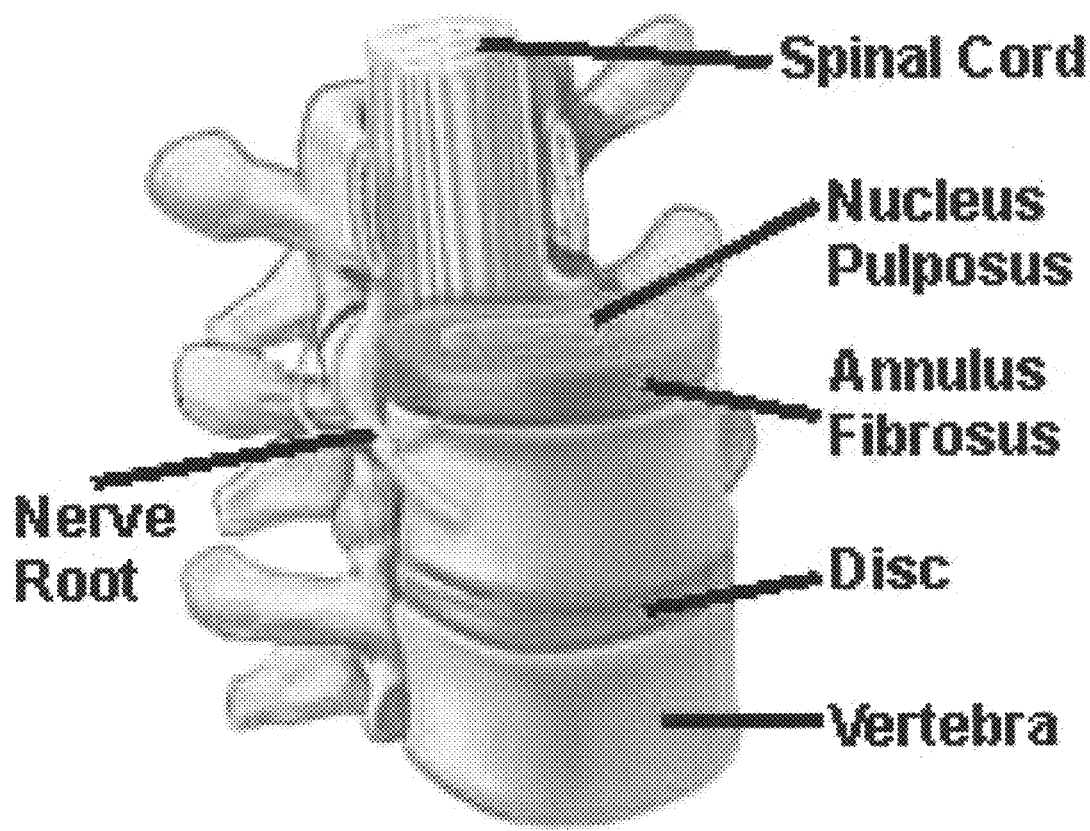
FIG. 13 depicts a diagram of a spinal column.
Figure 14:
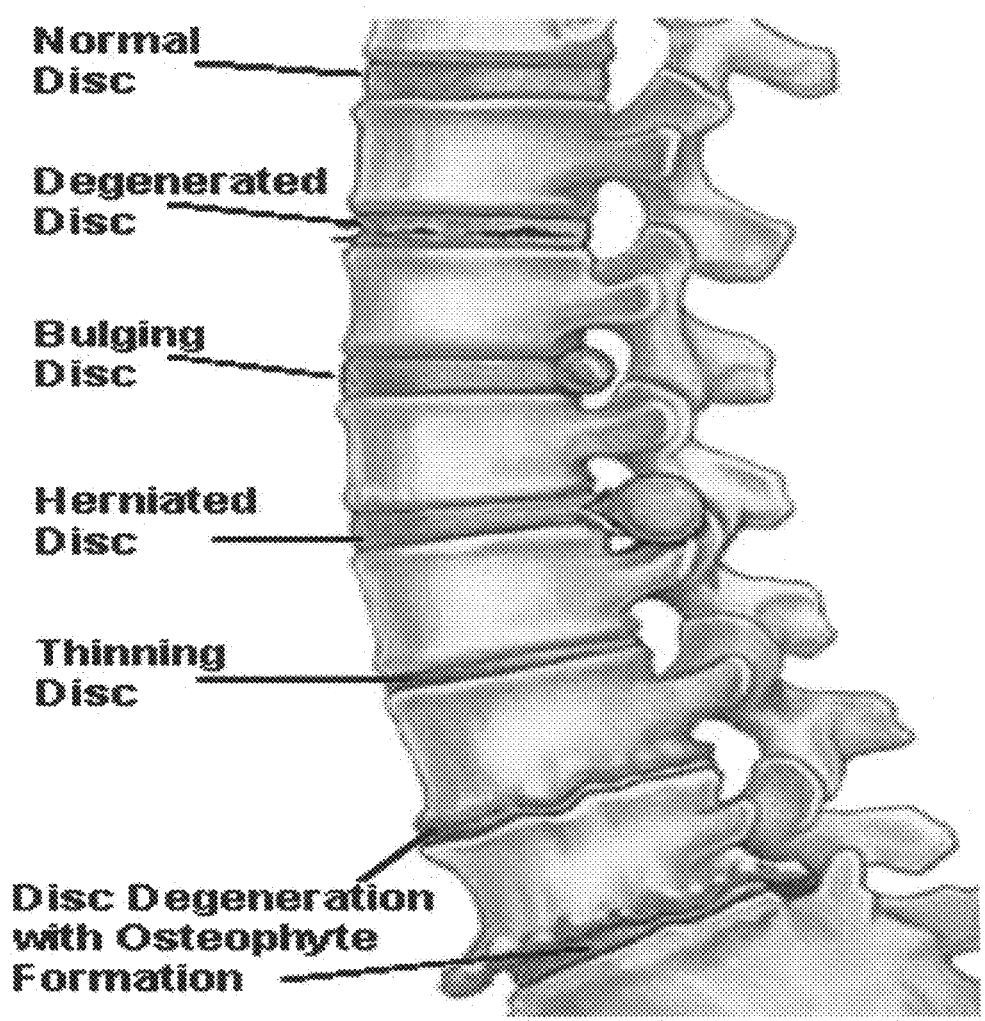
FIG. 14 depicts a diagram of a spinal column illustrating examples of spinal disc problems.

In one embodiment of the present invention, a therapeutically effective amount of the protein-base particles are injected into the disc of a patient. In various embodiments the injection is into the nucleus pulposus of the vertebral disc. This is accomplished by inserting the syringe needle (e.g. 23 ga, long needle) through the annulus fibrosis and depositing the contents within the nucleus pulposus. A figure depicting the features of the spine is depicted in FIG. 13. Correct placement of the needle tip in the nucleus is assessed by considering the needle length and angle of injection, to ensure the needle tip would be centered in the nucleus. The pressure needed to deploy the protein-base particles into the nucleus pulpous increases as more particles are injected, indicating that a defined space is being filled. The nucleus puposus and the annulus fibrosis can both be repaired or enhanced by injecting particles into these parts of the disc. Such a method can be utilized to treat spinal inflictions, such as degenerating discs, thinning of the discs, herniated discs, bulging discs and osteophyte formation. FIG. 14 illustrates a few of these inflictions.

Generally, a therapeutically effective amount of the protein based material administered is determined by the

TABLE B

Averages of the 2, 4 and 6 week Animals

| | ANIMAL # TEST IMPLANT SITE | | |
|---|---|---|---|
| | Average of all the 2 Week Implant Sites | Average of all the 4 Week Implant Sites | Average of all the 6 Week Implant Sites |
| INFLAMMATION (I) | | | |
| Heterophils/Neutrophils | 1 | 1 | 1 |
| Eosinophils | 0 | 0 | 0 |
| Mast Cells | 0 | 0 | 0 |
| Lymphocytes | 2 | 3 | 2 |
| Plasma Cells | 0 | 1 | 0 |
| Macrophages | 2 | 3 | 2 |
| Multinucleated Giant Cells | 3 | 2 | 1 |
| SUBTOTAL | 8 | 10 | 6 |
| TISSUE RESPONSE (TR) | | | |
| Necrosis | 1 | 0 | 0 |
| Granulation Tissue | 0 | 0 | 0 |
| Fibroplasia/capsule | 1 | 3 | 2 |
| Neovascularization | 1 | 2 | 1 |
| Mineralization | 0 | 1 | 0 |
| Granulomas | 0 | 0 | 0 |
| Myofiber Necrosis/Degeneration | 0 | 0 | 0 |
| Myofiber Regeneration | 0 | 0 | 0 |
| Hemorrhage | 1 | 1 | 0 |
| Tissue In growth into Device | 2 | 2 | NA |
| Foreign Debris (other than implant) | 1 | 1 | 2 |
| SUBTOTAL | 7 | 10 | 6 |
| TOTAL (I + TR) | 15 | 20 | 11 |
| Psuedo-Bursal Cavity* | — | — | — |
| Mean Rx Zone in Microns[A] | 252 | 453 | 282 |
| Average Thickness of the Urinary Bladder Wall (μm) with Test Material | 5586 | 4992 | 3337 |
| Average Thickness of the Urinary Bladder Wall (μm) without Test Material | 1288 | 2086 | 3141 |

Method of Repairing or Enhancing the Spinal Disc:

The present invention includes the methods of administrating the protein-base particles into a disc in the spine to either repair the disc and/or enhance the functionality of the disc (e.g. replacing the deteriorated disc tissue or internal amount that would bring the biological function back to a normal state or the amount that provides the desired biological effect. For example, in various embodiments of the present invention, the amounts administered to a spinal disc, including the nucleus puposus and/or annulus fibrosis will generally be approximately 0.2 cc to 5 cc; in other embodiments 0.3 cc to 2 cc; an in other embodiments 0.5 cc to 1 cc. In various embodiments of the present invention, the administration of a therapeutic amount of the protein-based material acts as a bulking agent and/or promotes the remodeling of the disc. The bulking agent can act as a cushion or shock absorber for the spinal discs.

One method of treating or enhancing the function of a spinal disc or the method of administering a bulking material to enhance the function of a spinal disc may be performed by the following steps:

providing a syringe including a 12-32 gauge needle or other particle applicator filled with approximately 0.2 cc to 5 cc of a protein based material; and injecting in the spinal disc a therapeutically effective amount of the protein based material.

This method wherein the protein-based material is injected in a nucleus puposus and/or annulus fibrosis of the spinal disc.

A case study evaluating the particles utilized as a bulking agent injected into the spinal disc was performed in October, 2007. The findings of the study are included below and a picture of the device and section of spine tested is depicted in FIG. 15.

Figure 15:
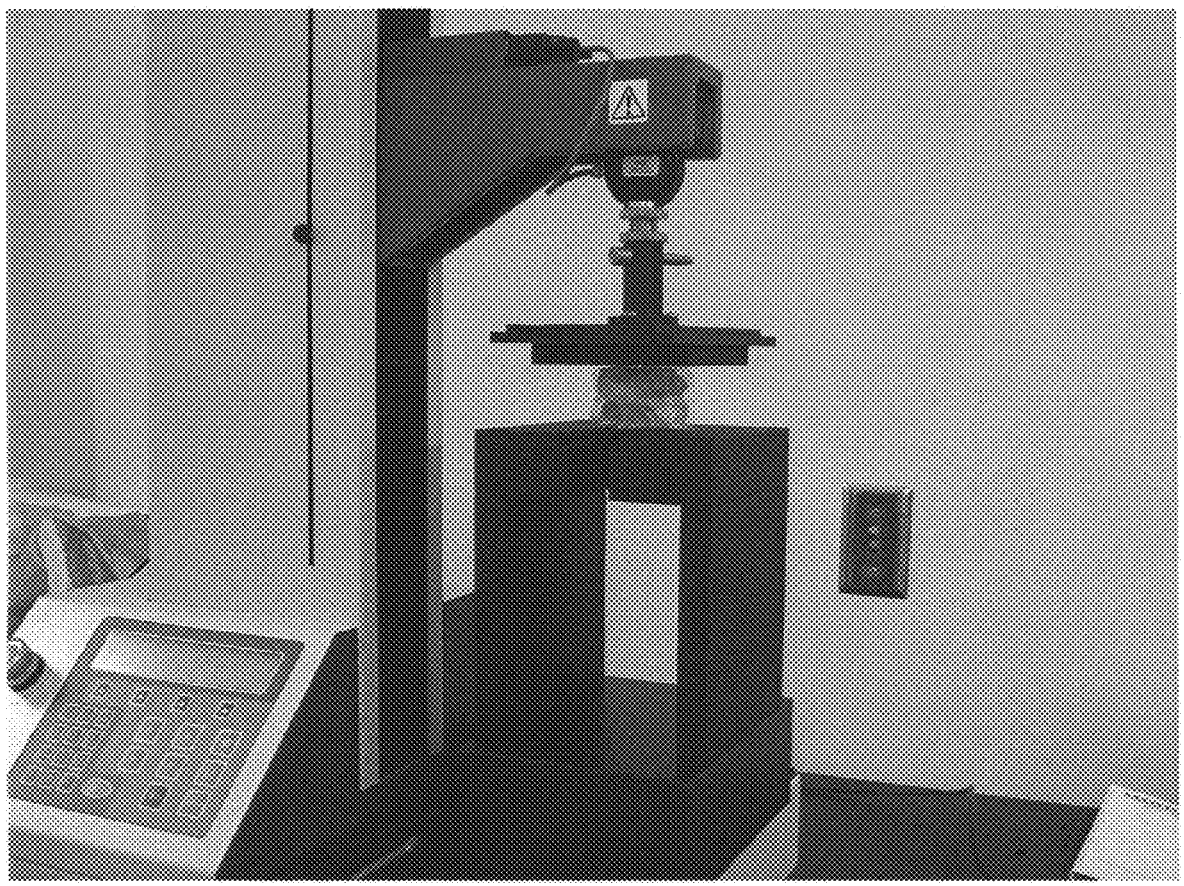
FIG. 15 depicts a photograph of a force testing apparatus testing a spinal disc intact between two vertebrae covered in a plastic wrap.

Spinal Disc Case Study (Injection of Spinal Discs with Protein-Based Particles (DiscLife)):

Notes:

Compression (in mm) of vertebral disc with 70N of force applied (10N to 80N) *All tests performed at room temperature Picture of set-up depicted in FIG. 15

Made two more injections of biocoacervate protein based particles (DiscLife) (#4 & #5) at different locations (dorsal side of disc)

Mean deflection and stiffness did not change significantly after injection #4—approx 1.06 mm and 1650 Mpa (4-5 test runs)

Mean deflection fell just below 1.0 mm (approx mean of 0.95 mm) after injection #5, but stiffness did not appear to change (4 runs)→indicates full cavity After manipulation of sample (injection and moving from test plate), first test upon repositioning generally is an outlier (deflection tests high and stiffness lower) several tests must be run subsequently for data to run consistently.

Pre-Test:

|   | Deflection | Modulus |   |
|---|---|---|---|
| 1 | 1.3106 | 1119.2 | *Compression (in mm) of vertebral disc with 70N of force applied (10N to 80N) |
| 2 | 1.3374 | 960.7 | *Pre-injection samples |
| 3 | 1.2054 | 1101.7 |   |
| 4 | 1.2775 | 1122.4 |   |
| 5 | 1.2968 | 1130.3 |   |
| mean | 1.286 | 1086.860 |   |
| stdev | 0.050 | 71.296 |   |
| cv % | .039 | 0.066 |   |

Injection 1:
After 0.11 cc injection of Biocoacervate Protein Based Particles (i.e. DiscLife) (Lot #012430)

|   | Deflection | Modulus |
|---|---|---|
| 1 | 1.2921 | 604.9 |
| 2 | 1.2462 | 1117.8 |
| 3 | 1.1859 | 1084.2 |
| 4 | 1.1484 | 1505 |
| 5 | 1.1774 | 1029.1 |
| mean | 1.2100 | 1068.20 |
| stdev | 0.058 | 320.034 |
| cv % | 0.048 | 0.300 |
| p-value (w/pretest) | 0.05831 |   |

Injection 2:
After 0.1 cc injection of DiscLife

|   | Deflection | Modulus |
|---|---|---|
| 1 | 1.1175 | 1312.3 |
| 2 | 1.1224 | 1948.7 |
| 3 | 1.1326 | 1162.5 |
| 4 | 1.1379 | 1453.9 |
| 5 | 1.1813 | 1588.6 |
| mean | 1.13834 | 1493.2 |
| stdev | 0.025 | 300.089 |
| cv % | 0.022 | 0.201 |
| p-value (w/pre-test) | 0.00037 | 0.019 |

Injection 3:
After 0.2 cc injection on contralateral side of disc

|   | Deflection | Modulus |   |
|---|---|---|---|
| 1 | 1.1229 | 1668.6 |   |
| 2 | 1.0741 | 1720 |   |
| 3 | 1.0417 | 1649.9 |   |
| 4 | 1.0649 | 1773.9 |   |
| 5 | 1.0246 | 1521.5 |   |
| mean | 1.06564 | 1666.78 |   |
| stdev | 0.037 | 94.47 |   |
| cv % | 0.035 | 0.057 |   |
| p-value | 4.83E-05 | 4.276E-06 | to pre-test |
|   | 0.007 | 0.252 | to inj#2 |

Injection 6:
24 hrs after injection #5—overnight storage at 4 C

|   | Deflection | Modulus |   |
|---|---|---|---|
| 1 | 1.0502 | 1402.6 |   |
| 2 | 1.0917 | 1340.7 |   |
| 3 | 1.1203 | 1176.8 |   |
| 4 | 1.0219 | 2070.3 |   |
| 5 | 1.0212 | 1348.3 |   |
| mean | 1.06106 | 1467.74 |   |
| stdev | 0.044 | 347.27 |   |
| cv % | 0.041 | 0.237 |   |
| p-value | 6.53E-05 | 4.301E-02 | to pre-test |
|   | 0.863 | 0.251 | to inj#3 |

Conclusion of findings: The injection of the Biocoacervate Protein-based Particles of the present invention results in an decrease in the amount of deflection that occurs between the vertebrae and an increase in stiffness (modulus). This would indicate an enhancement of the spinal disc functionality from injections into the nucleus pulposus.

Injection of Spinal Discs with HCL:
Note: Pre-injection baseline

Upper Lower

|   | Deflection (mm) | Stiffness (N/m) | Stiffness (N/m) |
|---|---|---|---|
| 1 | 0.71709 | 124120 | 80605 |
| 2 | 0.72012 | 122030 | 80994 |
| 3 | 0.71974 | 115950 | 83765 |
| 4 | 0.72825 | 116720 | 80268 |
| 5 | 0.75417 | 109030 | 81515 |
| mean | 0.7279 | 117570 | 81429 |
| stdev | 0.015 | 5896.45 | 1385.68 |
| cv % | 0.021 | 0.05 | 0.017 |

Injection #1-0.2 ml HCl
Note: Test after 1 hr incubation w/HCl
Upper Lower

|   | Deflection | Stiffness | Stiffness |   |
|---|---|---|---|---|
| 1 | 0.80156 | 116310 | 68135 |   |
| 2 | 0.7988 | 121860 | 67736 |   |
| 3 | 0.83326 | 113050 | 67621 |   |
| 4 | 0.81852 | 107520 | 70075 |   |
| 5 | 0.81838 | 113910 | 69691 |   |
| mean | 0.8141 | 114530 | 68651.6 |   |
| stdev | 0.014 | 5210.859 | 1148.233 |   |
| cv % | 0.017 | 0.045 | 0.017 | to pre-inj |
| p-value | 0.00001 | 0A13 | 0.0000002 |   |

Note: Test after 4 hr incub
Upper Lower

|   | Deflection | Stiffness | Stiffness |   |
|---|---|---|---|---|
| 1 | 0.79627 | 113430 | 71355 |   |
| 2 | 0.80727 | 114990 | 72409 |   |
| 3 | 0.78902 | 116130 | 72661 |   |
| 4 | 0.80558 | 122030 | 68733 |   |
| 5 | 0.79304 | 114690 | 68676 |   |
| mean | 0.7982 | 116254 | 70766.8 |   |
| stdev | 0.008 | 3368.84 | 1945.416 |   |
| cv % | 0.01 | 0.029 | 0.027 | w/pre-inj |
|   |   | 0.68 | 0.00001 |   |

Note: Test after 21 hr incub
Upper Lower

|   | Deflection | Stiffness | Stiffness |   |
|---|---|---|---|---|
| 1 | 0.82331 | 120570 | 62810 |   |
| 2 | 0.85565 | 113360 | 65622 |   |
| 3 | 0.82963 | 121370 | 66600 |   |
| 4 | 0.85051 | 114100 | 63515 |   |
| 5 | 0.83183 | 114180 | 68214 |   |
| mean | 0.8382 | 116716 | 65352.2 |   |
| stdev | 0.014 | 3906.742 | 2216.855 |   |
| cv % | 0.017 | 0.033 | 0.034 | w/pre-ing |
| p-value | 2.32E−06 | 0.794 | 0.000001 |   |

Upper stiffness refers to the slope of a line approaching 80N **Lower stiffness refers to the slope of a line approaching 10N Conclusion of findings: HCL causes injury to the nucleus pulposus and annulus fibrosis resulting in increased deflection and reduced stiffness as soon as 1 hour following injection.

Method of Treating and/or Repairing a Joint:

The present invention includes the methods of administrating the protein-based particles into the joint, such as the synovial space, to repair, reconstitute or remodel the tissue, cartilage, ligaments and/or bone and/or enhance the functionality of the joint (e.g. replacing the deteriorated components present in the joint; promoting cellular activity that heals, reconstitutes or remodels the components of the joint; provides cushion or shock absorbing features to the joint; and/or provides lubricity to the joint). The joint may be any joint of the body including but not limited to the knee, hip, finger, ankle, elbow and shoulder. In operation, the particles are administered, surgically or through injection, into the synovial space to act as a bulking agent, promote lubricity and/or cushioning in the joint, and/or promote the remodeling, reconstitution or repair of the tissue, cartilage, ligaments and or bone within the joint.

Figure 16:
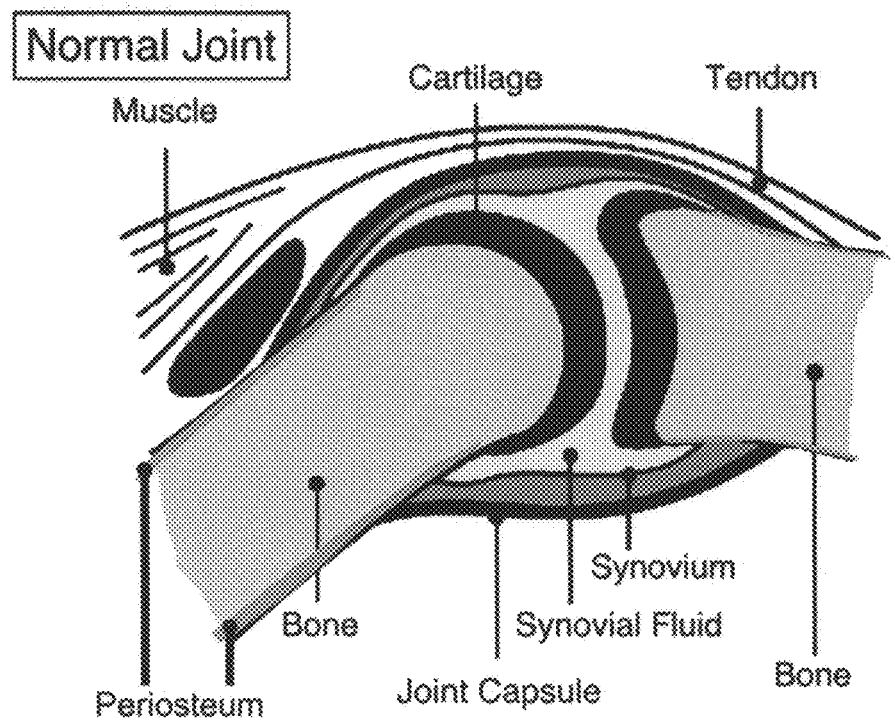
FIG. 16 depicts a joint without particles injected in the synovial space/synovial fluid in the top illustration and with particles in the synovial space/synovial fluid in the bottom illustration.
Figure 16:
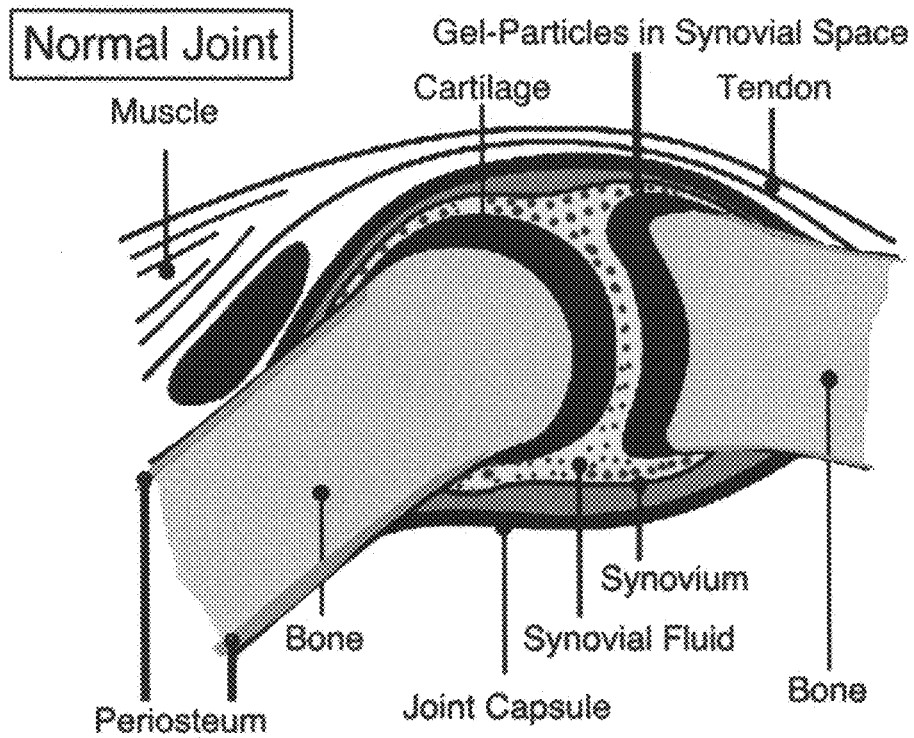
Figure 17:
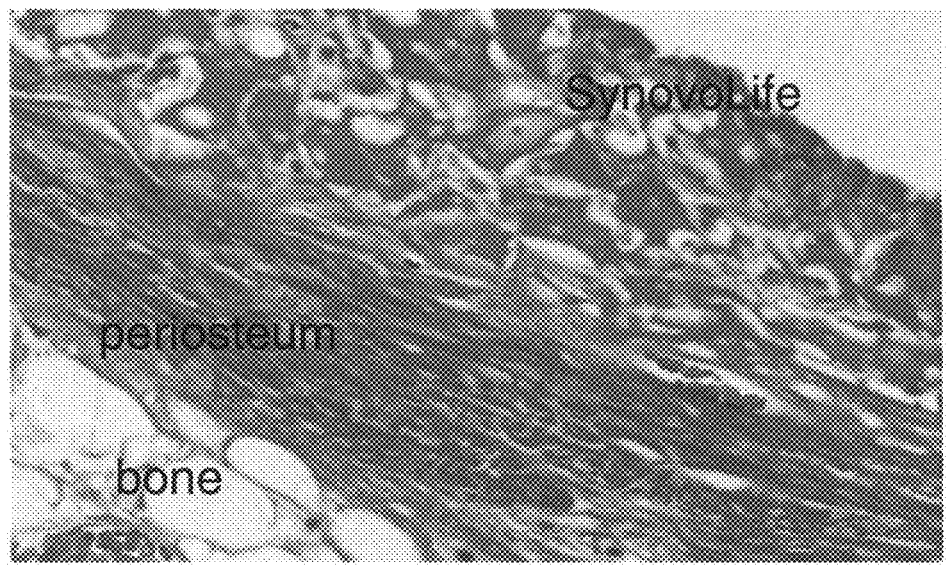
FIG. 17 depicts magnified histological views of SynovoLife™ particles attached to the periosteum in the top view and the synovium in the bottom view.
Figure 17:
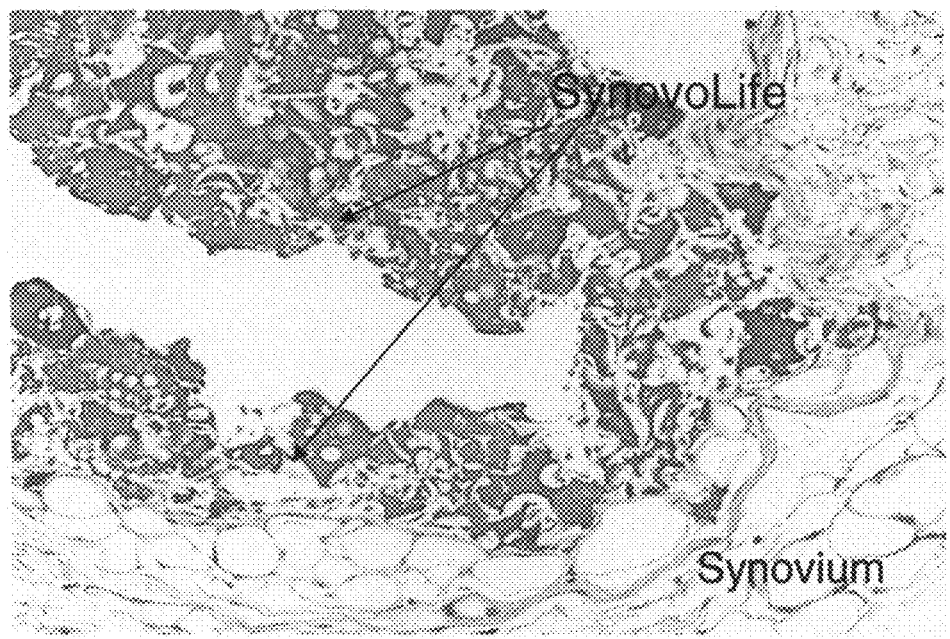
Figure 18:
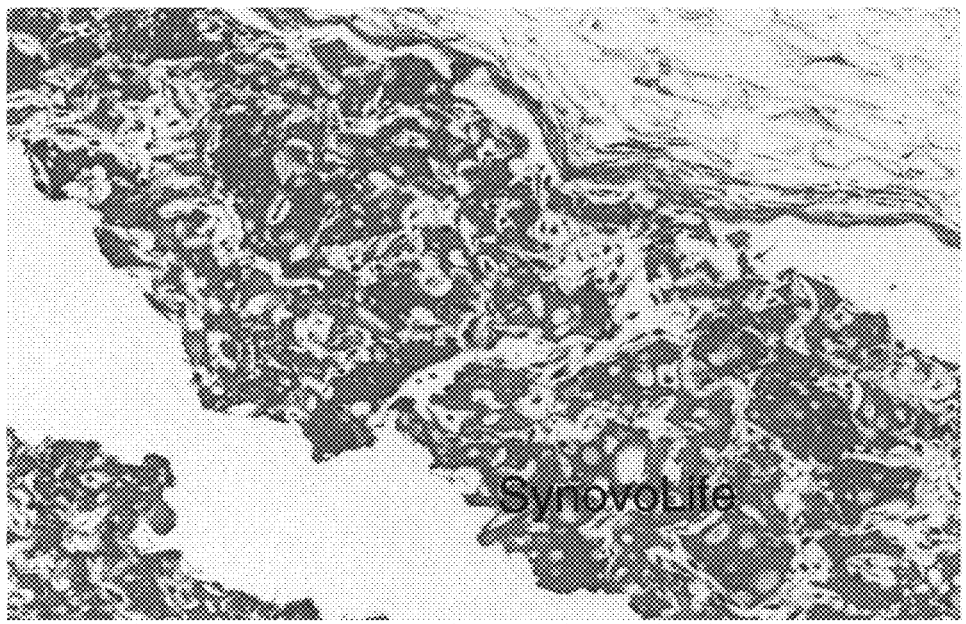
FIG. 18 depicts magnified histological views of SynovoLife™ particles attached to the synovium in the top view and the ligament in the bottom view.
Figure 18:
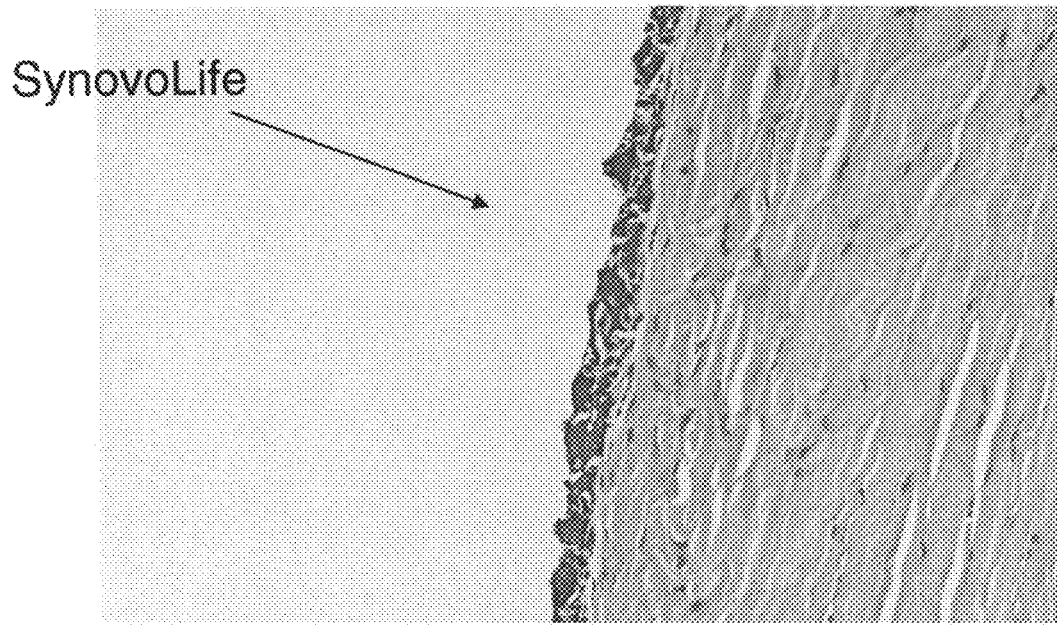
Figure 19:
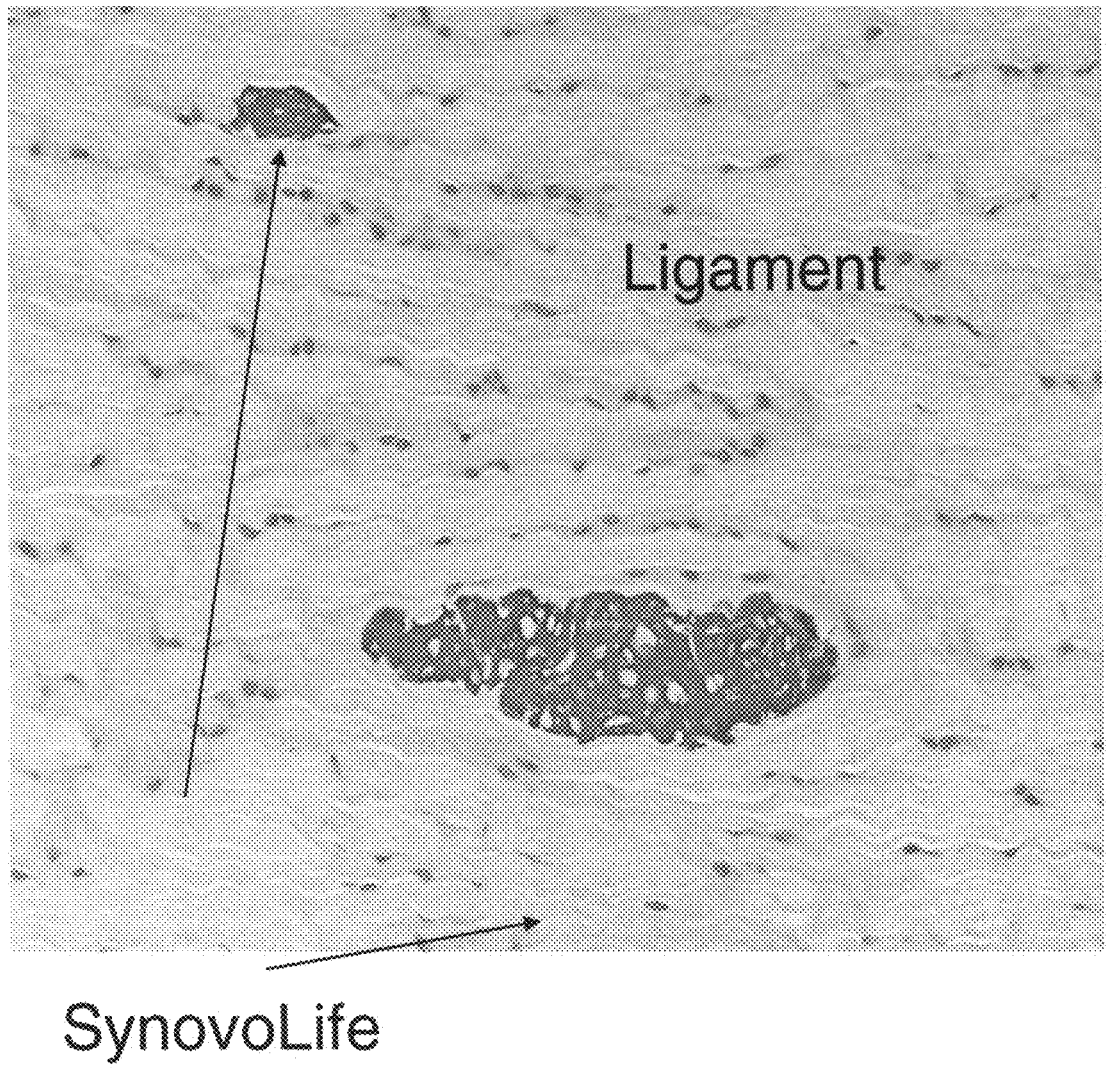
FIG. 19 depicts a magnified histological view of SynovoLife™ particles imbedded/injected in the ligament.

For example, a therapeutically effective amount of the protein-based particles of the present invention can be injected through the synovium and into the area that includes the synovial fluid of the knee joint, as depicted in the illustrations of knee joints with or without particles of FIG. 16. In all embodiments, the particles have been found to generally form a joint cushion buffering the adjacent bones/cartilage. FIGS. 17-19 depict histology of rabbit knee joints wherein particles of the present invention have been injected in the synovial area of the knee.

Figure 20:
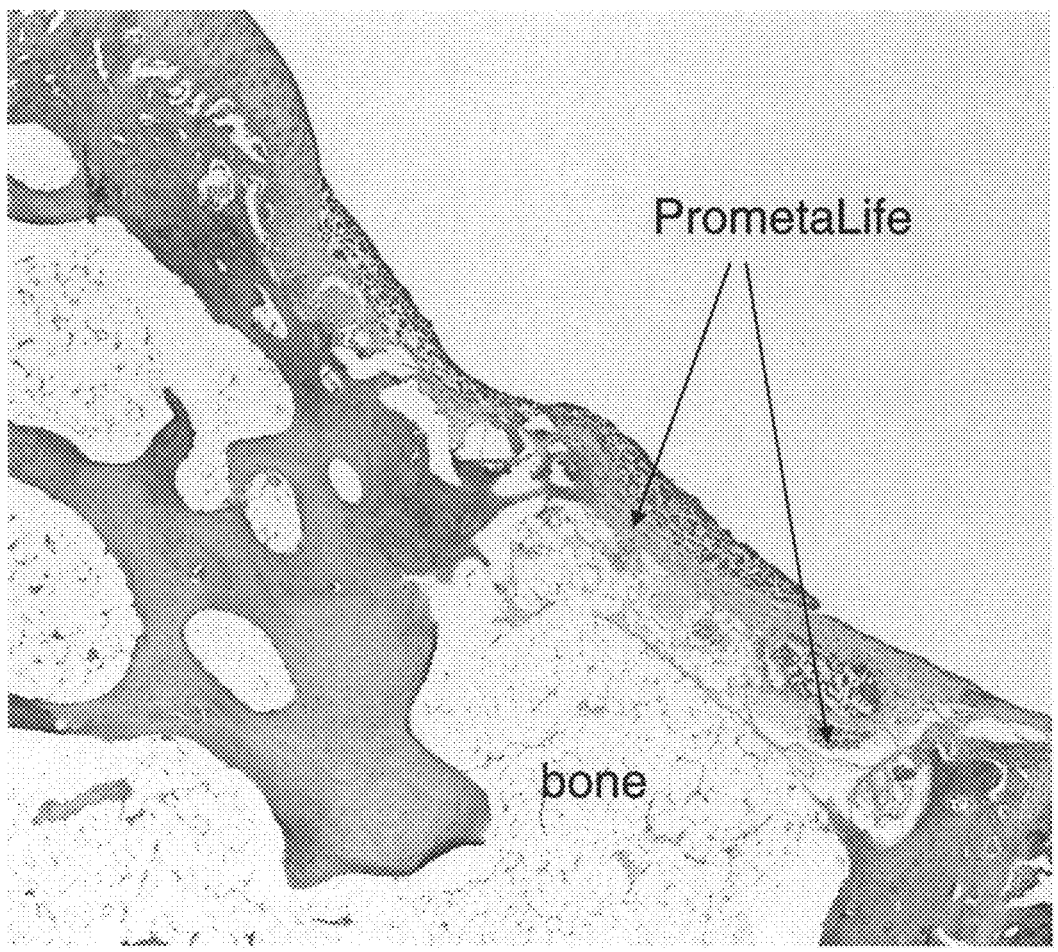
FIG. 20 depicts a magnified histological view of SynovoLife™ particles attached to and imbedded in the periosteum.
Figure 21:
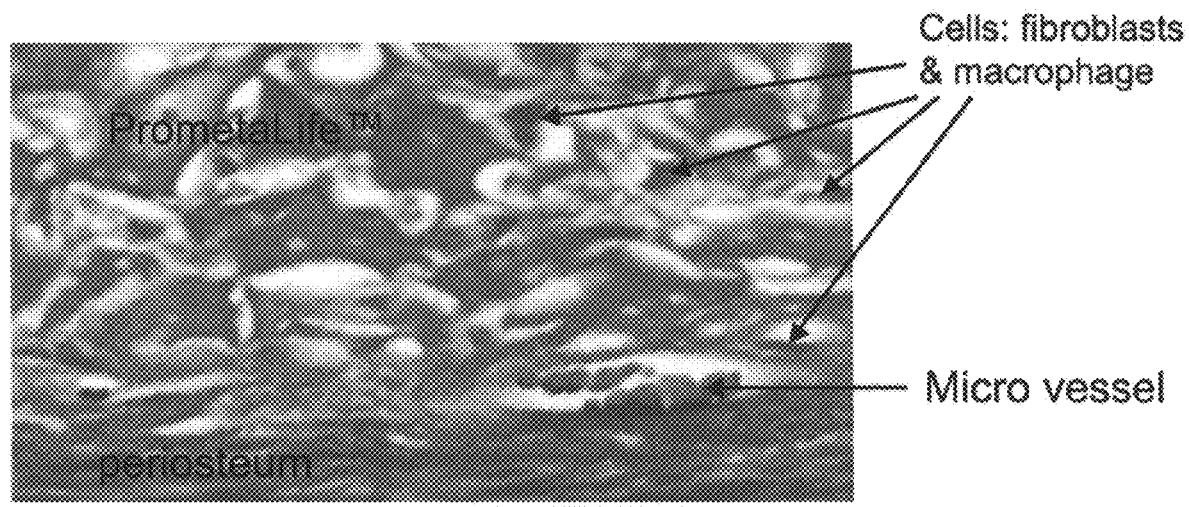
FIG. 21 depicts a magnified histological view of SynovoLife™ particles attached to the periosteum wherein connective tissue development is taking place within the particles and periosteum.

Additionally, it has been found in a number of embodiments of the present invention that the particles have an affinity to align with the periosteum, as depicted in FIGS. 20 and 21 and adjoin thereby providing a cushion between the bone and adjacent bone, cartilage, tissue and the like. FIGS. 20 and 21 depict histology samples taken from rabbits that depict the particles of the present invention aligning and attaching to the periosteum.

Generally, a therapeutically effective amount of the protein based material administered is determined by the amount that would bring the biological function back to a normal state or the amount that provides the desired biological effect. For example, in various embodiments of the present invention, the amounts administered to a joint, including, but not limited to the knee joint, will generally be approximately 0.05 cc to 10 cc; in other embodiments 0.2 cc to 7 cc; an in other embodiments 0.5 cc to 5 cc. In various embodiments of the present invention, the administration of a therapeutic amount of the protein-based material acts as a bulking agent, and/or promote lubricity and/or cushioning in the joint, and/or promotes the remodeling of the tissue, cartilage, periosteum, or other components in the joint.

One method of treating or enhancing the function of a joint or the method of administering a bulking material to enhance the function of a joint may be performed by the following steps:
  providing a syringe including a 12-32 gauge needle or other particle applicator filled with approximately 0.05 cc to 10 cc of a protein based material; and
  injecting in the joint a therapeutically effective amount of the protein based material.

This method wherein the protein-based material is injected in region containing the synovial fluid of the joint.

A case study evaluating the particles utilized as a bulking agent injected into rabbit knee joints was performed in June 2007. The processes and findings of the study are included below.

JOINT CASE STUDY (Synovial Fluid Replacement in Rabbits):

Purpose

The purpose of this study was to evaluate the ability of injectable biocoacervate protein-based particles (i.e. SynovaLife) to replace and/or augment the joint synovial fluid in a rabbit.

Experimental Design

The experimental design was as follows: 6 healthy adult New Zealand White rabbits were anesthetized per protocol.

The test sites were prepared as per the protocol and the biocoacervate protein based particles (i.e. SynovoLife, Pilot Testing of a Unique Compound, Lot #012430) was implanted bilaterally into the synovial joint The animals were maintained and observed for 1 or 4 weeks (Table A), euthanized and then the test implant sites were explanted at necropsy 1 or 4 weeks.

All tissues were fixed in 10% neutral buffered formalin. Hematoxylin and eosin (H&E) and Trichrome stained sections of the implant sites were prepared by the AppTec Histology Laboratory from all animals. A veterinary pathologist microscopically evaluated H&E stained tissue sections.

Test Article Identification:

| Animal Number | Duration | Injected Material |
|---|---|---|
| K6612 | 4 Week | SynovoLife, Pilot Testing of a Unique Compound, Lot # 012430 |
| K6613 | | |
| K6617 | | |
| K6614 | 1 Week | |
| K6615 | | |
| K6616 | | |

Results

Gross Pathology—There were no lesions found in any of the tissues during necropsy examination Microscopic Pathology—Histopathology of the Femurs and Tibia of Study 60735:
- Slide A=Left Leg Femur Left
- Slide B=Left leg Femur Right
- Slide C=Left leg Tibia
- Slide D=Right leg Femur Left
- Slide E=Right leg Femur Right
- Slide F=Right leg Tibia 1 Week Duration:

Animal K6614
- A—The articular cartilage contained several vertical clefts. The largest cleft extended to the subchondral bone. The cartilage matrix in the cartilage adjacent to the largest cleft had an area of chondromalacia (edema in the cartilage).

The chondrocytes in this area were normal.

There were several small irregularly shaped nests of vacuolated deeply basophilic material (test material) attached to the synovium. There was a minimal increase in mononuclear cells multifocally lining the synovium, especially where the test material was found.
- B—The surface of the articular cartilage contained several vertical and horizontal clefts. The cartilage and chondrocytes adjacent to these clefts were normal.

Attached to the synovium and floating within the joint capsule were small nest of the test material (mentioned in A) surrounded by minimal numbers of macrophages, mononuclear cells (reactive synovial cells), and a rare heterophil.
- C—There were two vertical clefts in the articular cartilage. The cartilage matrix and chondrocytes in the cartilage adjacent to this cleft were normal.

There were several small irregularly shaped nests of test material attached to and within the synovium. The test material was surrounded by a minimal number of mononuclear cells—likely reactive synovial cells.
- D—There was a focal area where the articular cartilage had a horizontal cleft that was almost completely transected from the cartilage. The chondrocytes within this cleft were normal but there was a minimal amount of edema within the matrix. There was a vertical cleft extending to the radiate zone (middle) of the articular cartilage.

The synovium was almost completely covered by a thin to thick layer of closely packed small nests of the vacuolated test material. Admixed with the test material were minimal numbers of macrophages, heterophils, mononuclear cells, and an occasional multinucleated giant cell.
- E—The articular cartilage contained one vertical cleft. The chondrocytes and cartilage in the adjacent cartilage were normal.

The synovium was almost completely covered by a thin to thick layer of closely packed small nests of the vacuolated test material. Admixed with the test material were minimal numbers of macrophages, heterophils, mononuclear cells, and an occasional multinucleated giant cell There were a few small nests of the test material also focally on the surface of the periosteum and free floating in the joint space. There were minimal numbers of the same inflammatory cells accompanying the test material.
- F—There were two small foci of the test material on the surface of the articular cartilage, adjacent to the eructate ligament attachment on the tibia, and focally on the synovium of the eructate ligament. There was a focal area where the articular cartilage was fragmented with a vertical cleft. The chondrocytes and matrix within this area was normal.

There were two small foci of the test material multifocally on the surface of the synovium.

Animal K6615
- A—There were several vertical and horizontal clefts in the articular cartilage The chondrocytes and matrix of the cartilage adjacent to these clefts were normal.

The synovium and eructate ligament were multifocally covered by a thin to thick layer of small closely packed nests of the test material admixed with minimal numbers of macrophages and mononuclear cells (likely reactive synovial cells).
- B—There was a large horizontal tear in the articular cartilage, which is from histology processing of the tissue. Also, the ligament on the surface of the femur was focally fragmented and there were several small clusters of chondrocytes in the fibrocartilage of the ligament (reactive chondrocytes).

The synovium and periosteum was multifocally covered by a thin to thick layer of small closely packed nests of the test material admixed with minimal numbers of macrophages, mononuclear cells, and an occasional heterophil and multinucleated giant cells
- C—There were several areas where the cartilage was torn, secondary to histology processing of the tissue.

There were small loosely packed nests of the test material focally on the surface of the synovium. The test material was surrounded by minimal numbers of macrophages.
- D—There were three vertical and one horizontal tear in the cartilage, secondary to histology processes.

The synovium was multifocally covered by a thick layer of small, closely packed nests of the test material, admixed with minimal numbers of macrophages and an occasional mononuclear cell, heterophil and multinucleated giant cell. There was a small focus of the test material on the periosteum.
- E—There were two vertical tears in the articular cartilage. One of the tears, in the attachment of the cartilage to the adjacent ligament, had a large tear and several small nest of test material.

The thought is that the tears in the cartilage are from histology processing and the test material present in one of the tears was dragged there, also secondary to histology processing.

The synovium was multifocally covered by a thick layer of small, closely packed nests of the test material, admixed with minimal numbers of macrophages and an occasional mononuclear cell, heterophil and multinucleated giant cell.

F—Several small nests of the test material multifocally covered the synovium and periosteum admixed with scant macrophages and mononuclear cells. There was a small focus of the test material also within the joint, on the surface of the tibial plateau.

Animal K6616

A—There was one vertical tear in the articular cartilage, secondary to histology processing of the tissues.

The synovium was multifocally covered by a thick layer of small, closely packed nests of the test material, admixed with minimal numbers of macrophages and an occasional mononuclear cell, heterophil and multinucleated giant cell.

B—There were two vertical tears in the articular cartilage, secondary to histology processing of the tissues.

Several small nests of the test material multifocally covered the synovium and periosteum admixed with scant macrophages and mononuclear cells C—There were no changes in the articular cartilage.

The synovium was multifocally covered by a thick layer of small, closely packed nests of the test material, admixed with small numbers of macrophages and an occasional mononuclear cell, heterophil and multinucleated giant cell.

D—There were two small superficial tears in the articular cartilage, secondary to the histology processing of the tissue.

Several small nests of the test material multifocally covered the synovium and periosteum admixed with scant macrophages and mononuclear cells.

E—There were no changes in the articular cartilage.

The synovium was multifocally covered by a thick layer of small, closely packed nests of the test material, admixed with small numbers of macrophages and an occasional mononuclear cell, heterophil and multinucleated giant cell.

F—There was one vertical tear in the articular cartilage, secondary to the histology processing of the tissue.

Several small nests of the test material multifocally covered the synovium and periosteum admixed with scant macrophages and mononuclear cells.

4 Week Duration:

Animal K6612

A—There were several vertical tears in the articular cartilage, secondary to the histology processing of the tissue. The synovium was multifocally covered by a thick layer of small, closely packed nests of the test material, admixed with small numbers of macrophages and an occasional mononuclear cell, heterophil and multinucleated giant cell.

B—There was one vertical tear in the articular cartilage, secondary to the histology processing of the tissue.

The synovium and periosteum was multifocally covered by a thin layer of small, closely packed nests of the test material, admixed with small numbers of macrophages and an occasional mononuclear cell, heterophil and multinucleated giant cell.

C—There were several vertical tears in the articular cartilage, secondary to the histology processing of the tissue. The synovium and periosteum was multifocally covered by a thin layer of small, closely packed nests of the test material, admixed with small numbers of macrophages and an occasional mononuclear cell, heterophil and multinucleated giant cell.

D—There were several vertical and superficial horizontal tears in the articular cartilage, secondary to the histology processing of the tissue The synovium and periosteum was multifocally covered by a thin to layer of small, closely packed nests of the test material, admixed with small numbers of macrophages and an occasional mononuclear cell, heterophil and multinucleated giant cell.

E.—Them were no changes in the articular cartilage.

The synovium was multifocally covered by a thin layer of small, closely packed nests of the test material, admixed with small numbers of macrophages and an occasional mononuclear cell, heterophil and multinucleated giant cell. There were a few small nest of test material on the surface of the ligament adjacent to the femur.

F—There were several vertical tears in the articular cartilage, secondary to the histology processing of the tissue.

The synovium was multifocally covered by a thin layer of small, closely packed nests of the test material, admixed with small numbers of macrophages and an occasional mononuclear cell, heterophil and multinucleated giant cell.

Animal K6613

A—There were several vertical tears in the articular cartilage, secondary to the histology processing of the tissue. The synovium was multifocally covered by a thick layer of small, closely packed nests of the test material, admixed with small numbers of macrophages and an occasional mononuclear cell, heterophil and multinucleated giant cell.

B—There were several vertical tears in the articular cartilage, secondary to the histology processing of the tissue.

The synovium was multifocally covered by a thick layer of small, closely packed nests of the test material, admixed with small numbers of macrophages and an occasional mononuclear cell, heterophil and multinucleated giant cell.

C—There were several vertical tears in the articular cartilage, secondary to the histology processing of the tissue. The synovium was multifocally covered by a thin layer of small, closely packed nests of the test material, admixed with small numbers of macrophages and mononuclear cells, and an occasional heterophil and multinucleated giant cell.

D—Them were several vertical tears in the articular cartilage, secondary to the histology processing of the tissue.

The synovium and periosteum was focally to multifocally covered by a thick layer of small, closely packed nests of the test material, admixed with small numbers of macrophages, lymphocytes, and an occasional mononuclear cell, heterophil and multinucleated giant cell. There were a few small nest of test material on the surface of the ligament adjacent to the femur, and a small focus of several closely packed nests of the test material within the connective tissue of the periosteum.

E—A small piece of the synovium containing small numbers of macrophages and mononuclear cells was attached to the surface of the articular cartilage. The articular cartilage was fragmented in several areas from histology processing of the tissue.

Focally the periosteum and ligament adjacent to the femur was covered by a small thin layer of test material admixed with scant macrophages.

F—There were several vertical tears in the articular cartilage, secondary to the histology processing of the tissue.

The synovium, periosteum and ligament adjacent to the femur was focally covered by a thin layer of small, closely packed nests of the test material, admixed with small numbers of macrophages and mononuclear cells, and an occasional heterophil and multinucleated giant cell.

Animal K6617
- A—The articular cartilage was focally fragmented from histology processing of the tissue. A few small nest of the test material accompanied by small numbers of macrophages, mononuclear cells, and an occasional multinucleated giant cells, multifocally covered the surface of the ligament adjacent to the femur and focally covered the periosteum. There were also three small foci of the test material, without inflammation, within the ligament.
- B—The articular cartilage was focally fragmented from histology processing of the tissue. The synovium and periosteum was focally to multifocally covered by a thick layer of small, closely packed nests of the test material, admixed with small numbers of macrophages, lymphocytes, and an occasional heterophil and multinucleated giant cell.
- C—There were several vertical tears in the articular cartilage, secondary to the histology processing of the tissue. The synovium was focally to multifocally covered by a thick layer of small, closely packed nests of the test material, admixed with small numbers of macrophages, lymphocytes, and an occasional mononuclear cell, heterophil and multinucleated giant cell. There was a large focus of the test material in the joint space, and several small focus of test material, without inflammation in the cruciate ligament attached to the tibia.
- D—The articular cartilage was multifocally fragmented from histology processing of the tissue.

The synovium and periosteum was focally to multifocally covered by a thick layer of small, closely packed nests of the test material, admixed with small numbers of macrophages, lymphocytes, and an occasional mononuclear cell, heterophil and multinucleated giant cell.
- E—The articular cartilage was multifocally fragmented from histology processing of the tissue.

The synovium and periosteum was focally to multifocally covered by a thin to thick layer of small, closely packed nests of the test material, admixed with small numbers of macrophages, lymphocytes, and an occasional mononuclear cell, heterophil and multinucleated giant cell.
- F—There were no changes in the articular cartilage.

Focally the synovium was thickened by small numbers of macrophages, multinucleated giant cells, mononuclear cells, and fewer heterophils and lymphocytes. The giant cells were surrounding small nests of test material.

Trichrome Slides:

The Trichrome slides contained the same changes mentioned above in the H & E slides. The test material was pale blue in the Trichrome slides.

Discussion:

1 Week Duration:

A few of the articular cartilages of the femur did not have any microscopic changes, but most of the articular cartilage from the femur and tibia had one or more vertical or horizontal tears/clefts that are thought to be from histology processing of the tissues. The cartilage and chondrocytes adjacent to the tears/clefts were normal, except for K6614, slide A and D. There was a focal area of minimal chondromalacia (cartilage edema) in the cartilage adjacent to one of the tears/clefts. This edema could be a true lesion, however, the chondrocytes within these areas were normal. The thought is that the edema is an artifact caused by pulling of the tissue when the adjacent tear/cleft occurred in the tissue.

The ligament on the surface of the K6615 (slide B) femur was focally fragmented and there were several small clusters of chondrocytes in the fibrocartilage of the ligament (reactive chondrocytes). The fragmentation of the ligament is likely from histology processing of the tissues, and reactive chondrocytes can normally be found where ligaments attached to cartilage.

Small foci to thin to thick layers of the test article, SynovoLife, Pilot Testing of a Unique Compound. Lot #012430, were found attached to the synovium and periosteum, on the surface of the articular cartilage, adjacent to the cruciate ligament of the tibia, and free floating within the joint capsule. The free floating test material within the joint capsule in some sections could be a result of the test material being detached from its attachment area during histology processing of the tissues. Admixed with the test material, in all sites, were scant to small numbers of macrophages, mononuclear cells (reactive synovial cells), and/or fewer heterophils and multinucleated giant cells.

4 Week Duration:

All of the articular cartilages from the femur and tibia had one or more vertical or horizontal tears/clefts that are thought to be from histology processing of the tissues. The cartilage and chondrocytes adjacent to the tears/clefts were normal.

A small piece of the synovium in the K6613 (slide B) containing small numbers of macrophages and mononuclear cells was attached to the surface of the articular cartilage. This is likely from an earlier injury or irritation of the articular cartilage in this area. The synovium (probably from the ligament attached in this area) would incite an inflammatory response to the injury/irritation of the articular cartilage, and could end up adhered to the site during the healing of the injury/irritation. This site is not thought to be secondary to injection of the test article into the joint, but cannot be completely ruled out.

Small foci to thin to thick layers of the test article, SynovoLife, Pilot Testing of a Unique Compound, Lot #012430 were found attached to the synovium and periosteum, on the surface of and in the ligament adjacent to the femur, free floating within the joint capsule, and within the cruciate ligament of the tibia and periosteum. The free floating test material within the joint capsule in one section could be a result of the test material being detached from its attachment area during histology processing of the tissues. Admixed with the test material, in all sites, were scant to small numbers of macrophages, mononuclear cells (reactive synovial cells), and/or fewer lymphocytes, heterophils and multinucleated giant cells.

Admixed with the test material on the K6613 slide A, two multinucleated giant cells were surrounding a fragment of clear, anuclear, and refractive material—unknown material. This material is thought to be from the surgical preparation of the animal and possibly dragged into the joint with injection of the test material.

Conclusion

Under the conditions of this Pilot Testing of a Unique Compound Designed to Provide Tissue Support and Healing: Synovial Fluid Replacement in Rabbits study, the Test Article, SynovoLife. Pilot Testing of a Unique Compound. Lot #012430, did not cause gross or microscopic changes in the articular cartilage of the femur or tibia when injected into the stifle joint of rabbits. Test material was found in almost all of the tissue sections submitted for microscopic evaluation, and was found attached to the synovium and periosteum, on the surface of and in the ligament adjacent to the femur, free floating within the joint capsule, and/or within the cruciate ligament of the tibia and periosteum. Accompanying the test material were small numbers of chronic inflammation and reactive synovial cells.

The small piece of synovium attached to the surface of the articular cartilage in the K6613 (slide E) is likely not from injection of the test article into the stifle joint, but cannot be completely ruled out.

EXAMPLES

The protein-based materials and particles of the present invention will now be further described with reference to the following non limiting examples and the following materials and methods that were employed.

Example I

Spread Matrix Particles

Bovine fibrous collagen (1.715 g) was mixed with elastin (0.457 g) and heparin (0.114 g) in a two-syringe mixing system with the addition of 5 ml of distilled water and 3 ml of phosphate buffered saline (pH 7.4). When the mixture appeared uniform, the resulting material was dehydrated at 30° C. until 60% of the added water was removed. This paste (B-stage) was stored at 42° F. overnight. The B-stage was made into smaller pieces suitable for use in a single ball grinding device held at liquid nitrogen temperature. This grinding resulted in a particulate material.

Example II

Bovine fibrous collagen (1.715 g) was mixed with elastin (0.457 g) and heparin (0.114 g) in a two-syringe mixing system with the addition of 5 ml of distilled water and 3 ml of phosphate buffered saline (pH 7.4). When the mixture appeared uniform, it was spread on a flat surface and dehydrated overnight at 40° C. to yield a solid. This solid was broken into pieces and ground at liquid nitrogen temperature to yield particles.

Example III

Cross-Linking of Collagen/Elastin/Heparin Cohesive Body

The glutaraldehyde treatment of a cohesive body including collagen, elastin and heparin at a 7/2/1 ratio is as follows: add 0.2 ml of 50% aqueous glutaraldehyde to 100 ml of distilled water. To the stirred solution (magnet stir bar) add fully-hydrated cohesive body pieces (no more than 14 grams has been used at this point) and stir slowly (just enough to move the cohesive body pieces) for 2 hours at ambient temperature. The pieces are rinsed three times with fresh distilled water. Next 100 ml of water is added to the beaker with cohesive body pieces and approximately 0.13 g of glycine and 0.13 g of glutamine is added to the beaker and stirred slowly for 30 minutes. Next, the cohesive body pieces are rinsed 3 times with fresh water. The crosslinked cohesive body pieces are then removed from the beaker and placed on a glass plate or weighing dish and dried at 50° C. for approximately 48 hours.

Example IV

Particle Processing

One particle formation process is as follows: The cross-linked cohesive body of Example III is ground in a reciprocating grinding system until all ground material passes through a 150 micron sieve. The final ground particles are added to a beaker containing approximately 30-50 mls of PBS stirred sufficiently to fully disperse the particles—no clumping is allowed. The dispersed particles are allowed to settle overnight in the refrigerator. The supernatant is decanted or pipetted off and the suspended particles are "dewatered" by any of several methods (wicking, centrifugation, compression between absorbent materials). The dewatered particles are next added to at least a 6 ml syringe at the plunger end and then injected into 1 ml syringes through a metal syringe connector. The final 1 ml syringe is then sterilized with approximately 60 Krads of gamma radiation and stored in the refrigerator ready for use. The particles are suitable for injection through a 30 gauge or larger bore needle.

Example V

Preparation of Biocoacervate

Soluble bovine collagen (Kensey-Nash Corporation) (1.5 gs) was dissolved in distilled water (100 mls) at 42° C. To this solution was added elastin (bovine neck ligament, 0.40 g) and sodium heparinate (0.20 g) dissolved in distilled water (40 mls) at room temperature. The elastin/heparin solution was added quickly to the collagen solution with minimal stirring thereby immediately producing an amorphous coacervate precipitate. The resulting cloudy mixture was let standing at room temperature for 1-2 hrs and then refrigerated. The rubbery precipitate on the bottom of the reaction flask was rinsed three times with fresh distilled water and removed and patted dry with filter paper to yield 6.48 gs of crude coacervate (MasterGel™) which was then melted at 55° C. and gently mixed to yield a uniform, rubbery, water-insoluble final product after cooling to room temperature. The supernatant of the reaction mixture was later dried down to a solid which weighed 0.417 g and was water soluble. The uniform MasterGel™ material was used to fabricate both injectable compositions for tissue augmentation and biocompatible structures for grafts.

Example VI

Biocoacervate Materials Including Additives and pH Solutions

MasterGel™ material was prepared as described in Example V. Nine 1 g samples of MasterGel™ were cut and placed in a glass scintillation vial. The vial was then placed in a water bath at 60° C. and melted. Once melted either an additive or pH solution was added to each sample of MasterGel™. The following additives were administered: polyethylene glycol, chondroitin sulfate, hydroxyapatite, glycerol, hyaluronic acid and a solution of NaOH. Each of the above mentioned additives were administered at an amount of 3.3 mg separately to four melted samples of MasterGel™ with a few drops of water to maintain MasterGel™ viscosity during mixing. Each of the above mentioned additives were also administered at an amount of 10 mg to another four melted samples of MasterGel™ with a few drops of water to maintain MasterGel™ viscosity. Finally, NaOH was added to the final melted MasterGel™ sample until the MasterGel™ tested neutral with pH indicator paper. The uniform MasterGel™ material including additives or pH solution were crosslinked with 0.1% gluteraldehyde for 2 hours and used to fabricate injectable compositions for tissue augmentation.

Example VII

Preparation of Ground Particles

A sample of MasterGel™ was cut into small pieces and treated with a glutaraldehyde (0.1-1.0%) aqueous solution for up to 2 hours. The resulting biocoacervate (MasterGel™) material was then dried at 45° C. for 24 hours and ground to a fine powder and sieved through a 150μ screen. This powder was then suspended in phosphate-buffered saline to give a thick, flowable gel-like material which could be injected through a fine needle (23-30 ga.). This formulation is useful for augmentation of lips, organs or other parts of the body after injection.

Example VIII

Preparation of Homogenized Particles

Samples of MasterGel™ as described in Example VI were cut into small pieces and treated with a glutaraldehyde (0.1%) aqueous solution for 2 hours, was rinsed three times with distilled water, treated with a glycine/glutamine solution for 30 minutes and rinsed again twice with distilled water. It is noted that other embodiments have been treated with 0.2, 0.5 and 1% glutaraldehyde solutions to crosslink the MasterGel™. The material was next placed in PBS overnight. The crosslinked coacervate (MasterGel™) material was removed from PBS solution and homogenized with a handheld homogenizing polytron to form a wet viscous fine particle mass. The viscous particle mass was then loaded into syringes, which could be injected through a fine needle (23-30 ga.). This formulation is useful for augmentation of lips, organs or other parts of the body after injection.

Example IX

In Situ Curing of Biocoacervate Adhesive/Filler

Purpose: to optimize a process for in situ curing of Biocoacervate adhesive/filler using molten MasterGel™ or with particles augmentation, and gluteraldehyde crosslinker.
Methods:
MasterGel™ was melted in a hybridization oven set to 52 C prior to use. Gluteraldehyde, diluted to a 1% solution in sterile water for irrigation, was also pre-heated in the oven. Small 1 ml glass vials were pre-heated in the oven for pre-mixing of solutions. Pre-mixing was accomplished by first pipetting molten MasterGel™ into the glass vial. When used in the formulation, particles of the present invention were then added to the vial directly from syringes and mixed with a pipette tip. Finally, 1% gluteraldehyde solution was added to the vial and the entire solution quickly and thoroughly mixed. Fully mixed solution was then quickly added to wells of a 12-well plate before the solution could harden. Various formulations tested are listed below:

| Sample # | MasterGel ™ (ul) | CosmetaLife ™ (ul) | 1% GA |
|---|---|---|---|
| 1 | 400 | | 100 |
| 2 | 750 | | |
| 3 | 600 | | 150 |
| 4 | 675 | | 75 |
| 5 | 500 | 100 | 150 |
| 6 | 450 | | 300 |
| 7 | 500 | | 250 |
| 8 | 250 | 250 | 150 |
| 9 | 400 | 200 | 150 |
| 10 | 400 | 200 | 100 |

Results:
Sample 1 - Good consistency; sets quickly at room temp (~10 min); sample to thin for compression testing (~1.5 mm thick)
Sample 2 - Better thickness for testing (3-4 mm thick); gel didn't set after approx 2 hr incub at room temp
Sample 3 - Sets quickly (~10 min); very soft
Sample 4 - Slow to set (>2 hrs)
Sample 5 - Sets quickly (5-10 min); denser than #3, but still fairly soft
Sample 6 - MasterGel ™ solidifies immediately upon addition of GA and can't pipette to well
Sample 7 - As #6
Sample 8 - Sets quickly (~5 min); somewhat difficult to pre-mix and pipette to well
Sample 9 - Sets quickly (~5 min); easier to pipette than #8; good consistency (dense but soft)
Sample 10 - Sets more slowly than #9 (~10 min); easier to mix and pipette than #9; consistency is softer and more delicate than #9

Discussion: There seems to be some balance between ease of handling during pre-mixing (ie. having enough time to mix optimally and still maintain a liquid state for pipetting/filling a syringe) and setting up of the solid state in a timely manner. Samples #9 and #10 seem close to an ideal balance of both properties, although there is still room for experimentation from those baselines. In various embodiments at least 125 ul of 1% GA may be used to get adequate integrity of the solid, although the MasterGel™ to particles ratio affects this, as well.

Example X

Fibroblast Spectrum

Figure 22:
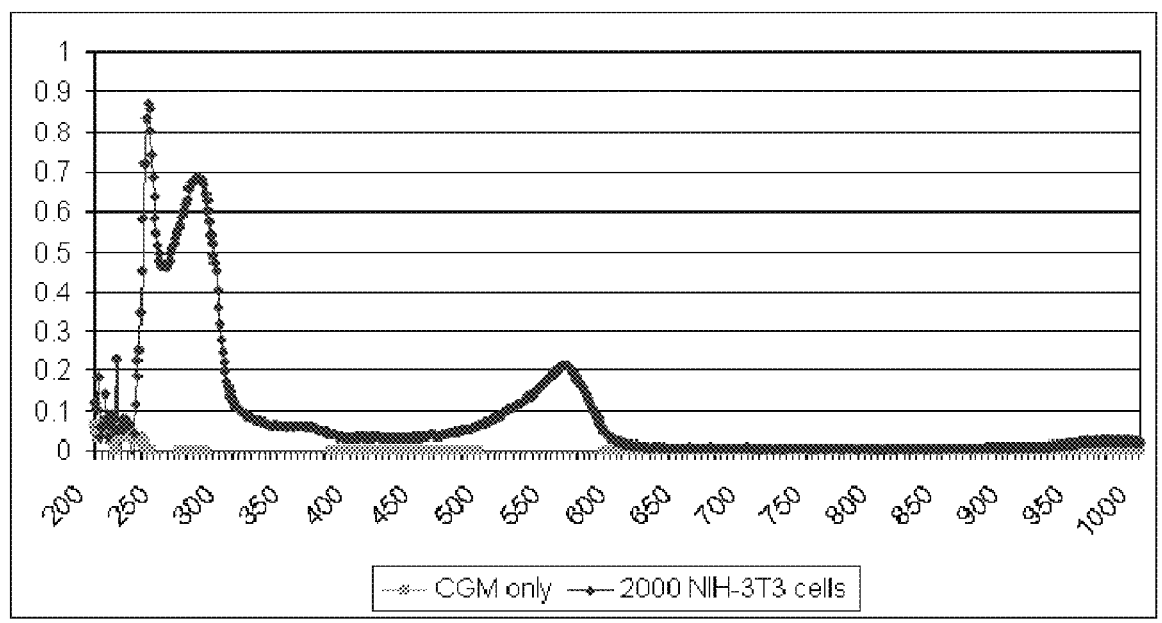
FIG. 22 depicts fibroblast spectrum experiments.
Figure 23:
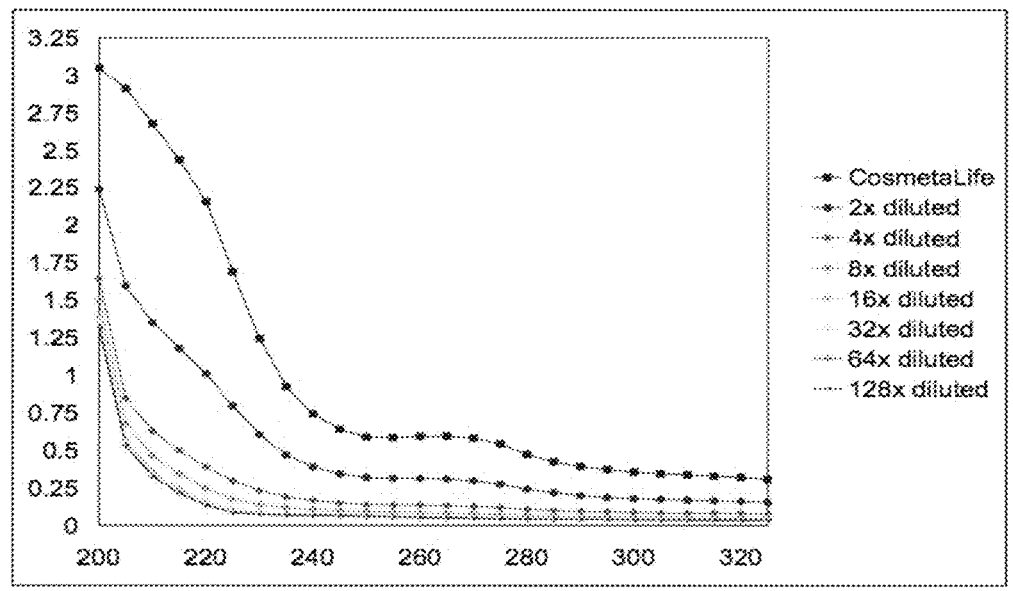
FIG. 23 depicts the absorption of and embodiment of the particulate material of the present invention in various diluted states with PBS (e.g. 2×, 4×, 6× . . . ) and includes data up to wavelengths of 320 nm.
Figure 24:
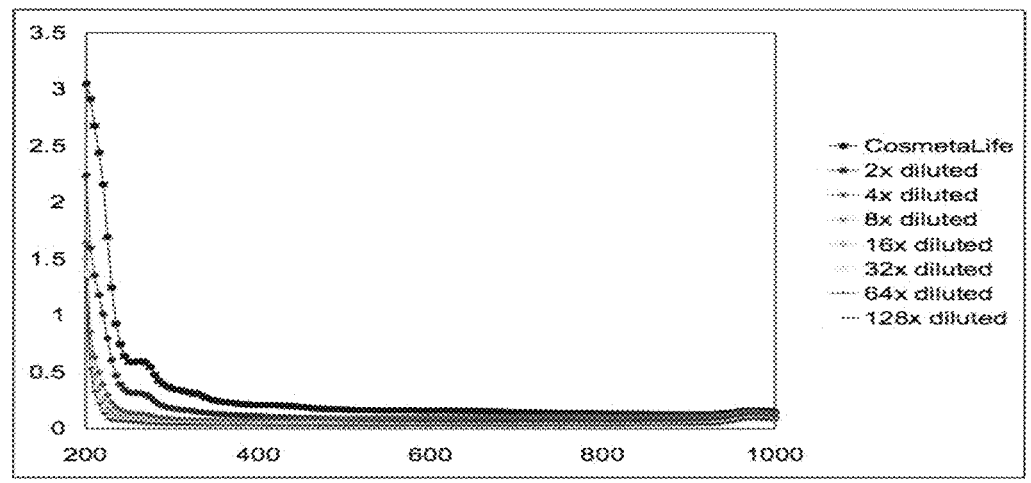
FIG. 24 depicts the absorption of and embodiment of the particulate material of the present invention in various diluted states with PBS (e.g. 2×, 4×, 6× . . . ) and includes data up to wavelengths of 1000 nm.

Fibroblast spectrum experiments are illustrated in FIG. 22. Cultured NIH-3T3 cells were replated to a 96-well plate at various concentrations and compared to the used complete growth media (CGM) alone (DMEM/antibiotics/serum) as the background. The best concentration was 2000 cells/well and plotted against background as shown in FIG. 22. The cells are suspended NIH-3T3 fibroblasts at room temperature, about 30 minutes after replating, so they are truly suspended or at best loosely adherent. The wavelengths in the graph of FIG. 22 are in full scale (200-1000 nm) format and a close-up of the interesting area (200-325 nm). The x-axis is wavelength and the y-axis is absorbance. As displayed in the chart of FIG. 22, at various wavelengths fibroblasts are shown to absorb radiation especially when the wavelengths are approximately 250-325 nm and from 500-600 nm. The charts of FIGS. 23 and 24 illustrate the absorption of the particulate material of the present invention (e.g. CosmetaLife product) in various diluted states with PBS (e.g. 2×, 4×, 6× . . . ). The first chart includes data up to wavelengths of 320 nm and the second chart is the full spectrum illustrating wavelengths up to 1000 nm. As illustrated, the particulate material consistently absorbs radiation of wavelengths up to 220 nm, thereby allowing absorption of radiation to heat or activate the material and/or surrounding solution (including biochemicals and chemicals) and further promote activation of fibroblasts on the material. It is noted that chemical enhancers may be used in combination with radiation or by themselves to promote the activity of fibroblasts on the material.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations, which fall within the spirit and broad scope of the invention.

The invention claimed is:

1. A method of treating or enhancing the function of a joint comprising:
administering a plurality of particles to the synovial space or the area proximal to the periosteum in the joint of a patient, said particles comprising one or more biocoacervate material(s) precipitated from a solution comprising effective proportions of two or more soluble biocompatible proteins, one or more glycosaminoglycans and one or more biocompatible solvents,
wherein the biocoacervate material(s) are shape-holding solid precipitate,
wherein all or a portion of the particles are crosslinked with one or more crosslinking agents,
wherein the two or more soluble biocompatible proteins comprise Type I collagen and elastin,
wherein the one or more glycosaminoglycans comprise heparin,
wherein the biocoacervate material(s) comprise a ratio of about 2 parts of elastin to about 1 part of the one or more glycosaminoglycans to at least one of: about 7 parts of Type I collagen, and about 7.5 parts of Type I collagen, and
wherein the particles have a size of approximately 500 nm to 1000 μm.

2. The method of claim 1 wherein the two or more soluble biocompatible proteins further comprise at least one of the group consisting of albumin, keratin, laminin, fibronectin, silk, silk fibroin, actin, myosin, fibrinogen, thrombin, aprotinin, antithrombin III, elastinlike blocks, silklike blocks, collagenlike blocks, lamininlike blocks, fibronectinlike blocks and silklike, elastinlike blocks, collagen-heparin, collagen-elastin-heparin and collagen-chondroitin.

3. The method of claim 1 wherein the one or more biocompatible solvent(s) is selected from the group consisting of water, dimethyl sulfoxide (DMSO), biocompatible alcohols, biocompatible acids, oils and biocompatible glycols.

4. The method of claim 1 wherein the particles further includes one or more pharmacologically active agents selected from the group consisting of analgesics, anesthetics, antipsychotic agents, angiogenic growth factors, bone mending biochemicals, steroids, antisteroids, corticosteroids, antiglaucoma agents, antialcohol agents, anti-coagulants agents, genetic material, antithrombolytic agents, anticancer agents, anti-Parkinson agents, antiepileptic agents, permeation enhancers, anti-inflammatory agents, anticonception agents, enzymes agents, cells, growth factors, antiviral agents, antibacterial agents, antifungal agents, hypoglycemic agents, antihistamine agents, chemoattractants, neutraceuticals, antiobesity agents, smoking cessation agents, obstetric agents and antiasmatic agents.

5. The method of claim 4 wherein the pharmacologically active agent is selected from anesthetics, analgesics, anticoagulant agents or neurotoxins.

6. The method of claim 1 wherein the particles further include one or more biocompatible additives.

7. The method of claim 6 wherein the one or more biocompatible additives are selected from the group consisting of epoxies, polyesters, acrylics, nylons, silicones, polyanhydride, polyurethane, polycarbonate, poly(tetrafluoroethylene), polycaprolactone, polyethylene oxide, polyethylene glycol, poly(vinyl chloride), polylactic acid, polyglycolic acid, polypropylene oxide, poly(akylene)glycol, polyoxyethylene, sebacic acid, polyvinyl alcohol, 2-hydroxyethyl methacrylate, polymethyl methacrylate, 1,3-bis(carboxyphenoxy)propane, lipids, phosphatidylcholine, triglycerides, humectants, polyhydroxybutyrate, polyhydroxyvalerate, poly(ethylene oxide), poly ortho esters, poly(amino acids), polycyanoacrylates, polyphophazenes, polysulfone, polyamine, poly(amido amines), fibrin, graphite, flexible fluoropolymer, isobutyl-based, isopropyl styrene, vinyl pyrrolidone, cellulose acetate dibutyrate, silicone rubber, and copolymers or combinations of these.

8. The method of claim 1 wherein the one or more crosslinking agents are-selected from the group consisting of glutaraldehyde, formaldehyde, p-Azidobenzolyl Hydrazide, N-5-Azido 2-nitrobenzoyloxysuccinimide, 1,4-butandiol diglycidylether, N-Succinimidyl 6-[4'azido-2'nitro-phenylamino]hexanoate, tannic acid and 4-[p-Azidosalicylamido]butylamine.

9. The method of claim 1 wherein the particles have an affinity to align and adjoin with the periosteum.

10. The method of claim 1 wherein the one or more glycosaminoglycan(s) further comprise at least one of the group consisting of heparan sulfate, keratin sulfate dermatin, dermatin sulfate, heparin-hyaluronic acid, chondroitin, chondroitin sulfate, chondroitin 6-sulfate, chondroitin 4-sulfate, chitin, chitosan, acetyl-glucosamine, hyaluronic acid aggrecan, decorin, biglycan, fibromodulin, lumican and complexes thereof.

11. The method of claim 10 wherein the one or more biocompatible solvent(s) is water.

12. The method of claim 1 wherein a therapeutically effective amount of about 0.05 cc to about 10 cc of the particles is administered to the synovial space or the area proximal to the periosteum of the patient.

13. The method of claim 12 wherein the therapeutically effective amount is about 0.5 cc to about 5 cc.

14. The method of claim 4 wherein the pharmacologically active agent is selected from one or more anti-inflammatory agents.

15. The method of claim 1 wherein the particles are administered to the synovial space or area proximal to the periosteum of a joint selected from the group consisting of the knee, hip, finger, elbow and shoulder.

16. The method of claim 1, wherein the administering the plurality of particles further comprises at least one of: replacing synovial fluid in the synovial space and augmenting the synovial fluid in the synovial space, such that lubrication is provided to the joint.

17. The method of claim 1, wherein the administering the plurality of particles comprises implanting into a joint capsule of the synovial joint at least one free-floating joint cushion to augment synovial fluid in the synovial space.

18. The method of claim 1, wherein the effective proportions comprise a ratio of 7 parts of Type I collagen to 2 parts of elastin to 1 part of the one or more glycosaminoglycans.

19. The method of claim 1, wherein the effective proportions comprise a ratio of 7.5 parts of Type I collagen to 2 parts of elastin to 1 part of the one or more glycosaminoglycans.

* * * * *